(12) United States Patent
Kealey et al.

(10) Patent No.: US 6,312,753 B1
(45) Date of Patent: *Nov. 6, 2001

(54) COCOA COMPONENTS, EDIBLE PRODUCTS HAVING ENRICHED POLYPHENOL CONTENT, METHODS OF MAKING SAME AND MEDICAL USES

(75) Inventors: Kirk S. Kealey, Lancaster; Rodney M. Snyder, Elizabethtown, both of PA (US); Leo J. Romanczyk, Jr., Hackettstown, NJ (US); Hans M. Geyer, Hershey, PA (US); Mary E. Myers, Lititz, PA (US); Eric J. Whitacre, Elizabethtown, PA (US); John F. Hammerstone, Jr., Nazareth, PA (US); Harold H. Schmitz, Branchburg, NJ (US)

(73) Assignee: Mars, Incorporated, McLean, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/254,353

(22) PCT Filed: Sep. 8, 1997

(86) PCT No.: PCT/US97/15893

§ 371 Date: Aug. 9, 1999

§ 102(e) Date: Aug. 9, 1999

(87) PCT Pub. No.: WO98/09533

PCT Pub. Date: Mar. 12, 1998

Related U.S. Application Data

(63) Continuation of application No. 09/041,326, filed on Mar. 12, 1998, now Pat. No. 6,194,020, and a continuation of application No. 08/709,406, filed on Sep. 6, 1996, now Pat. No. 6,015,913.

(51) Int. Cl.[7] .......... C07D 311/78; A01N 65/00; A23L 1/28; A23G 1/02
(52) U.S. Cl. .......... 426/631; 426/542; 426/593; 549/386; 424/195.1
(58) Field of Search .......... 426/631, 593, 426/542; 549/386; 424/195.1

(56) References Cited

U.S. PATENT DOCUMENTS

| 2,417,078 | 3/1947 | Jones | 241/48 |
|---|---|---|---|
| 2,558,854 | 7/1951 | Kempf et al. | 99/23 |
| 2,771,927 | 11/1956 | Thaning | 146/227 |

(List continued on next page.)

FOREIGN PATENT DOCUMENTS

| 1379116 | 1/1975 | (GB) | B02B/5/00 |
|---|---|---|---|
| WO96/10404 | 4/1996 | (WO) . | |
| WO99/45788 | * 9/1999 | (WO) . | |

OTHER PUBLICATIONS

Beckett, S.T., Ed., "Industrial Chocolate Manufacture and Use", 2nd Ed., Published by Blackie Academic Professional (an imprint of Chapman & Hall) Glasgow, U.K., 1994, by Chapman & Hall, pp. 55–82.

(List continued on next page.)

Primary Examiner—Carolyn Paden
(74) Attorney, Agent, or Firm—Margaret B. Kelley, Esq.; Clifford Chance Rogers & Wells, LLP

(57) ABSTRACT

Cocoa components having enhanced levels of cocoa polyphenols, processes for producing the cocoa components while conserving a significant amount of the cocoa polyphenols, compositions containing the cocoa components or the cocoa polyphenols, and methods of using the cocoa components or the cocoa polyphenols for improving the health of a mammal are described. The cocoa components include partially and fully defatted cocoa solids, cocoa nibs and fractions derived therefrom, cocoa polyphenol extracts, cocoa butter, chocolate liquors, and mixtures thereof. The invention provides processes for extracting fat from cocoa beans and for otherwise processing cocoa beans to yield a cocoa component having conserved concentrations of polyphenols relative to the starting materials.

33 Claims, 5 Drawing Sheets

U.S. PATENT DOCUMENTS

| | | | |
|---|---|---|---|
| 3,141,777 | 7/1964 | Guidarelli et al. | 99/88 |
| 3,904,777 | 9/1975 | Goerling et al. | 426/631 |
| 3,923,847 | 12/1975 | Roselius et al. | 260/412.8 |
| 3,955,489 | 5/1976 | Goerling et al. | 99/483 |
| 3,997,680 | 12/1976 | Chalin | 426/262 |
| 4,235,939 | 11/1980 | Kimberley, Sr. | 426/549 |
| 4,271,754 | 6/1981 | Homann | 100/37 |
| 4,322,444 | 3/1982 | Zuilichem et al. | 426/241 |
| 4,435,436 | 3/1984 | Terink et al. | 426/631 |
| 4,444,798 | 4/1984 | Magnolato et al. | 426/422 |
| 4,701,337 | 10/1987 | Frost et al. | 426/660 |
| 4,704,292 | 11/1987 | Kattenberg | 426/565 |
| 4,758,444 | 7/1988 | Terauchi et al. | 426/593 |
| 4,784,866 | 11/1988 | Wissgott | 426/262 |
| 4,810,516 | 3/1989 | Kong-Chan | 426/548 |
| 4,871,562 | 10/1989 | Terauchi et al. | 426/330.3 |
| 4,999,197 | 3/1991 | Wursch | 424/195.1 |
| 5,009,917 | 4/1991 | Wiant et al. | 426/631 |
| 5,114,730 | 5/1992 | Ellis | 426/593 |
| 5,244,099 | 9/1993 | Zaltzman et al. | 209/466 |
| 5,252,349 | 10/1993 | Carter, Jr. | 426/482 |
| 5,405,633 | 4/1995 | Heidlas et al. | 426/442 |
| 5,464,649 | 11/1995 | St. John et al. | 426/660 |
| 5,474,795 | 12/1995 | Surber et al. | 426/660 |
| 5,505,982 | 4/1996 | Krawczyk et al. | 426/660 |
| 5,554,645 * | 9/1996 | Romanczyk | 514/453 |
| 6,015,913 * | 1/2000 | Kealey et al. | 549/386 |
| 6,194,020 * | 2/2001 | Myers | 426/631 |

OTHER PUBLICATIONS

Minifie, Bernard W., Chocolate, Cocoa and Confectionery: Science and Technology, $3^{rd}$ Ed., Published by Chapman & Hall, Nw York, 1989, by Van Nostrand Reinhold, pp. 31–51 and 61–76.

Swern, D., Ed., Bailey's Industrial Oil and Fat Products', $4^{th}$ Ed., John Wiley & Sons, New York, NY, (1982) vol. 2. pp 175–251.

Wood, G.A.R., "Cocoa" $4^{th}$ Edition, Longman Scientific and Technical, Essex, England (1985), pp510–513.

Kashket et a. *Arch. Oral Biol. 30*:11–12 821–6 (1985).

Clapperton J., et al., "Polyphenols and Chocolate Flavour." Proc. Group Polyphenols, Lisbon. Portugal, (1992).

Cook, L. Russell et al., "Chocolate Production and Use", Published by Harcourt Brace Jovanovich, Inc., New York, NY (1982), pp. 143–155 and 162–172.

* cited by examiner

COCOA COMPONENTS, EDIBLE PRODUCTS HAVING ENRICHED POLYPHENOL CONTENT, METHODS OF MAKING SAME AND MEDICAL USES

This application is a continuation of U.S. application Ser. No. 09/041,326, filed Mar. 12, 1998, now U.S. Pat. No. 6,194,020, which was the National Stage of International application Ser. No. PCT/US97/15893, filed Sep. 8, 1997 and a continuation of U.S. Ser. No. 08/709,406, filed Sep. 6, 1996, now U.S. Pat. No. 6,015,913.

CROSS-REFERENCE TO RELATED APPLICATIONS

Reference is made to copending U.S. applications Ser. No. 08/317,226, filed Oct. 3, 1994 (allowed, now U.S. Pat. No. 5,554,645), Ser. No. 08/631,661, filed Apr. 2, 1996, Ser. No. 08/709,406, filed Sep. 6, 1996, now U.S. Pat. No. 6,015,913 and Ser. No. 08/831,245, filed Apr. 2, 1997, incorporated herein by reference.

BACKGROUND OF THE INVENTION

1. Field of the Invention

The invention relates to cocoa components having enhanced levels of cocoa polyphenols, processes for producing the same, methods of using the same and compositions containing the same. More specifically, the invention provides a method of producing cocoa components having an enhanced content of cocoa polyphenols, in particular procyanidins. The cocoa components include partially and fully defatted cocoa solids, cocoa nibs and fractions derived therefrom, cocoa polyphenol extracts, cocoa butter, chocolate liquors, and mixtures thereof.

The invention also relates to versatile novel processes for extracting fat from cocoa beans and/or processing cocoa beans to yield a cocoa component having a conserved level of polyphenols, in particular procyanidins. The invention provides a significantly less complex process with respect to total cost of process equipment, maintenance, energy and labor, with the concomitant benefit of obtaining components having conserved concentrations of polyphenols relative to the starting materials.

2. Description of the Related Art

Documents are cited in this disclosure with a full citation for each. These documents relate to the state-of-the-art to which this invention pertains, and each document cited herein is hereby incorporated by reference.

Confections and other edible compositions containing cocoa components have a very distinct taste and mouthfeel that have been enjoyed by individuals for many years. The unique flavor and mouthfeel of chocolate, for example, is a result of the combinations of its numerous components as well as its process of manufacture. It is well known that the mouthfeel and aroma/flavor of a chocolate are factors which greatly influence the desirability of the final chocolate product. Accordingly, the primary focus of conventional processes using cocoa components is the development of the distinctive chocolate mouthfeel and flavor/aroma. Throughout the entire chocolate manufacturing process, from the selection of the cocoa beans as a commodity at the country of origin to the tempering and solidification of the final chocolate, the development of the appropriate mouthfeel and/or aroma/flavor of the final product dictates the selections made and the process parameters used.

Chocolate contains solid particles dispersed throughout a fat matrix. Factors that influence the mouthfeel of a chocolate include the particle size distribution of the solids, the properties of the fat matrix material and how the chocolate is made.

Cocoa butter is typically the predominant fat in the chocolates. Cocoa butter is solid at room temperature (21°–24° C.) and thus most chocolates are firm and solid at room temperature providing good "snap" at initial bite. Above room temperature, the fat phase melts progressively until it is completely melted at about 36° C. This rapid melting in the mouth, at body temperature, provides the smooth, creamy mouthfeel which results in a strong flavor impact.

The flavor/aroma characteristics of the cocoa product are dependent on the combination of numerous solid and fat components as well as the process of manufacture. The flavor/aroma characteristics are dependent on (1) initial cocoa bean selection (i.e, level of fermentation, genotype, origin, etc.), (2) method of processing the beans (i.e., cleaning, roasting, shell removal, etc.) (3) processing of the cocoa components (i.e., milling) and (4) final processing to form the final product (i.e., selection of cocoa component and other ingredients, conching, etc.).

The several roles of selecting beans, fermenting them, cleaning them and processing them to obtain good flavor and other desirable characteristics is well known and is described below.

1. The Cocoa Bean

Cocoa beans are derived from cocoa trees which are found in warm, moist climates in areas about 20 degrees latitude north and south of the Equator. In general, the seeds of the *Theobroma cacao* (of the order Sterculiacae) are known chiefly in two varieties: Criollo and Forastero, with Forastero divided into several varieties. A third group, called Trinitario, is essentially a cross between Criollo and Forastero and is not found in the wild. Freshly harvested raw Criollo beans are pale brown in color while Forastero beans are a purple hue.

The cocoa bean is comprised of an inner nib portion covered by an outer shell. After conventional drying, the shell of the bean comprises about 12 to 15% of the weight of the bean, while the nib and residual moisture amounts to approximately 85 to 88%. Typical analytical data ranges for chemical components of cocoa nib are: fat content of 48 to 57%; theobromine content of 0.8 to 1.3%; caffeine content of 0.1 to 0.7%; total nitrogen content of 2.2 to 2.5%; ash content of 2.6 to 4.2%; and water content of 2.3 to 3.2% (see *Pearson's Composition and Analysis of Foods*, 9th Ed., 1991).

2. Fermentation of the Bean

Fermentation, an early step in the processing of cocoa beans, is important to the development of suitable flavors and/or flavor precursors. It was previously believed that fermentation and drying of the cocoa beans were "of vital importance as no subsequent processing of the bean will correct that practice at this stage" (*Chocolate, Cocoa and Confectionery: Science and Technology*, 3rd Ed., by Bernard W. Minifie, p. 13 (1989)). During the fermentation and drying processes, the unfermented wet beans taken from the pod lose about 65 percent of their weight, assuming the final optimum moisture content of 6 percent is attained (Minifie, p. 14). The level of fermentation in the dried cocoa bean is typically determined by the "cut test" (defined further below).

It is well known in the art that flavor in the final cocoa or chocolate is closely related to fermentation. For example, if the beans are cleaned and separated from the pulp and dried without any fermentation, the nib will not be the brown or purple-brown color of fermented dry cocoa beans but instead a slaty grey color (*Industrial Chocolate Manufacture and Use*, 2nd Ed., by S. T. Beckett, p. 13). Chocolate made from slaty, unfermented beans typically tastes very bitter and astringent without any apparent chocolate flavor (Beckett, p. 13).

Accordingly, fully fermented cocoa beans are more desirable than underfermented cocoa beans from a flavor/aroma standpoint and typically sell at a higher price. The fermented cocoa beans are usually used to produce chocolate liquors.

Underfermented beans are conventionally processed for their cocoa butter. The quality of the cocoa butter is not affected by underfermentation. The quality of the cocoa solids, however, is affected since they do not contain sufficient color, flavor/aroma and are therefore either discarded or sold for low-value uses. Although chocolate liquors and/or partially defatted cocoa solids are sometimes produced from a nonhomogeneous mass of beans containing a portion of underfermented beans, the resultant liquor or solids require subsequent treatment or processing. Since unfermented beans are not conventionally processed commercially, they are not typically available.

3. Bean Cleaning

Once the cocoa beans are selected, they are cleaned to remove extraneous matter and then processed. The initial step consists of cleaning the beans to remove extraneous non-cocoa materials. Conventional bean cleaning separates beans from extraneous non-cocoa materials by either size or density using a cleaning machine which is a gravity, vibratory or aspiration table (see Minifie, p. 35; *Chocolate Production and Use*, 3rd Ed., by L. Russell Cook, pp. 144–146; and Beckett, p. 55).

Current cocoa bean cleaning technology is typically limited in separation ability to a minimum density difference of 10–15%. This reduces the efficiency of achieving an accurate separation of bean and extraneous non-cocoa materials and therefore reduces the clean bean yield of the process. Additionally, conventional cleaning machines become easily clogged and require frequent cleaning. This also reduces the cleaning efficiency and the clean bean yield of the overall process.

Moreover, conventional cleaning machines have a tendency to fracture the beans during cleaning which reduces the percentage of whole beans available after cleaning. These broken bean pieces can later give rise to problems during roasting and winnowing. For instance, small bean pieces will burn readily at the elevated temperatures used during roasting and may result in burnt and ashy flavored liquors which are unacceptable from a flavor standpoint. Small bean pieces may also decrease the efficiency of the winnowing process because they can be lost during the aspiration of the shells and result in overall yield efficiency losses.

4. Bean Roasting

In most conventional processes, roasting of the whole bean or nib is an essential step in the manufacture of chocolate liquor or partially defatted cocoa solids. Whole bean roasting was previously believed to be critical for developing the natural flavor and aroma of the cocoa beans and reducing the moisture content of the bean to below about 2% by weight. Whole bean roasting also loosens the shell so that it can be readily removed during the winnowing process. The degree of cocoa roast is a time/temperature dependent relationship, where the time can vary from 5 to 120 minutes and the temperature of the whole bean can typically vary from 120° C. to 150° C. In the pre-roasting of whole beans, an initial heating step can be performed at just below 100° C., followed by roasting of the nibs at elevated temperatures up to about 130° C. (see Minifie, especially pp. 37 and 45–46; Cook, pp. 146–152; Beckett, pp. 55–64; and U.S. Pat. No. 5,252,349 to Carter, Jr.).

5. Winnowing-Shell Removal

The winnowing operation serves to separate the beans into the desired inner portion of the bean (nib) and the outer portion of the bean (shell). The principle of separation by a winnowing process depends on the difference in the apparent density of the nib and of the shell. Standard winnowing machines make use of the combined action of sieving and air aspiration. The shell is loosened during the conventional roasting and/or other heating steps. After loosening, the beans are typically broken between rollers to shatter the cocoa beans along natural fracture lines of the cocoa nib to facilitate shell removal during winnowing (see U.S. Pat. No. 2,417,078 to Jones; U.S. Pat. No. 5,252,349 to Carter, Jr.; Minifie, pp. 47–51; Cook, pp. 152–153; and Beckett, pp. 67–68).

Some cocoa bean processing techniques include a heat pre-treatment step to aid in the separation of the shell from the nib. This involves giving the beans a thermal shock by hot air, steam or infra-red heat (see U.S. Pat. No. 4,322,444 to Zuilichem et al.; British Patent No. 1,379,116 to Newton; Minifie, pp. 44–43; Cook, p. 155; and Beckett, pp. 60–62).

Infra-red heat pre-treatment uses infra-red heating to rapidly heat and expand the beans. This loosens the shells. The method consists of exposing the beans to infra-red radiation for a period of between one half and two minutes, during which time the beans are typically heated to a temperature of about 100 to 110° C. The infra-red radiation used has a wavelength between 2 and 6 microns which corresponds to a frequency in the range of 0.7 to $1.2 \times 10^8$ megacycles per second.

6. Formation of Chocolate Liquor and other Cocoa Components

The next step in conventional cocoa processing, after winnowing, involves nib grinding. Nib grinding is typically performed in two stages, an initial grinding stage to convert the solid nibs into a fluid paste and a final grinding stage to achieve the desired particle size. Both of these stages are equipment, maintenance, and energy intensive.

The cleaned roasted cocoa nibs typically vary in cocoa butter content from 50–58% by weight. During the grinding, the nib is ground, for instance by milling, into a fluid, dark brown "liquor". The fluidity is due to the breakdown of the cell walls and the release of the cocoa butter during the processing. Ground particles of partially defatted cocoa solids are suspended in the cocoa butter. This liquor is sometimes commercially sold as a product useful in the confectionery and baking industries where machinery for processing the cocoa beans is not available.

Other conventional cocoa processing includes separating cocoa butter from liquor. This is accomplished by using a batch hydraulic pot press ("hydraulic press") to separate the cocoa butter from the cocoa solids. The resultant cocoa butter is subsequently filtered to yield a clear, solid-free cocoa butter. Butter can also be produced by a continuous screw press to extract the butter from whole bean with shell or less frequently, from nibs (see U.S. Pat. No. 5,252,349 to Carter, Jr.; and Minifie, especially pp. 71–72).

The resulting cocoa cake from either hydraulic presses or screw presses may be milled into cocoa powder. Cocoa cake typically contains either 10–12% cocoa fat or 20–22% cocoa fat (see Minifie, pp. 72–76; Cook, pp. 169–172; and Beckett, pp. 78–82). Cocoa powder from cocoa cake obtained by hydraulic pressing is usually produced by milling the cocoa cake. If natural cocoa powder is desired, cocoa cake is fed directly to the cocoa cake mill. If alkalized cocoa powder is desired, the cake from an alkalizing process is fed to the mill. Hydraulic pressing produces a cocoa cake which is an agglomerate of previously milled cocoa particles. Cocoa cake mills for cocoa cake from hydraulic pressing are therefore designed to reduce the size of these agglomerates.

The natural cocoa cake or natural cocoa powder can be further processed by alkalizing to modify the color and flavor qualities of the cake (see U.S. Pat. No. 3,997,680 to Chalin; U.S. Pat. No. 5,009,917 to Wiant, et al.; Minifie, pp. 61–67; Cook, pp. 162–165; and Beckett, pp. 71–72). The alkalizing process can be used at any of several different stages of processing and includes the treatment of either the beans, liquor, nib, cake or powder with solutions or suspensions of alkali, usually, but not limited to, sodium or potassium carbonate. After alkalizing, the cocoa solids are dried and cooled. The dried cocoa solids are subsequently milled to produce alkalized cocoa powder, and thereafter cooled and packaged.

7. Polyphenols in Cocoa Beans and Their Utility

Cocoa beans contain polyphenols. These polyphenols have recently been extracted and screened for biological activity. It has been discovered that cocoa polyphenol extracts, particularly procyanidins, have significant biological utility. The extracts or compounds further separated therefrom have generally been prepared, on a laboratory scale, by reducing cocoa beans to a powder, defatting the powder, and extracting and purifying the active compound (s) from the defatted powder. The powder is generally prepared by freeze-drying the cocoa beans and pulp, depulping and deshelling the freeze-dried beans and grinding the deshelled beans or nibs. The extraction of active compound (s) has been accomplished by solvent extraction techniques, and the extracts have been purified by gel permeation chromatography, preparative High Performance Liquid Chromatography (HPLC) techniques, or by a combination of such methods (see U.S. Pat. No. 5,554,645 to Romancyzk et al.).

It has now been determined that the recovery of polyphenols appears to be inversely proportional to the degree of fermentation of the cocoa beans. Accordingly, the use of fermented beans as a feedstock material, which is important for good chocolate flavor, reduces the amount of polyphenols available in the cocoa component(s) derived from the beans.

It has also been determined that higher processing temperatures and/or longer processing times, e.g. in the roasting step, reduces the amount of polyphenols available in the cocoa components derived from the feedstock beans. Cocoa components have not, heretofore, been produced having substantial quantities of polyphenols. These problems in the art have not heretofore been recognized.

OBJECTS OF THE INVENTION

It is an object of the invention to overcome the above-mentioned difficulties and/or deficiencies in the prior art.

More specifically, it is an object of the invention to provide methods of selecting and/or processing cocoa beans for producing cocoa components having enhanced levels of cocoa polyphenols.

It is a further object of the invention to provide a method of processing cocoa beans, wherein a significant amount of cocoa polyphenols present in the pre-processed bean is conserved in the processed bean.

It is yet another object of the invention to provide cocoa components, including cocoa nibs or portions thereof, chocolate liquor and partially or fully defatted cocoa solids, each having enhanced levels of cocoa polyphenols, and products containing the cocoa components.

It is an additional object of the invention to provide a method of manufacturing chocolates, chocolate-flavored confections, chocolate-flavored compositions, edible compositions, supplements, and combinations thereof having enhanced levels of cocoa polyphenols or derivatives thereof.

It is a further object of the invention to provide a method of improving the health of a mammal using the products of the invention.

It is a still further object of the invention to provide a method of improving the flavor/aroma characteristics of cocoa components, particularly chocolate liquor, containing enhanced levels of cocoa polyphenols.

It is a still further object of the invention to provide a method of producing cocoa butter and cocoa solids having a high yield of cocoa butter per amount of cocoa beans processed.

It is another object of the invention to provide a method of winnowing beans to remove the shell portion from the inner portion using an air fluidized bed density separation system.

It is another object of the invention to provide a method of producing high quality cocoa butter without requiring a bean roasting step or a liquor milling step.

These and other objects and advantages of the invention will become further apparent from the teachings hereinafter provided by the detailed description, test data, and examples.

SUMMARY OF THE INVENTION

The invention relates to novel versatile methods of processing cocoa beans to form cocoa components having improved properties or characteristics, products made from those methods and methods of using the same. More specifically, the invention relates to methods of producing cocoa components having enhanced levels of cocoa polyphenols. Parameters of the several cocoa processing steps, including the selection of the cocoa bean feedstock, are controlled and/or manipulated to result in a valuable cocoa component while conserving a significant amount of the cocoa polyphenol content present in the cocoa bean. Thus, the invention relates to methods of obtaining cocoa components having conserved levels of cocoa polyphenols relative to the starting materials, and to the products of those processes produced thereby. The invention avoids the significant and detrimental losses of cocoa polyphenols that occur during conventional processing.

The invention also relates to novel cocoa components having enhanced levels of cocoa polyphenols produced by the methods of the invention. More specifically, the invention relates to novel cocoa components including cocoa nibs or portions thereof, chocolate liquors, partially or fully defatted cocoa solids, cocoa polyphenol extract, and combinations thereof having higher levels of cocoa polyphenols in comparison with conventionally produced cocoa components.

The invention also relates to novel compositions containing the novel cocoa components including edible products, chocolates, chocolate-flavored confections, chocolate-flavored compositions, ingestible products, digestible products, chewable compositions and combinations thereof. The invention is thus in novel products having enhanced levels of cocoa polyphenols and novel products containing a cocoa polyphenol additive or a derivative thereof. The additive may be an extract from cocoa beans or a cocoa component thereof, or may be synthetic.

The invention further relates to the treatment of cocoa components, particularly chocolate liquors, to provide a cocoa component having high levels of cocoa polyphenols with acceptable aroma/flavor characteristics. The treatment includes the removal of undesirable and/or off flavors that may be present in a cocoa component, the manipulation of the aroma/flavor profile using additives or the blending of cocoa components having varying levels of cocoa polyphenols and varying degrees of aroma/flavor.

The invention also relates to methods for the production of cocoa polyphenol extract from cocoa beans or components thereof and to the use of the extract as an additive to edible compositions.

The invention also relates to novel methods of improving the health of a mammal, particularly humans, using the products containing cocoa polyphenols, particularly products containing elevated levels of cocoa polyphenols. These methods include the use of the cocoa polyphenols to provide one or more of the following activities: reducing periodontal disease, antigingivitis, antiperiodontis, reducing atherosclerosis, LDL oxidation inhibitor, reducing hypertension, antineoplastic, antioxidant, DNA topoisomerase II enzyme inhibitor, cyclo-oxygenase modulator, lipoxygenase modulator, nitric oxide (NO) or NO-synthase modulator, non-steroidal anti-inflammatory, apoptosis modulator, platelet aggregation modulator, blood or in vivo glucose modulator, antimicrobial and inhibitor of oxidative DNA damage activity.

BRIEF DESCRIPTION OF THE DRAWINGS

FIG. 1(a) depicts the cut bean half of an unfermented cocoa bean; FIGS. 1(b)–(d) depict the cocoa bean as it is fermented, with FIG. 1(d) illustrating the fully fermented cocoa bean;

DESCRIPTION OF THE PREFERRED EMBODIMENTS Definitions

Figure 1A:
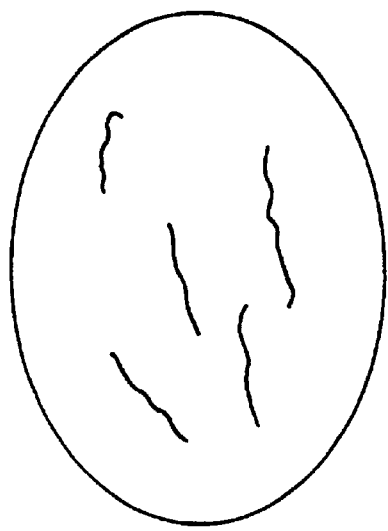
FIGS. 1(a)–(d) illustrate the change in the surface of the cut bean half during the fermentation of the cocoa bean.

1. The term "chocolate" refers to a solid or semi-plastic food and is intended to refer to all chocolate or chocolate-like compositions containing a dispersion of solids within a fat phase. The term is intended to include compositions conforming to the U.S. Standards Of Identity (SOI), CODEX Alimentarius and/or other international standards and compositions not conforming to the U.S. Standards Of Identity or other international standards. The term includes sweet chocolate, bittersweet or semisweet chocolate, milk chocolate, buttermilk chocolate, skim milk chocolate, mixed dairy product chocolate, sweet cocoa and vegetable fat coating, sweet chocolate and vegetable fat coating, milk chocolate and vegetable fat coating, vegetable fat based coating, pastels including white chocolate or coating made with cocoa butter or vegetable fat or a combination of these, nutritionally modified chocolate-like compositions (chocolates or coatings made with reduced calorie ingredients) and low fat chocolates, unless specifically identified otherwise.

In the United States, chocolate is subject to a standard of identity established by the U.S. Food and Drug Administration (FDA) under the Federal Food, Drug and Cosmetic Act. Definitions and standards for the various types of chocolate are well established in the U.S. Nonstandardized chocolates are those chocolates which have compositions that fall outside the specified ranges of the standardized chocolates.

The fat phase of the chocolate of the invention can include cocoa butter, milkfat, anhydrous milkfat, butteroil, and other vegetable fat and other modifications of these fats (CBR, CBE and CBS, referring to cocoa butter replacers, equivalents and substitutes) and synthetic fats or mixtures of cocoa butter with these fats. See Minifie, pp. 100–109.

The chocolate may contain a sugar syrup/solids, invert sugar, hydrolyzed lactose, maple sugar, brown sugar, molasses, honey, sugar substitute and the like. The term "sugar substitute" includes bulking agents, sugar alcohols (polyols such as glycerol), or high potency sweeteners or combinations thereof. Nutritive carbohydrate sweeteners with varying degrees of sweetness intensity may be any of those typically used in the art and include, but are not limited to, sucrose, e.g. from cane or beet, dextrose, fructose, lactose, maltose, glucose syrup solids, corn syrup solids, invert sugar, hydrolyzed lactose, honey, maple sugar, brown sugar, molasses and the like. Sugar substitutes may partially replace the nutritive carbohydrate sweetener. High potency sweeteners include aspartame, cyclamates, saccharin, acesulfame-K, neohesperidin dihydrochalcone, sucralose, alitame, stevia sweeteners, glycyrrhizin, thaumatin and the like and mixtures thereof. The preferred high potency sweeteners are aspartame, cyclamates, saccharin, and acesulfame-K. Examples of sugar alcohols may be any of those typically used in the art and include sorbitol, mannitol, xylitol, maltitol, isomalt, lactitol and the like.

The chocolates may also contain bulking agents. The term "bulking agents" as defined herein may be any of those typically used in the art and include polydextrose, cellulose and its derivatives, maltodextrin, gum arabic, and the like.

The chocolate products may contain emulsifiers. Examples of safe and suitable emulsifiers may be any of those typically used in the art and include lecithin derived from vegetable sources such as soybean, safflower, corn, etc., fractionated lecithins enriched in either phosphatidyl choline or phosphatidyl ethanolamine, or both, mono- and digylcerides, diacetyl tartaric acid esters of mono- and diglycerides (also referred to as DATEM), monosodium phosphate derivatives of mono- and diglycerides of edible fats or oils, sorbitan monostearate, hydroxylated lecithin, lactylated fatty acid esters of glycerol and propylene glycol, polyglycerol esters of fatty acids, propylene glycol mono- and di-esters of fats and fatty acids, or emulsifiers that may become approved for the US FDA-defined soft candy category. In addition, other emulsifiers that can be used include polyglycerol polyricinoleate (PGPR), ammonium salts of phosphatidic acid, (e.g. YN) sucrose esters, oat extract, etc., any emulsifier found to be suitable in chocolate or similar fat/solid system or any blend.

2. The term "chocolate-flavored confection" refers to food products, excluding "chocolate", having a chocolate flavor/aroma and comprising a cocoa fraction. These products are stable at ambient temperatures for extended periods of time (e.g., greater than 1 week) and are characterized as microbiologically shelf-stable at 18–30° C. under normal atmospheric conditions. Examples include chocolate-flavored hard candies, chewables, chewing gums, etc.

3. The term "chocolate-flavored compositions" refers to chocolate-flavored compositions, excluding "chocolate", containing a cocoa fraction and having a chocolate flavor/aroma. Examples include chocolate-flavored cake mixes, ice creams, syrups, baking goods, etc.

4. The term "fats", as used herein, refer to triglycerides, diglycerides and monoglycerides that can normally be used in chocolates and chocolate-like products. Fats include the naturally occurring fats and oils such as cocoa butter, pressed cocoa butter, expeller cocoa butter, solvent extracted cocoa butter, refined cocoa butter, milkfat, anhydrous milkfat, fractionated milkfat, milkfat replacers, butterfat, fractionated butterfat, cocoa butter equivalents (CBE), cocoa butter substitutes (CBS), cocoa butter replacers (CBR), reduced calorie fats and/or synthetically modified fats such as Caprenin®. An example of a reduced calorie fat is Caprocaprylobehein (commonly known as Caprenin®) as described in U.S. Pat. No. 4,888,196 to Ehrman, et al., which is incorporated herein by reference.

5. The term "food product" includes any food product, for example, those set forth in 21 CFR § 101.12. The term includes chocolate-flavored compositions (e.g., cakes, nougats, puddings, etc.), as well as compositions not having a chocolate-flavor (e.g., caramels, etc.)

6. The term "fermentation factor" is a numerical quantification of the level of fermentation of a batch of cocoa beans. Fermentation factors range from 100 (under/unfermented) to 400 (fully fermented).

In order to assess the degree of fermentation, cocoa beans are typically subjected to a standard cut test for assessing quality as defined in industry grade standards. The bean halves are laid out on a board for visual inspection of color as well as defects which can arise during bean fermentation, drying and/or storage.

Beans can be divided into four fermentation categories according to their color and appearance: (a) fully fermented, e.g., predominantly a brown hue; (b) partially fermented, e.g., purple/brown; (c) purple (underfermented); and (d) slaty (very underfermented and/or unfermented beans).

Purple/brown beans include all beans showing any blue, purple or violet color on the exposed surface, whether suffused or as a patch. Purple beans should include all beans showing a completely blue, purple or violet color over the whole exposed surface. This should also include, irrespective of color, any beans which are slaty, but not predominantly so (wherein predominantly, in this context, means more than half).

The "fermentation factor" is determined using a grading system for characterizing the fermentation of the cocoa beans. Slaty, being under/unfermented, is designated as 1, purple as 2, purple/brown as 3 and brown as 4. The percentage of beans falling within each category is multiplied by the weighted number. Thus, the "fermentation factor" for a sample of 100% brown beans would be 100×4 or 400, whereas the fermentation factor for a sample of 100% purple beans would be 100×2 or 200. A sample of 50% slaty beans and 50% purple beans would have a fermentation factor of 150 [(50×1)+(50×2)].

Cut tests applicable to cocoa beans derived from the Trinitario and Forastero types may or may not be applicable to cocoa beans derived from the Criollo type, for example, where bean color variation ranging from fully purple to light tan can be encountered. Accordingly, the cut test based on color would not be applicable to specific cocoa genotypes lacking the anthocyanin pigments responsible for the purple color, such as the Catango (or Catongo) type whose beans are light tan in color. Other exceptions include "cocoa beans" derived from other Theobroma species, the Herrania species and their inter- and intra-specific crosses. The beans from these species are "tan" in color. For these types of beans the level of fermentation may be determined using a modified standard cut test. Using the modified test, the surface of the bean (halved) is inspected for the degree of lines, fissures or cracks which form during fermentation, rather than the change of color.

Figure 1B:
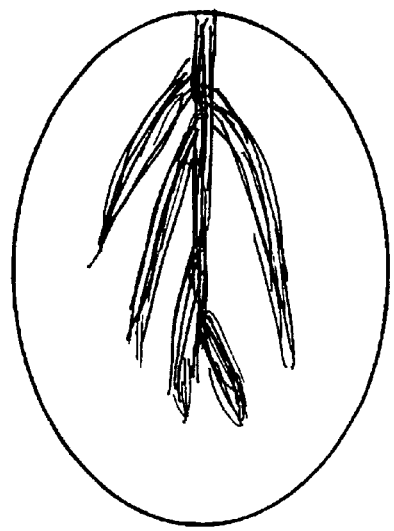
Figure 1C:
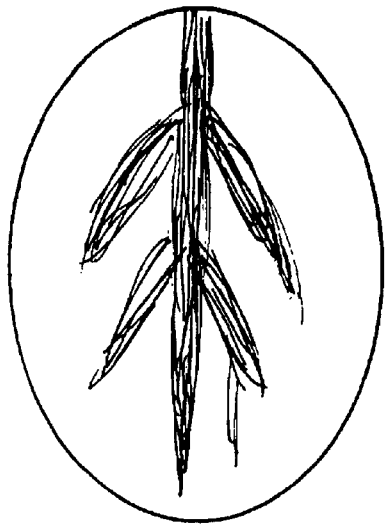
Figure 1D:
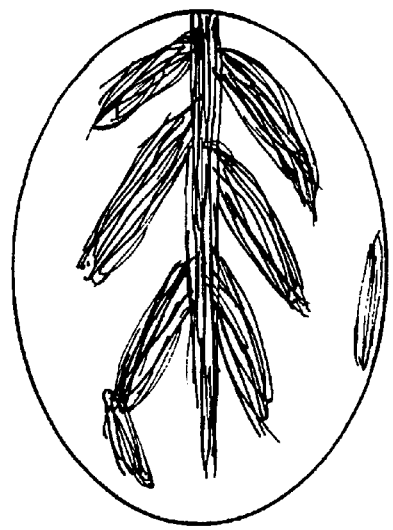

FIGS. 1(a)–(d) illustrate the change in the surface of the cut bean half during the fermentation of the cocoa bean. As can be seen from FIGS. 1(a)–(d), the number of lines/fissures and the extent to which they extend across the entire surface of the cut bean half increases as the bean is fermented. FIG. 1(a) depicts the cut bean half of an unfermented cocoa bean where the surface is relatively smooth. FIGS. 1(b)–(d) depict the cocoa beans as it is fermented, with FIG. 1(d) illustrating the fully fermented cocoa bean. As the cocoa bean is fermented, the surface develops small branch-like lines or fissures. This modified test can also be used to approximate the fermentation factor wherein a cocoa bean corresponding to FIG. 1(a) is designated as 100, FIG. 1(b) as 200, FIG. 1(c) as 300 and FIG. 1(d) as 400.

While the definitions of the aforementioned categories are a general guide, the assessment according to these categories is well within the skill of the ordinary skilled artisan well versed in chocolate and cocoa processing (see Wood et al., *Cocoa*, 4th Ed. (1985), incorporated herein by reference, especially pages 511 to 513).

7. The numerical terms or qualitative characteristics of the level of cocoa polyphenols in beans or in components refer to the amount detectable and measurable using the method of evaluating the levels set forth in Example 5.

8. The term "significant amount" means an amount which maintains the basic characteristics of the specified ingredients or composition or product.

9. The term "chocolate liquor" refers to the dark brown fluid "liquor" formed by grinding a cocoa nib. The fluidity is due to the breakdown of the cell walls and the release of the cocoa butter during the processing resulting in a suspension of ground particles of cocoa solids suspended in cocoa butter (See, *Chocolate, Cocoa and Confectionery: Science and Technology*, 3rd Ed., by Bernard W. Minifie).

10. The term "fair average quality cocoa beans" refers to cocoa beans that have been separated from the pulp material and dried and are relatively free of mold and infestation. Such beans are a commercial commodity and form the feedstock for the next step in the production processes, i.e. infra-red heating, roasting, pressing, etc. The term includes any such bean that has been genetically modified or produced.

11. The term "raw freshly harvested cocoa beans" refers to seeds or beans freshly harvested from the cocoa pod and which have not been subjected to processing other than separation from the pulp. The term includes any such bean that has been genetically modified or produced.

12. The term "partially defatted cocoa solids" refers to the solid portion(s) derived from shell-free partially defatted cocoa nibs, including cocoa powders, cocoa cake, cocoa polyphenol extracts, alkalized powders or cakes, etc. (excluding chocolate liquor and cocoa butter).

13. The term "cocoa polyphenol" refers to the polyphenol compounds present in cocoa beans and derivatives thereof. The term cocoa polyphenol is intended to include polyphenols extracted from cocoa beans and derivatives thereof, as well as structurally similar synthetic materials.

The term polyphenols includes the proanthocyanidins extracted from cocoa beans and derivatives thereof, as well as structurally similar synthetic materials and includes the procyanidins extracted from cocoa beans and derivatives thereof as well as structurally similar synthetic materials.

More specifically, the term "cocoa polyphenol" includes monomers (notwithstanding the term polyphenol) of the formula $A_n$ (where n is 1) or oligomers of the formula $A_n$ (where n is an integer from 2 to 18, and higher), wherein A has the formula:

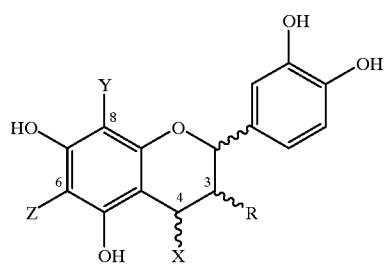

and R is 3-(α)—OH, 3-(β)—OH, 3-(α)—O-sugar, or 3-(β)—O-sugar;

bonding between adjacent monomers takes place at positions 4, 6 or 8;

a bond to a monomer in position 4 has alpha or beta stereochemistry;

X, Y and Z are selected from the group consisting of A, hydrogen, and a sugar, with the provisos that as to at least one terminal monomer, bonding of the adjacent monomer thereto is at position 4 and optionally Y=Z=hydrogen;

the sugar is optionally substituted with a phenolic moiety; and salts, derivatives and oxidation products thereof.

Advantageously, the sugar is selected from the group consisting of glucose, galactose, xylose, rhamnose and arabinose. The sugar of any or all of R, X, Y, and Z can optionally be substituted at any position with a phenolic moiety via an ester bond. The phenolic moiety is selected from the group consisting of caffeine, cinnamic, coumaric, ferulic, gallic, hydroxybenzoic and sinapic acids. One or more of the cocoa polyphenol compounds may be used simultaneously, e.g., in "combinations" in formulation(s) comprising one or more of such compounds.

The term "oligomer", as used herein, refers to any compound of the formula presented above, wherein n is 2 through 18, and higher. When n is 2, the oligomer is termed a "dimer"; when n is 3, the oligomer is termed a "trimer"; when n is 4, the oligomer is termed a "tetramer"; when n is 5, the oligomer is termed a "pentamer"; and similar recitations may be designated for oligomers having n up to and including 18 and higher, such that when n is 18, the oligomer is termed an "octadecamer".

The term "cocoa polyphenols" is further defined in U.S. applications Ser. No. 08/317,226, filed Oct. 3, 1994 (allowed, now U.S. Pat. No. 5,554,645), Ser. No. 08/631,661, filed Apr. 2, 1996, Ser. No. 08/709,406, filed Sep. 6, 1996, and Ser. No. 08/831,245, filed Apr. 2, 1997, incorporated herein by reference.

14. The term "treating" is intended to refer to methods of processing the cocoa beans including drying, heating (e.g., roasting, infra-red heating, etc.), chemical treatment (e.g., with anti-microbial agents), rehydrating, pressing, solvent extraction, microwave assisted extraction, etc.

15. The term "cocoa component" is intended to refer to a fraction derived from shell-free cocoa nib and includes chocolate liquor, partially or fully defatted cocoa solids (e.g., cake or powders), cocoa extracts, cocoa butter, cocoa nib or portions thereof, etc.

DETAILED DESCRIPTION OF THE INVENTION

A. Cocoa Bean selection

Figure 2:
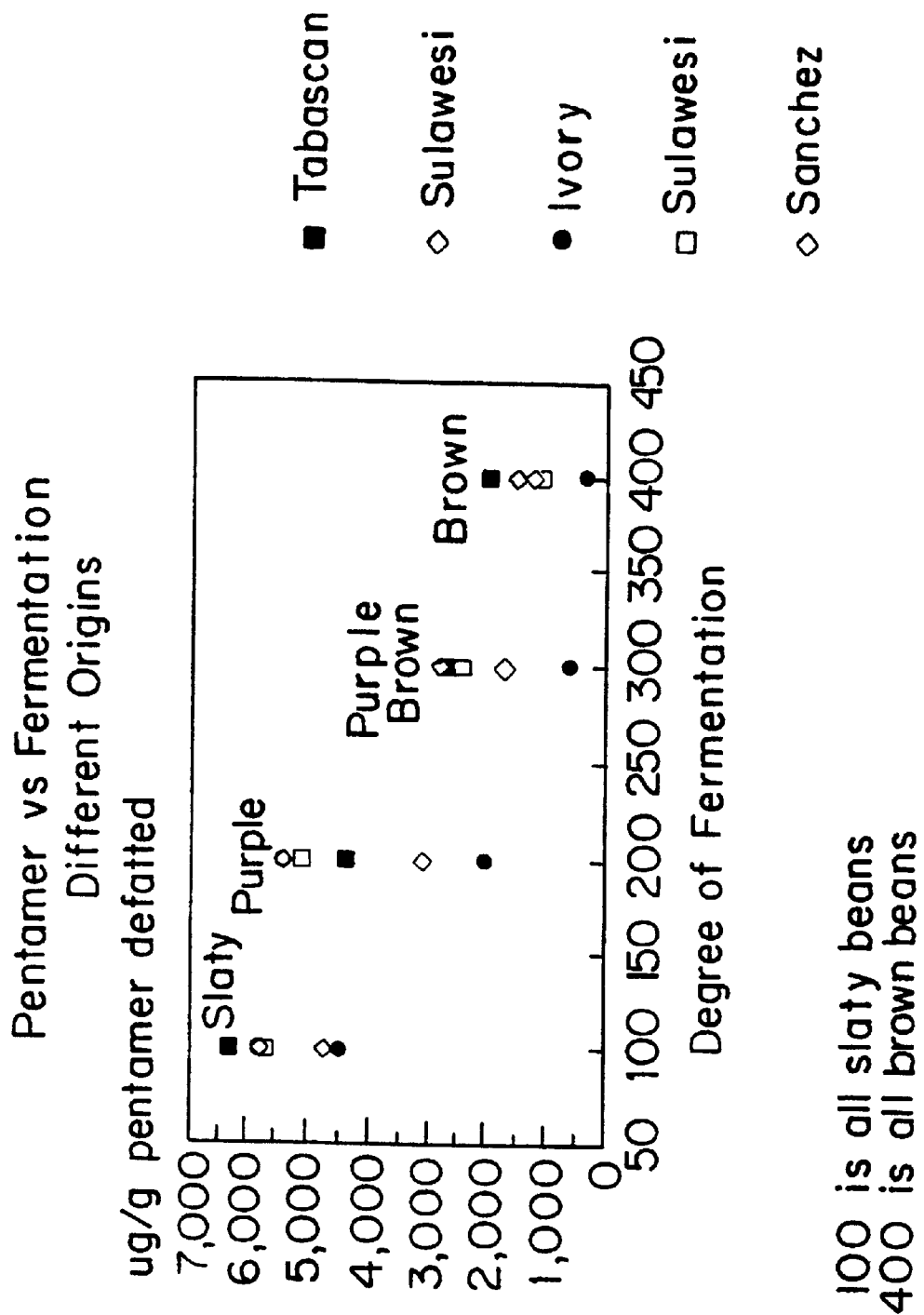
FIG. 2 is a graphical representation of cocoa polyphenols level/fermentation relationship for five cocoa bean samples, wherein the vertical axis represents the level of cocoa polyphenol pentamer (ug/g) from chocolate liquors derived from these cocoa beans defatted and the horizational axis is the degree of fermentation using the fermentation factor (as defined below)

As set forth above, conventional processes utilize fermented cocoa beans to form cocoa components. Applicants have discovered that the level of cocoa polyphenols in the cocoa beans decreases dramatically during fermentation. FIG. 2 shows the pentamer content of liquors derived from cocoa beans of different origins with varying degrees of fermentation. The data represented in this graph were collected by visually color sorting the beans. Categories used in grading were slaty, purple, purple brown, and brown—the standard categories used by the industry to grade fermentation levels of beans during a cut test. Each sample (300 g) was roasted for 15 minutes at 150° C. in a convection oven. The roasted beans were then cracked and winnowed. A liquor was produced using a Melange milling apparatus with a one hour cycle time. To make the fermentation a continuous scale (x-axis) the different colors were given a weighted number.

These results demonstrated that underfermented beans have higher polyphenol levels than fermented beans. By processing underfermented beans it is possible to make liquors with higher polyphenol contents.

Accordingly, one aspect of the invention relates to methods of producing cocoa components containing enhanced levels of cocoa polyphenols from underfermented cocoa beans. The use of underfermented cocoa beans or a blend of underfermented cocoa beans with fermented cocoa beans provides a cocoa component having enhanced levels of cocoa polyphenols.

Therefore, one embodiment of the invention relates to the use of cocoa beans having a fermentation factor less than 375, preferably less than 325, advantageously less than 275, even more advantageously less than 225, desirably less than 175 and most desirably less than 150. In another preferred embodiment underfermented cocoa beans having a fermentation factor less than 125 and even about 100 are used.

Figure 3:
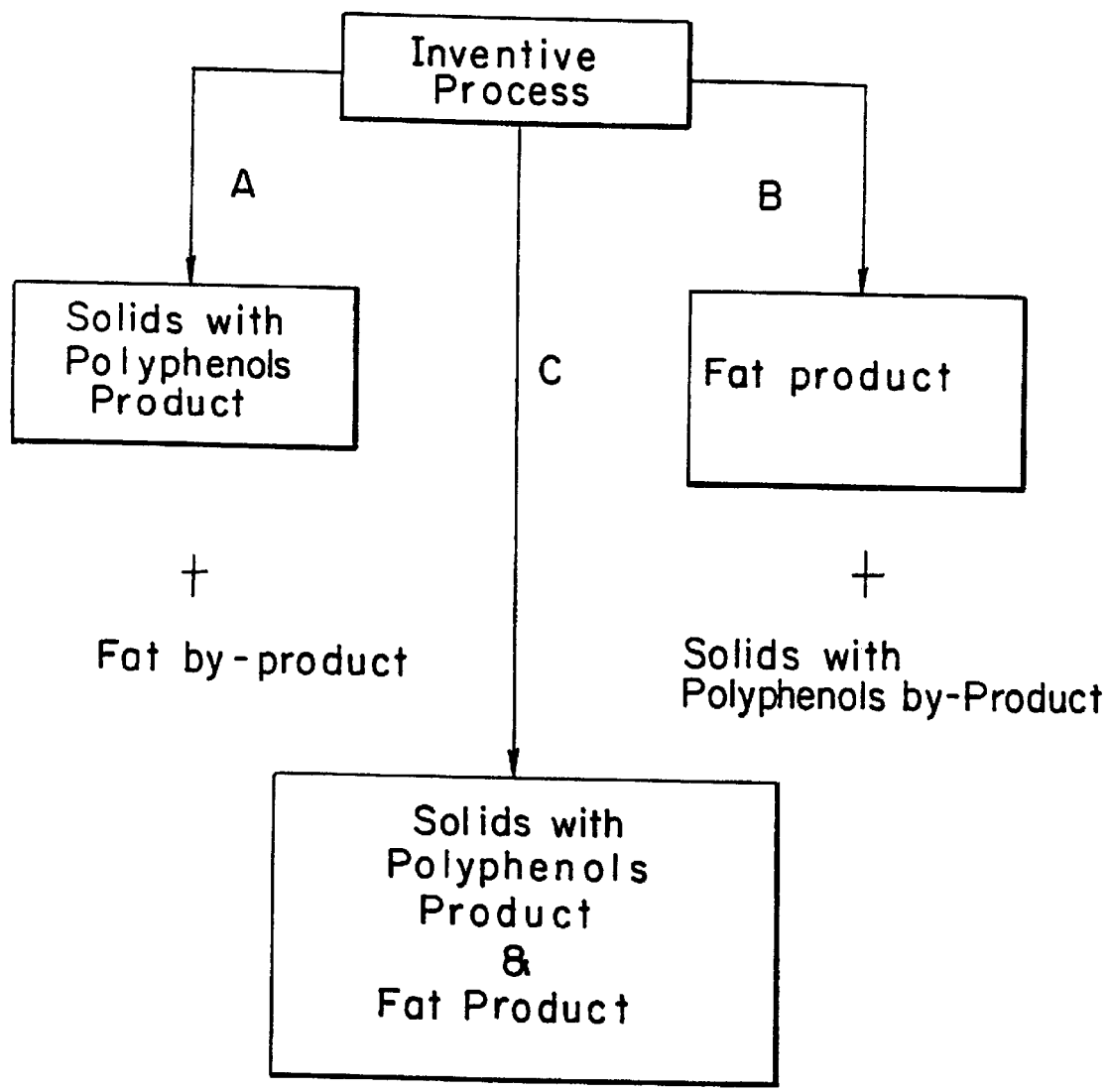
FIG. 3 shows an overview of the method of the present invention, and the various products which can be produced by the process (process options dependent upon economics of products, and/or by-products)

B. Methods of Producing Cocoa Components Having Enhanced Levels of Polyphenols An outline of one embodiment of the invention is shown in FIG. 3. The method of the invention includes modifications of certain steps of the process to produce three types of products. One process modification (Modification A) enables the production of cocoa solids containing conserved levels of polyphenols relative to the level of polyphenols in the cocoa bean feedstocks. Polyphenols are conserved in the product at higher levels than in conventional processes. Modification B enables the production of cocoa butter without necessarily the concomitant conservation of polyphenols. Modification C enables the production of cocoa solids and fat products with enhanced contents of polyphenols relative to conventional solid/fat separation processes.

In a broad embodiment of the invention a cocoa component having an enhanced content of cocoa polyphenol, is produced in a process comprising the steps of:
  (a) treating cocoa beans containing cocoa polyphenols while conserving a significant amount of the cocoa polyphenols content thereof to form treated cocoa beans; and
  (b) producing the cocoa component from the treated cocoa beans.

A significant amount of the cocoa polyphenols is conserved using the inventive methods.

The cocoa beans may be fair average quality cocoa beans, raw freshly harvested cocoa beans or combinations thereof. The cocoa beans may be unfermented, underfermented, fully fermented or mixtures thereof, with fermentation factors ranging from 100 to 400. Preferably, the cocoa beans are underfermented to enable the production of a cocoa component having the highest levels of cocoa polyphenols.

One embodiment of the invention relates to methods of processing cocoa beans which are fair average quality cocoa beans wherein the cocoa polyphenols content of the cocoa component produced is from 25 to 100% by weight of the cocoa polyphenols content of the fair average quality cocoa beans. Preferably, the cocoa polyphenols content of the cocoa component produced is greater than 35% by weight of the cocoa polyphenols content of the fair average quality cocoa beans, advantageously greater than 45% by weight, even more advantageously greater than 55% by weight, and most advantageously greater than 65% by weight. According to other preferred embodiments, more than 75% by weight is conserved, desirably more than 85% by weight, more desirably more than 95% by weight and most desirably more than 99% by weight.

Another embodiment of the invention relates to methods of processing raw freshly harvested cocoa beans wherein the cocoa polyphenols content of the cocoa component produced is from 5 to 100% by weight of the cocoa polyphenols content of the raw freshly harvested cocoa beans. Preferably, the cocoa polyphenols content of the cocoa component produced is greater than 10% by weight of the cocoa polyphenols content of the raw freshly harvested cocoa beans, advantageously greater than 15%. More advantageously greater than 20%, and still more advantageously greater than 25%. According to one preferred embodiment, greater than 30% is conserved, advantageously greater than 35%, more advantageously greater than 40% and most preferred greater than 45%. According to a still further preferred embodiment, greater than 50% is conserved, advantageously greater than 55%, even better greater than 60% and most preferred greater than 65%. According to an even further preferred embodiment, greater than 70% is conserved, advantageously greater than 75%, even better greater than 80% by weight and most preferred greater than 85%.

The processing steps include heat-treating (e.g., roasting, infra-red heating, etc.), drying, chemical treatments, etc. Preferably, the treatment steps develop chocolate flavor without significantly reducing the cocoa polyphenols content of the feedstock thereof to form heat-treated cocoa beans.

According to one embodiment of the invention the step of treating the cocoa beans comprises heat-treating the cocoa beans at an elevated temperature for a time sufficient to develop chocolate flavor while conserving a significant amount of the cocoa polyphenols content thereof to form heat-treated cocoa beans.

The heat-treating includes roasting, infra-red heating, drying at elevated temperatures and combinations thereof.

According to one embodiment of the invention, the heating of the cocoa bean is to an IBT (internal bean temperature) greater than 120° C. for at least 1 minute and the content of cocoa polyphenols in the heat-treated beans is at least 75% by weight (fullfat) of the cocoa polyphenols content in the pre-treated cocoa beans, advantageously greater than 80% by weight, more desirable greater than 85% by weight, even better greater than 90% by weight and most preferred greater than 95% by weight.

According to another embodiment of the invention, the heating of the cocoa bean is to an IBT (internal bean temperature) above 140° C. for at least 1 minute and the content of cocoa polyphenols in the heat-treated beans is at least 60% (fullfat) by weight of the cocoa polyphenols content in the pre-treated cocoa beans, advantageously greater than 65% by weight, more desirable greater than 70%, even better greater than 75% and most preferred greater than 80%.

According to yet another embodiment of the invention, the heating of the cocoa bean is to an IBT (internal bean temperature) above 160° C. for at least 1 minute and the content of cocoa polyphenols in the heat-treated beans is at least 40% by weight (fullfat) of the cocoa polyphenols content in the pre-treated cocoa beans, advantageously greater than 45%, more desirable greater than 50% by weight, even better greater than 55% by weight and most preferred greater than 60%.

According to a still further embodiment of the invention, the heating of the cocoa bean is to an IBT (internal bean temperature) above 120° C. for at least 1 minute and the content of cocoa polyphenol pentamer (fullfat) in the heat-treated beans is at least 60% by weight of the cocoa polyphenol pentamer content in the pre-treated cocoa beans, advantageously greater than 65%, more desirable greater than 70%, even better greater than 75% and most preferred greater than 80%.

According to another embodiment of the invention, the heating of the cocoa bean is to an IBT (internal bean temperature) above 140° C. for at least 1 minute and the content of cocoa polyphenol pentamer (fullfat) in the heat-treated beans is at least 25% by weight of the cocoa polyphenol pentamer content in the pre-treated cocoa beans, advantageously greater than 30%, more desirable greater than 35%, even better greater than 40% and most preferred greater than 50%.

According to another embodiment of the invention, the heating of the cocoa bean is to an IBT (internal bean temperature) above 160° C. for at least 1 minute and the content of cocoa polyphenol pentamer (fullfat) in the heat-treated beans is at least 15% by weight of the cocoa polyphenol pentamer content in the pre-treated cocoa beans, advantageously greater than 20%, more desirable greater than 25%, even better greater than 30% and most preferred greater than 35%.

Roasting comprises applying external heat to the cocoa bean or nib by a combination of conduction and convection.

With conventional roasting conditions, moisture and volatile substances diffuse from the inner parts of the nib pieces.

According to one embodiment of the invention, roasting is preferably conducted at an internal bean temperature of from 95 to 160° C. for from 30 seconds to 5 hours, advantageously from 95 to 150° C. for from 1 minute to 3 hours, even better from 95 to 140° C. for from 1 minute to 1 hour and most preferred from 95 to 120° C. for from 1 minute to 1 hour.

Infra-red heating comprises applying infra-red heat so that the shells of the beans are rapidly heated. The shells dry, expand and loosen themselves from the nibs.

Preferably, the infra-red heating is conducted at an internal bean temperature of from 95 to 135° C. for from 1 to 5 minutes, advantageously from 95 to 125° C., even better from 95 to 115° C. and most preferred from about 95–110° C.

Preferably, the infra-red heating step is for a period of time less than 8 minutes, advantageously less than 7 minutes, even better less than 6 minutes and most preferred less than 5 minutes. According to a preferred embodiment, the period of time is less than 4 minutes, advantageously less than 3 minutes, even better less than 2 minutes and most preferably less than 1 minute.

According to one embodiment, the treating comprises drying the cocoa beans to form dried cocoa beans. The drying may be at ambient temperature or at an elevated temperature, preferably for a time and to an extent sufficient to develop chocolate flavor while conserving a significant amount of the cocoa polyphenols content thereof. The drying typically reduces the moisture of the cocoa bean to less than 7% by weight. Preferably, the drying decreases the moisture content of the cocoa bean to less than 4% by weight, advantageously to less than 3% by weight, even better to less than 2% by weight and most preferred to less than 1% by weight.

This embodiment of the invention may further comprise the step of producing chocolate liquor containing an enhanced content of cocoa polyphenols from the dried cocoa beans. The chocolate liquor may be produced by conventional grinding methods. Preferably, the chocolate liquor is cooled during grinding to reduce further losses of cocoa polyphenols.

According to another embodiment, the cocoa beans are raw freshly harvested cocoa beans containing a cocoa polyphenols content and the treating comprises:
  (i) at least partially fermenting the raw freshly harvested cocoa beans to form at least partially fermented cocoa beans; and
  (ii) heat-treating the at least partially fermented cocoa beans at an elevated temperature for a time sufficient to develop chocolate flavor while conserving a significant amount of the cocoa polyphenols content thereof to form heat-treated cocoa beans.

Preferably, the cocoa beans are raw freshly harvested cocoa beans having a fermentation factor less than about 125.

According to another embodiment, the treating comprises:
  (i) drying cocoa beans containing a cocoa polyphenols content to form dried cocoa beans; and
  (ii) infra-red heating the dried cocoa beans at an elevated temperature for a time sufficient to form infra-red heated cocoa beans while conserving a significant amount of the cocoa polyphenols content thereof.

According to yet another embodiment, the cocoa beans have shells and the treating comprises:
  (i) infra-red heating the cocoa beans at an elevated temperature for a time sufficient to loosen the shells while conserving a significant amount of the cocoa polyphenols content thereof to form infra-red heated cocoa beans; and
  (ii) roasting the infra-red heated cocoa beans at an elevated temperature for a time sufficient to develop chocolate flavor while further conserving a significant amount of the cocoa polyphenols content thereof to form roasted cocoa beans.

According to a still further embodiment, the treating comprises:
  (i) infra-red heating the cocoa beans at an elevated temperature for a time sufficient to reduce their moisture to less than 5% by weight while conserving a significant amount of the cocoa polyphenols content thereof to form infra-red heated cocoa beans; and
  (ii) roasting the infra-red heated cocoa beans at an elevated temperature for a time sufficient to develop chocolate flavor while further conserving a significant amount of the cocoa polyphenols content thereof to form roasted cocoa beans.

According to another embodiment of the invention, the treating comprises:
  (i) drying cocoa beans containing a cocoa polyphenols content to form dried cocoa beans;
  (ii) infra-red heating the dried cocoa beans at an elevated temperature for a time sufficient to develop chocolate flavor while conserving a significant amount of the cocoa polyphenols content thereof to form infra-red heated cocoa beans; and
  (iii) roasting the infra-red heated cocoa beans at an elevated temperature for a time sufficient to further-develop chocolate flavor while further conserving a significant amount of the cocoa polyphenols content thereof to form roasted cocoa beans.

Figure 4:
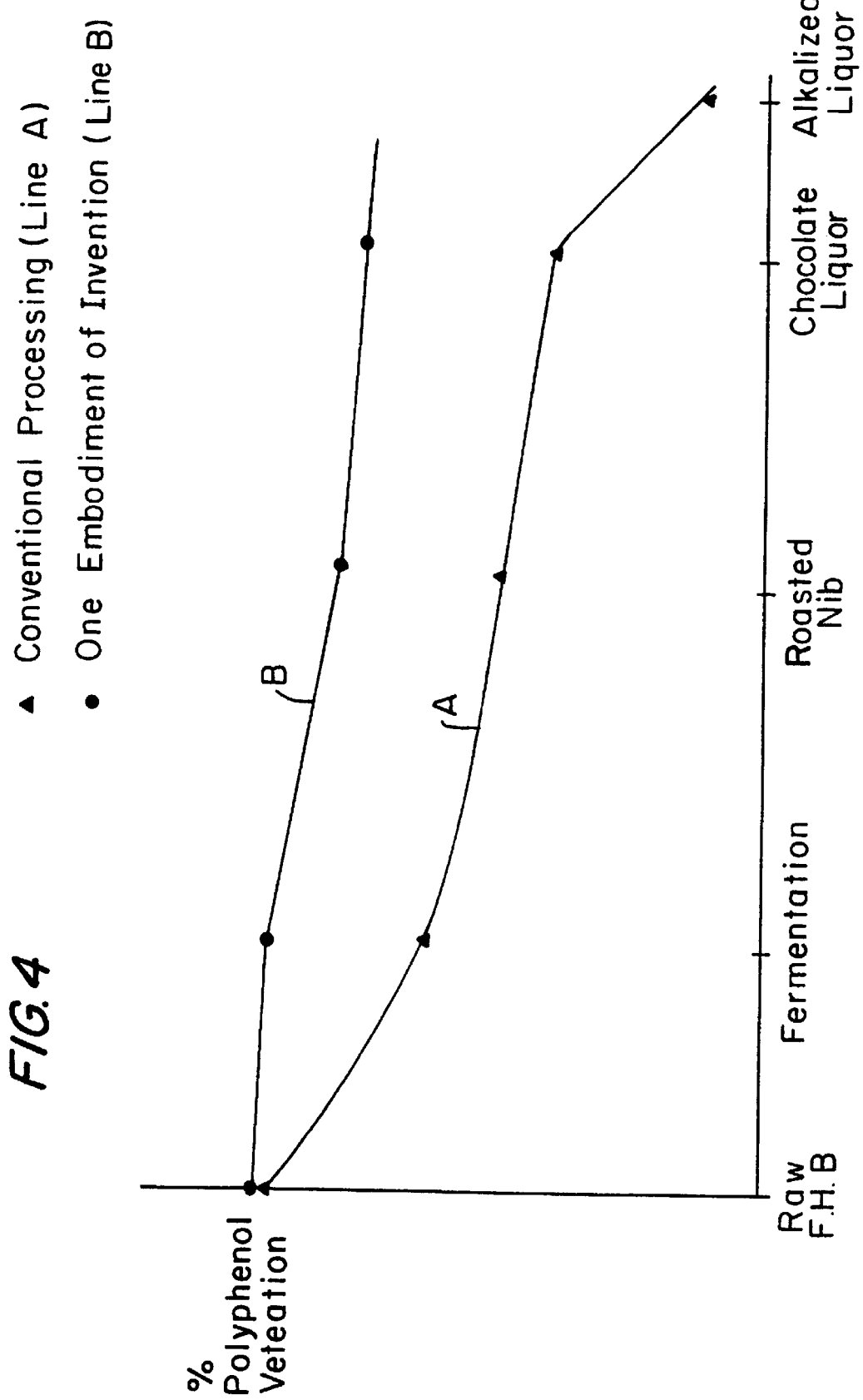
FIG. 4 is a graphical representation illustrating the levels of total cocoa polyphenols present in the cocoa bean or portion thereof during conventional chocolate liquor processing (line A) and during processing according to one embodiment of the invention (line B)

Surprisingly, it has been discovered that the polyphenols content of the cocoa bean may be maintained or conserved by controlling the treatment of the beans. Referring to FIG. 4, a graphical representation illustrates the levels of total cocoa polyphenols present in the cocoa bean or portion thereof during conventional chocolate liquor processing (line A) and processing according to one embodiment of the invention (line B). As can be seen by the graph, an initial loss in polyphenols content occurs during fermentation, additional loss occurs during roasting and further loss occurs during liquor, nib, cake or powder alkalizing (during the manufacture of chocolate).

According to the invention, the cocoa polyphenols content of the cocoa component produced is from 25 to 100% by weight of the cocoa polyphenols content in the fair average quality cocoa beans, advantageously from 35 to 100% by weight, more desirable from 45 to 100% by weight, even better from 55 to 100% by weight and more preferred from 65 to 100% by weight.

The invention permits the retention of higher levels of the cocoa polyphenols content not only with respect to the fair average quality cocoa beans, but also with respect to raw freshly harvested cocoa beans. Using the method of the invention, the cocoa polyphenols content of the cocoa component produced is from 5 to 100% by weight of the cocoa polyphenols content in the raw freshly harvested cocoa beans, advantageously from 10 to 75% by weight of the cocoa polyphenols content in the raw freshly harvested cocoa beans, preferably from 15 to 50% by weight, even better from 20 to 45% by weight and most preferred greater than 30% by weight.

According to one embodiment, the cocoa polyphenols content of the infra-red heated cocoa beans is at least 55% by weight of the cocoa polyphenols content of the fair average quality cocoa beans, preferably at least 65%, advantageously at least 75%, even better at least 85% and most preferred at least 95%.

The cocoa polyphenol pentamer content of the infra-red heated cocoa beans may be at least 30% by weight of the cocoa polyphenol pentamer content of the fair average quality cocoa beans, preferably at least 35%, advantageously at least 40%, even better at least 45% and most preferred at least 50%.

When infra-red heating and roasting steps are used in combination, the cocoa polyphenols content of the roasted cocoa beans is preferably at least 75% by weight of the cocoa polyphenols content of the infra-red heated cocoa beans, advantageously at least 80%, even better at least 85% and most preferred at least 90%. Alternatively, the cocoa polyphenol pentamer content of the roasted cocoa beans is at least 40% by weight of the cocoa polyphenol pentamer content of the infra-red heated cocoa beans, advantageously at least 50%, even better at least 60% and most preferred at least 70%.

One preferred aspect of the invention relates to the production of chocolate liquors containing enhanced levels of cocoa polyphenols. Therefore, the cocoa components produced by the inventive methods preferably include chocolate liquor.

Accordingly, one embodiment of the invention relates to a method for the production of chocolate liquor having an enhanced content of cocoa polyphenols comprising the steps of:

(a) treating cocoa beans, containing cocoa polyphenols, while conserving a significant amount of the cocoa polyphenols content thereof to form treated cocoa beans; and (b) producing chocolate liquor containing an enhanced content of cocoa polyphenols from the treated cocoa beans.

Preferably, the cocoa polyphenols content in the chocolate liquor is at least 65% by weight of the cocoa polyphenols content of the cocoa beans, advantageously at least 75%, even better at least 85% and most preferred greater than 90%.

Preferably, the cocoa polyphenol pentamer content in the chocolate liquor is at least 45% by weight of the cocoa polyphenol pentamer content of the cocoa beans, advantageously at least 55%, even better at least 60% and most preferred greater than 75%.

The invention also relates to the treatment of cocoa components, particularly chocolate liquors, to provide a cocoa component having high levels of cocoa polyphenols with acceptable aroma/flavor characteristics. The treatment includes the removal of undesirable or off flavors present in a cocoa component. The flavor may also be modified using additives or the blending of cocoa components having varying levels of cocoa polyphenols and varying degrees of aroma/flavor.

The chocolate liquor or cocoa component may be subsequently heat-treated to remove any undesirable or off flavors.

The subsequent heat-treating is preferably to a temperature between 65 and 140° C. for from 5 minutes to 24 hours, advantageously between about 75 and 130° C. for from 5 minutes to 2 hours, even better between about 85 and 120° C. for from 5 minutes to 1 hour and most preferred between about 95 and 110° C. for from 5 minutes to 30 minutes.

Figure 5:
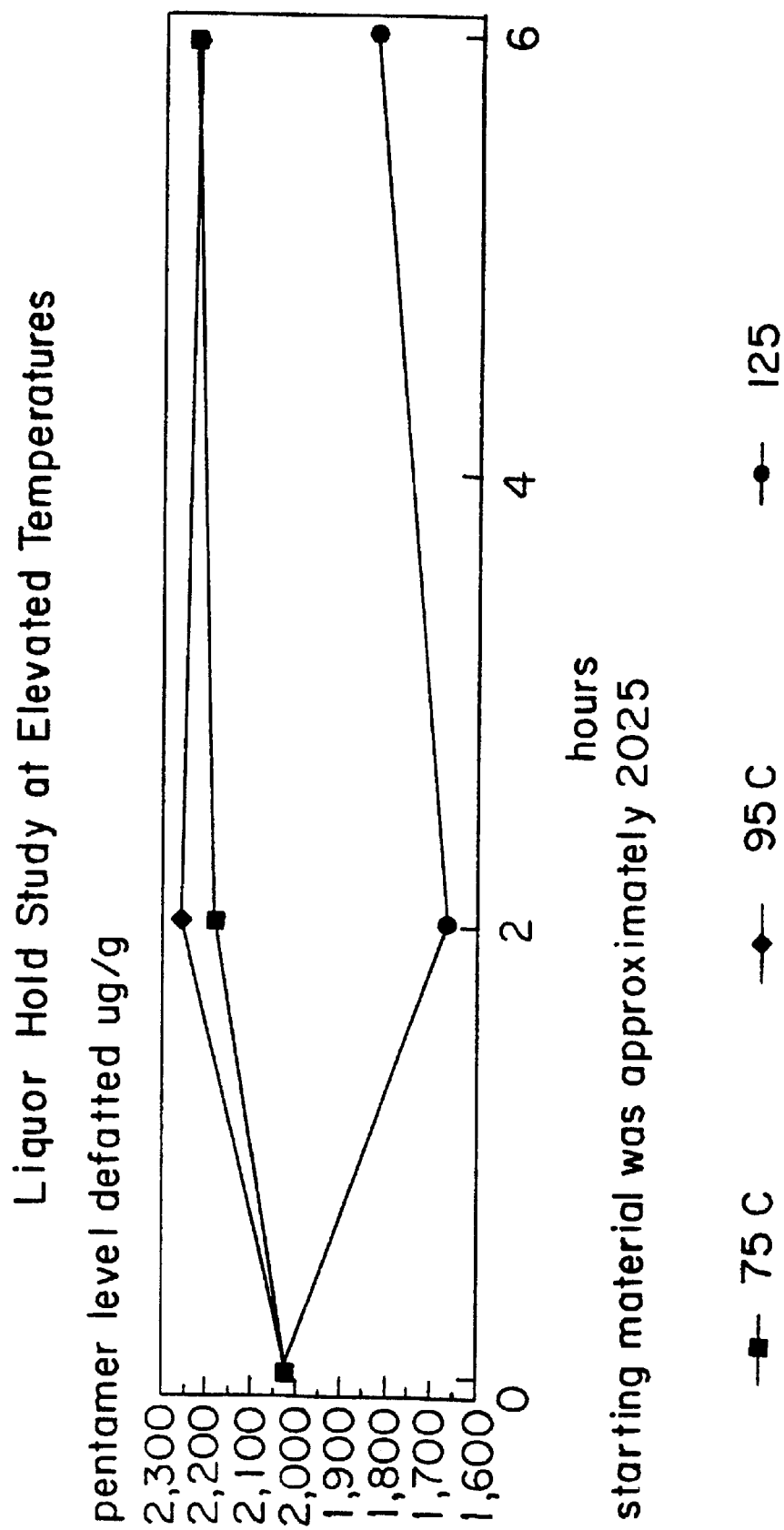
FIG. 5 is a graphical representation of cocoa polyphenols level/heating temperature/heating time relationship for chocolate liquor samples heat treated at three different temperatures, wherein the vertical axis represents the level of cocoa polyphenol pentamer (ug/g) from defatted chocolate liquors and the horizational axis is the time of heat treatment.

Preferably, the subsequent heat-treating includes agitation to facilitate the removal of off-flavors. The heating may be under a vacuum to assist in the removal of off-flavors, preferably wherein the pressure is less than 26 inches (660 mm) mercury. The chocolate liquor or cocoa component may also be aerated during the heat-treatment. FIG. 5 illustrates the effect of different heat treatment temperatures (75° C., 95° C., 125° C.) on pentamer level vs. time of heating in a chocolate liquor. FIG. 5 shows that long treatments at temperatures greater than 100° C. should be avoided.

According to one embodiment, the liquor or cocoa component is subsequently directly heated with steam.

Preferably, the cocoa polyphenols content of the chocolate liquor is at least 55% by weight of the cocoa polyphenols content of the cocoa beans, advantageously at least 65%, even better at least 75% and most preferred at least 85%.

Preferably, the cocoa polyphenol pentamer content of the chocolate liquor is at least 45% by weight of the cocoa polyphenol pentamer content of the cocoa beans, advantageously at least 55%, even better at least 65% and most preferred at least 75%.

Another aspect of the invention relates to methods of making chocolate liquors without the use of an alkalization step and/or without the use of a conventional roasting step.

One embodiment of the invention relates to methods of making a non-alkalized chocolate liquor comprising the steps of:

(a) heating cocoa beans using infra-red radiation; and (b) producing a chocolate liquor from the heated cocoa beans;

wherein the chocolate liquor is not subsequently alkalized.

Another embodiment of the invention relates to a method of making a chocolate liquor comprising the steps of:

(a) heating cocoa beans using infra-red radiation to loosen their shell; and (b) producing a chocolate liquor from the heated cocoa beans without a subsequent heating step.

According to this embodiment of the invention, the heating is achieved by the use of an infra-red heater. A suitable infra-red heater is manufactured by Micronizer company (U.K.) Ltd. The infra-red heating is performed at elevated temperatures as compared to conventional processing conditions to not only assist in removing the strongly adhering shells from the cocoa nibs, but also to lightly roast the raw beans. The level of thermal processing achieved with the infra-red heating eliminates the need for a conventional bean roaster. The infra-red heating puffs and loosens the shells from the beans to facilitate removal in the winnowing process. Preferably, the infra-red heating is performed at elevated temperatures to give a sufficient roast to the raw beans and thereby eliminate the need for an additional bean roaster. The elimination of the conventional bean roasting step greatly simplifies and reduces the cost of the method or process.

Preferably, the heating reduces the cocoa bean moisture content to less than 7% by weight, preferably less than 5% by weight, advantageously less than 4%, even better less than 3%, and most preferred less than 2%.

As set forth above, the cocoa polyphenols content of the cocoa beans decreases dramatically during fermentation. One aspect of the invention relates to the use of underfermented or unfermented cocoa beans in the production of the cocoa component. Preferably, the cocoa beans have a fermentation factor less than 375, advantageously less than 350, even better less than 325, and most preferred less than 300.

According to yet another embodiment, highly underfermented cocoa beans are used. Preferably, the cocoa beans have a fermentation factor less than 275, advantageously less than 250, even better less than 225, and most preferred less than 200. Cocoa beans having a fermentation factor less than 150 or even unfermented beans (i.e., a fermentation factor of about 100) may also be used.

According to another aspect of the invention, the method comprises the step of at least partially fermenting raw freshly harvested cocoa beans containing a cocoa polyphenols content to form at least partially fermented cocoa beans and subsequently treating the at least partially fermented cocoa beans. Preferably, the at least partially fermented cocoa beans have a fermentation factor less than 375, even better less than 200 and most preferred less than 150.

Another aspect of the invention relates to methods for the commercial production of cocoa polyphenols, for use as an edible, ingestible or pharmaceutical component, from cocoa beans comprising the steps of:

(a) processing cocoa beans to separate cocoa butter from cocoa solids; and (b) extracting cocoa polyphenols from the cocoa solids, wherein the processing comprises the steps of pressing, microwave assisted extraction (see U.S. Pat. No. 5,002,784 to Pare et al.), solvent extraction or combinations thereof.

Another embodiment of the invention relates to methods for the commercial production of cocoa polyphenols from cocoa beans comprising the sequential steps of:

(a) extracting cocoa polyphenols from the cocoa beans; and (b) separating a cocoa component from cocoa shell.

According to one preferred embodiment, the cocoa beans are underfermented to enhance the amount of cocoa polyphenols. Preferably, the cocoa beans have a fermentation factor less than 375, even better less than 350 and most preferred less than 325.

C. Cocoa Components having Enhanced Levels of Cocoa Polyphenols

1. Chocolate Liquors

Using the above-described methods, chocolate liquors having enhanced levels of cocoa polyphenols are obtained.

When characterizing an inventive product by relating the amount of cocoa polyphenols per gram ingredient in the inventive product, that ingredient does not necessarily contain the cocoa polyphenols, but rather it is the product that contains the cocoa polyphenols.

One embodiment relates to a chocolate liquor produced from fair average quality cocoa beans having a fermentation factor greater than 375, the chocolate liquor containing at least 5500 $\mu$g, preferably at least 6000 $\mu$g, advantageously at least 7000 $\mu$g, even better at least 8000 $\mu$g and most preferred at least 9000 $\mu$g cocoa polyphenols per gram chocolate liquor. Preferably, the chocolate liquor contains at least 500 $\mu$g cocoa polyphenols pentamer per gram chocolate liquor, advantageously at least 600 $\mu$g, even better at least 700 $\mu$g and most preferred at least 800 $\mu$g per gram chocolate liquor.

Another embodiment relates to a chocolate liquor produced from cocoa beans having a fermentation factor less than 375, the chocolate liquor containing at least 16,500 $\mu$g cocoa polyphenols per gram chocolate liquor, advantageously at least 20,000 $\mu$g, even better at least 25,000 $\mu$g and most preferred at least 30,000 $\mu$g cocoa polyphenols per gram chocolate liquor. Preferably, the chocolate liquor contains at least 1,500 $\mu$g cocoa polyphenol pentamer per gram chocolate liquor, more preferably at least 1,750 $\mu$g, advantageously at least 2,000 $\mu$g, even better at least 2,500 $\mu$g and most preferred at least 3,000 $\mu$g per gram chocolate liquor.

Yet another embodiment relates to a chocolate liquor comprising cocoa butter, partially defatted cocoa solids and cocoa polyphenols, wherein the partially defatted cocoa solids contain at least 33,000 $\mu$g cocoa polyphenols per gram defatted cocoa solids, advantageously at least 40,000 $\mu$g, even better at least 50,000 $\mu$g and most preferred at least 60,000 $\mu$g cocoa polyphenols per gram defatted cocoa solids. Preferably, the chocolate liquor contains at least 3,000 $\mu$g cocoa polyphenol pentamer per gram defatted cocoa solids, preferably at least 3,500 $\mu$g, advantageously at least 4,000 $\mu$g, even better at least 5,000 $\mu$g and most preferred at least 6,000 $\mu$g per gram per gram defatted cocoa solids. Preferably, the chocolate liquor is derived substantially from underfermented cocoa beans having a fermentation factor less than 375, advantageously less than 350, even better less than 300 and most preferred less than 250.

2. Partially Defatted Cocoa Solids Having Enhanced Levels of Cocoa Polyphenols

One embodiment of the invention relates to partially defatted cocoa solids having elevated levels of cocoa polyphenols. Preferably, the cocoa solids contain at least 33,000 $\mu$g cocoa polyphenols per gram defatted cocoa solids, advantageously at least 40,000 $\mu$g, even better at least 50,000 $\mu$g and most preferred at least 60,000 $\mu$g cocoa polyphenols per gram defatted cocoa solids. Preferably, the cocoa solids contain at least 3,000 $\mu$g cocoa polyphenol pentamer per gram defatted cocoa solids, advantageously at least 3,500 $\mu$g, even better at least 4,000 $\mu$g, more preferably at least 5,000 $\mu$g, and most preferred at least 6,000 $\mu$g per gram defatted cocoa solids.

Preferably, the partially defatted cocoa solids are derived substantially from underfermented cocoa beans having a fermentation factor less than 375, advantageously less than 350, even better less than 300 and most preferred less than 250.

The partially defatted cocoa solids may be in cake or powder form.

D. Methods of Making Novel Edible Products Containing Cocoa Polyphenols

One embodiment of the invention relates to a method of making an edible product containing a cocoa component having an enhanced content of cocoa polyphenols comprising the steps of:

(a) treating cocoa beans containing a cocoa polyphenols content while conserving a significant amount of the cocoa polyphenols content thereof to form treated cocoa beans;

(b) producing the cocoa component from the treated cocoa beans; and (c) including the component in the edible product.

The cocoa component may be selected from the group consisting of cocoa nib, chocolate liquor, partially or fully defatted cocoa solids, cocoa polyphenol extract and mixtures thereof.

Another embodiment of the invention relates to a method of making an edible product having an enhanced content of cocoa polyphenols comprising adding a cocoa polyphenol additive or a derivative thereof. The cocoa polyphenol additive may be mixed with the other ingredients of the edible composition at any time during the processing or added to the edible product after processing (i.e., spraying cocoa polyphenols onto the product).

Preferably, the cocoa polyphenol additive is an extract from cocoa beans or a cocoa component thereof. The cocoa polyphenol additive may either be substantially pure (e.g., greater than 95% by weight pure) or mixed with other components.

The cocoa polyphenol additive may either be synthetic or derived naturally.

E. Methods of Making Chocolates Having Enhanced Levels of Cocoa Polyphenols

The cocoa components having enhanced levels of cocoa polyphenols may be used to form chocolates by conventional methods.

One aspect of the invention relates to the manipulation of the flavor of the final chocolate product. The use of a cocoa component having higher levels of cocoa polyphenols typically affects the flavor/aroma of the final product. The higher cocoa polyphenols content is typically associated with a bitter, astringent flavor. Various methods may be used to reduce the bitter, astringent note in the cocoa component. According to one embodiment of the invention, flavor additives are used to mask or reduce the flavor/aroma of the product.

This aspect of the invention relates to the use of at least two chocolate liquors having varying levels of cocoa polyphenols. For example, a first chocolate liquor derived from fermented cocoa beans (having a low cocoa polyphenols level) and a second chocolate liquor derived from underfermented beans (having a higher cocoa polyphenols level) are advantageously used. The use of such a blend allows for the production of a chocolate having strong flavor/aroma characteristics as well as enhanced levels of cocoa polyphenols.

One preferred aspect of the invention uses a two step heat treatment (split hot conching) in the processing of the chocolate. The first chocolate liquor having the lower levels of cocoa polyphenols is subjected to a heat treatment at elevated temperatures to develop flavor. Since the first chocolate liquor has lower levels of cocoa polyphenols, it may be subjected to the higher temperature. The heat treated first chocolate liquor is subsequently combined with the second chocolate liquor having the enhanced levels of cocoa polyphenols and further processed into the final chocolate product. Using this method, the chocolate liquor containing the enhanced levels of cocoa polyphenols is not necessarily exposed to the elevated temperatures, thereby preventing a significant reduction in the polyphenols.

One embodiment of the invention relates to a method of making a chocolate comprising the steps of:

(a) combining chocolate liquor from cocoa beans having a fermentation factor greater than 375 with at least one additive selected from the group consisting of:
 (i) at least one fat;
 (ii) at least one sugar;
 (iii) milk solids; and
 (iv) mixtures thereof;
to form an initial mixture;

(b) heating the initial mixture to a temperature less than about 200° C. for 5 minutes to 24 hours;

(c) cooling the initial mixture;

(d) combining the initial mixture with a second chocolate liquor from cocoa beans having a fermentation factor less than 375 and any remaining ingredients to form a secondary mixture; and (e) conching the secondary mixture.

Preferably, the milk solids are in an amount greater than or equal to 12% by weight.

Accordingly, one embodiment of the invention relates to a method of making a chocolate composition comprising the steps of:

(a) combining a first chocolate liquor from cocoa beans having a fermentation factor greater than 375, cocoa butter and sugar to form an initial mixture;

(b) heating the initial mixture to a temperature less than about 200° C. for 5 minutes to 24 hours;

(c) cooling the initial mixture;

(d) combining the initial mixture with a second chocolate liquor from cocoa beans having a fermentation factor less than 375 and any remaining ingredients to form a secondary mixture; and (e) conching the secondary mixture.

Another embodiment of the invention relates to a method comprising the steps of:

(a) combining a chocolate liquor high in cocoa polyphenols (preferably having a fermentation factor less than 375) with at least one ingredient and heating to a temperature preferably less than 140° C., more preferably less than 100° C. for a period of time between 5 minutes to 24 hours;

(b) cooling the mixture;

(c) combining the remaining ingredients; and (d) conching the second mixture.

Another embodiment of the invention relates to a method comprising the steps of:

(a) heating a chocolate liquor high in cocoa polyphenols, preferably a fermentation factor less than 375, to a temperature preferably less than 140° C. for 5 minutes to 24 hours;

(b) combining the heated chocolate liquor with other chocolate ingredients; and (c) conching.

Another embodiment of the invention relates to a method for the production of a chocolate comprising the steps of:

(a) heating a first chocolate liquor from cocoa beans having a fermentation factor greater than 375 and any remaining ingredients to a temperature less than about 200° C. for 5 minutes to 24 hours;

(b) cooling the first chocolate liquor;

(c) combining the cooled first chocolate liquor with a second chocolate liquor from cocoa beans having a fermentation factor less than 375 to produce a secondary mixture; and (d) conching the secondary mixture.

Preferably, the fermentation factor of the second chocolate liquor is less then 350, advantageously less than 300, even better less than 275, and most preferred less than 250. According to a preferred embodiment, the fermentation factor of the second chocolate liquor is less than 225, advantageously less than 200, even better less than 150, and most preferred less than 125.

F. Methods of Producing Cocoa Butter and Partially Defatted Cocoa Solids

Yet another aspect of the invention relates to the production of cocoa butter without necessarily the concomitant conservation of polyphenols. This aspect of the invention relates to a method for processing cocoa beans to make cocoa butter and cocoa powder. In particular, the method comprises the steps of cleaning and preparing the cocoa beans, infra-red heating of the cocoa beans, shell removal, screw pressing of nibs to extract the cocoa butter from the cocoa solids, milling the natural cocoa cake and/or alkalizing the natural cocoa cake and milling the alkalized cake. The method delivers both natural cocoa butter and powders (natural and/or value added alkalized powders) from the screw pressed nibs. The invention provides a method for processing cocoa beans to produce cocoa butter and cocoa powder that requires lower total assets since bean roasting and liquor milling are not required and a significantly less complex process with respect to maintenance, energy and labor.

One embodiment of the invention relates to a method of producing cocoa solids and cocoa butter comprising the steps of:

(a) heating cocoa beans having an outer cocoa shell and inner cocoa nib using infra-red radiation to an internal temperature greater than 115° C.;

(b) separating the shell from the nib; and (c) subsequently extracting the cocoa butter by screw pressing the nibs.

One preferred embodiment comprises the steps of (a) air fluidized bed density separation to clean the cocoa beans, (b) infra-red heating of the cleaned cocoa beans at elevated temperatures exceeding 115° C., (c) shell removal, (d) screw pressing of the nibs to produce cocoa butter and cocoa cake, (e) alkalizing the cocoa cake, and (f) air-classified hammer milling of the natural and/or alkalized cocoa cake to produce cocoa powder.

A still further embodiment of the invention relates to a method of producing cocoa butter and cocoa cake solids comprising the steps of:

(a) cleaning a mixture comprising cocoa beans to separate cocoa beans from non-cocoa solids;

(b) heating cocoa beans having an outer cocoa shell and an inner cocoa nib using infra-red radiation to an internal temperature greater than 125° C.;

(c) removing the outer cocoa shell from the nib;

(d) screw pressing the nibs to extract the cocoa butter leaving cocoa cake solids; and (e) cooling the cocoa butter to room temperature.

Preferably, the heating is to an IBT (internal bean temperature) greater than 120° C., advantageously greater than 125° C., even better greater than 130° C. and most preferred greater than 135° C. The heating preferably results in cocoa beans having a moisture content of about 3 percent by weight.

Another preferred embodiment of the invention relates to the use of infra-red heating of the cocoa beans at temperatures up to or exceeding 125° C. to result in a light roast and loosening of the shell and subsequently using a screw press to extract cocoa butter from the lightly roasted bean.

According to one embodiment, the surface temperature of the bean is heated from about 160 to about 170° C., while the internal temperature of the bean is preferably heated to about 130 to about 140° C. The resultant nibs should have a reduced moisture content of about 3% prior to pressing. The time of exposure to the infra-red heating is preferably about 0.5 to 4 minutes, however this may be varied depending on the amount of moisture in the nib. The bean height through the infra-red heater should be about two beans high.

According to another preferred embodiment of the invention, the infra-red heated beans are cooled to ambient temperature after the infra-red heating step. This is to avoid continued loss of moisture resulting from the infra-red heating prior to the screw pressing step. The nibs subjected to the screw press preferably have a moisture content of about 3% with a normal operating moisture range of between 2–6%.

The cocoa beans may be cooled to room temperature after the heating and subsequently pre-heated to a temperature between about 80° C. and about 90° C. prior to the step of screw pressing.

According to one preferred embodiment, prior to the step of heating, the beans are cleaned using a fluidized-bed separator. Preferably, the cocoa beans are subjected to a pre-cleaning step prior to cleaning in the air fluidized bed density separator.

Preferably, the step of separating includes a winnowing step to separate the shell from cocoa nibs prior to the pressing step.

Preferably, the screw pressing forms cocoa butter and cocoa cake solids. According to one embodiment, the cocoa cake solids are subsequently treated by alkalizing to form alkalized cocoa cake solids. The alkalized cocoa cake solids may be subsequently milled to produce fine cocoa powders.

Yet another embodiment of the invention relates to a method of winnowing cocoa beans comprising separating shells from an inner bean portion of the cocoa beans using an air fluidized-bed density separator. Preferably, the air fluidized-bed density separator comprises a means for homogenizing material introduced therein and at least one vibratory screen, advantageously the air fluidized-bed density separator comprises three vibratory screens. Surprisingly, greater than 99.5% of the shells are removed by the inventive method, preferably wherein less than 1.1% of the inner bean portion by weight are removed with the shell.

G. Novel Edible Products Containing Cocoa Polyphenols

Using the methods described above, novel edible compositions containing cocoa polyphenols, particularly enhanced levels of cocoa polyphenols, are made. The novel compositions are distinguishable from conventional compositions either because (1) the inventive compositions contain elevated levels of cocoa polyphenols relative to comparative conventional product (i.e., chocolates, chocolate-flavored confections, etc.) and/or (2) the inventive compositions contain cocoa polyphenols in contrast to the comparative composition which does not contain cocoa polyphenols (i.e., rice cakes, edible compositions without chocolate flavor/aroma, etc.).

1. Standard of Identity Chocolate one embodiment of the invention relates to a standard of identity chocolate comprising at least 3,600 $\mu$g cocoa polyphenol per gram chocolate, preferably at least 4,000 $\mu$g, advantageously at least 4,500 $\mu$g, even better at least 5,000 $\mu$g, and most preferred at least 5,500 $\mu$g cocoa polyphenols per gram chocolate. According to one preferred embodiment, the standard of identity chocolate contains least 6,000 $\mu$g cocoa polyphenols per gram chocolate, advantageously at least 6,500 $\mu$g, even better at least 7,000 $\mu$g, and most preferred at least 8,000 $\mu$g cocoa polyphenols per gram chocolate.

Another embodiment of the invention relates to a standard of identity chocolate comprising at least 200 $\mu$g cocoa polyphenol pentamer per gram chocolate, advantageously at least 225 $\mu$g, even better at least 275 $\mu$g, and most preferred at least 300 $\mu$g cocoa polyphenol pentamer per gram chocolate. According to one preferred embodiment, the standard of identity chocolate contains at least 325 $\mu$g cocoa polyphenol pentamer per gram chocolate, advantageously at least 350 $\mu$g, even better at least 400 $\mu$g, and most preferred at least 450 $\mu$g cocoa polyphenol pentamer per gram chocolate.

2. Standard of Identity Chocolate Containing Milk Solids

Yet another embodiment of the invention relates to a standard of identity chocolate containing milk solids and comprising at least 1,000 µg cocoa polyphenols per gram chocolate, advantageously at least 1,250 µg, even better at least 1,500 µg, and most preferred at least 2,000 µg cocoa polyphenols per gram chocolate. According to one preferred embodiment, the standard of identity chocolate contains at least 2,500 µg cocoa polyphenols per gram chocolate, advantageously at least 3,000 µg, even better at least 4,000 µg, and most preferred at least 5,000 µg cocoa polyphenols per gram chocolate.

Another embodiment of the invention relates to a standard of identity chocolate containing milk solids and comprising at least 85 µg cocoa polyphenol pentamer per gram chocolate, advantageously at least 90 µg, even better at least 100 µg, and most preferred at least 125 µg cocoa polyphenol pentamer per gram chocolate. According to one preferred embodiment, the standard of identity chocolate contains at least 150 µg cocoa polyphenol pentamer per gram chocolate, advantageously at least 175 µg, even better at least 200 µg, and most preferred at least 250 µg cocoa polyphenol pentamer per gram chocolate.

Preferably the standard of identity milk chocolate contains milk solids in an amount greater than or equal to 12% by weight.

3. Chocolates Comprising a Cocoa Component

Another embodiment of the invention relates to chocolates comprising a cocoa component, wherein the chocolate contains at least 3,600 µg, preferably at least 4,000 µg cocoa polyphenols per gram chocolate, advantageously at least 4,500 µg, even better at least 5,000 µg, and most preferred at least 5,500 µg cocoa polyphenols per gram chocolate. According to one preferred embodiment, the chocolate contains least 6,000 µg cocoa polyphenols per gram chocolate, advantageously at least 6,500 µg, even better at least 7,000 µg, and most preferred at least 8,000 µg cocoa polyphenols per gram chocolate.

Another embodiment of the invention relates to a chocolate comprising at least 200 µg cocoa polyphenol pentamer per gram chocolate, advantageously at least 225 µg, even better at least 275 µg, and most preferred at least 300 µg cocoa polyphenol pentamer per gram chocolate. According to one preferred embodiment, the chocolate contains at least 325 µg cocoa polyphenol pentamer per gram chocolate, advantageously at least 350 µg, even better at least 400 µg, and most preferred at least 450 µg cocoa polyphenol pentamer per gram chocolate.

4. Chocolates Comprising Milk Solids

Yet another embodiment of the invention relates to a chocolate containing milk solids (e.g., a milk chocolate) and comprising at least 1,000 µg cocoa polyphenols per gram chocolate, advantageously at least 1,250 µg, even better at least 1,500 µg, and most preferred at least 2,000 µg cocoa polyphenols per gram chocolate. According to one preferred embodiment, the chocolate contains at least 2,500 µg cocoa polyphenols per gram chocolate, advantageously at least 3,000 µg, even better at least 4,000 µg, and most preferred at least 5,000 µg cocoa polyphenols per gram chocolate.

Another embodiment of the invention relates to a chocolate containing milk solids and comprising at least 85 µg cocoa polyphenol pentamer per gram chocolate, advantageously at least 90 µg, even better at least 100 µg, and most preferred at least 125 µg cocoa polyphenol pentamer per gram chocolate. According to one preferred embodiment, the chocolate contains at least 150 µg cocoa polyphenol pentamer per gram chocolate, advantageously at least 175 µg, even better at least 200 µg, and most preferred at least 250 µg cocoa polyphenol pentamer per gram chocolate.

Preferably, the chocolate contains milk solids in an amount greater than or equal to 12% by weight.

5. Chocolates Comprising a Cocoa Component

Yet another embodiment of the invention relates to a chocolate comprising a fat phase and a cocoa component containing a cocoa polyphenols content from fair average quality cocoa beans, wherein the cocoa component contains at least 25% of the cocoa polyphenols content of the fair average quality cocoa beans, preferably at least 35%, advantageously at least 50%, even better at least 60% and most preferred at least 75% by weight.

A still further embodiment of the invention relates to a chocolate comprising a fat phase and a cocoa component containing a cocoa polyphenols pentamer content from fair average quality cocoa beans, wherein the cocoa component contains at least 15% of the cocoa polyphenols content of the fair average quality cocoa beans, preferably at least 20%, advantageously at least 25%, even better at least 35% and most preferred at least 50% by weight.

Yet another embodiment of the invention relates to a chocolate comprising a cocoa component and at least one fat, and further containing at least 7,300 µg cocoa polyphenols per gram cocoa component, preferably at least 8,000 µg, advantageously at least 9,000 µg, even better at least 10,000 µg, and most preferred at least 12,000 µg cocoa polyphenols per gram cocoa component.

Another embodiment of the invention relates to a chocolate comprising a cocoa component and at least one fat, and further containing at least 360 µg cocoa polyphenol pentamer per gram cocoa component, preferably at least 480 µg, advantageously at least 600 µg, even better at least 720 µg, and most preferred at least 800 µg cocoa polyphenol pentamer per gram cocoa component.

6. Chocolates Comprising Cocoa Solids

Another embodiment of the invention relates to a chocolate comprising partially defatted cocoa solids and at least one fat, and further containing at least 23,100 µg cocoa polyphenols per gram defatted cocoa solids, preferably at least 24,000 µg, advantageously at least 26,000 µg, even better at least 28,000 µg, and most preferred at least 30,000 µg cocoa polyphenols per gram defatted cocoa solids.

Another embodiment of the invention relates to a chocolate comprising partially defatted cocoa solids and at least one fat, and further containing at least 1,000 µg cocoa polyphenol pentamer per gram defatted cocoa solids, preferably at least 1,200 µg, advantageously at least 1,400 µg, even better at least 1,600 µg, and most preferred at least 1,800 µg cocoa polyphenol pentamer per gram defatted cocoa solids.

Another embodiment of the invention relates to a chocolate comprising partially defatted cocoa solids and at least one fat, and further containing at least 10,500 µg cocoa polyphenols per gram fat, advantageously at least 15,000 µg, even better at least 17,500 µg, and most preferred at least 20,000 µg cocoa polyphenols per gram fat.

Another embodiment of the invention relates to a chocolate comprising partially defatted cocoa solids and at least one fat, and further containing at least 520 µg cocoa polyphenol pentamer per gram fat, advantageously at least 750 µg, even better at least 900 µg, and most preferred at least 1,200 µg cocoa polyphenol pentamer per gram fat.

A still further embodiment of the invention relates to a chocolate comprising cocoa solids and at least one fat, and further containing at least 630 µg cocoa polyphenols per calorie, advantageously at least 750 µg, even better at least 900 µg, and most preferred at least 1,000 µg cocoa polyphenols per calorie.

Another embodiment of the invention relates to a chocolate comprising partially defatted cocoa solids and at least one fat, and further containing at least 32 µg cocoa polyphenol pentamer per calorie, preferably at least 50 µg, advantageously at least 60 µg, even better at least 72 µg, and most preferred at least 100 µg cocoa polyphenol pentamer per calorie.

A still further embodiment of the invention relates to a chocolate comprising partially defatted cocoa solids and at least one fat, and further containing at least 1,200,000 µg cocoa polyphenols per gram emulsifier, advantageously at least 1,500,000 µg, even better at least 1,800,000 µg, and most preferred at least 2,200,000 µg cocoa polyphenols per gram emulsifier.

Another embodiment of the invention relates to a chocolate comprising partially defatted cocoa solids and at least one fat, and further containing at least 58,000 µg cocoa polyphenol pentamer per gram emulsifier, advantageously at least 78,000 µg, even better at least 100,000 µg, and most preferred at least 120,000 µg cocoa polyphenol pentamer per gram emulsifier.

7. Chocolates Comprising Chocolate Liquor

A still further embodiment of the invention relates to a chocolate comprising chocolate liquor and at least one fat, and further containing at least 10,200 µg cocoa polyphenols per gram chocolate liquor, preferably at least 12,000 µg, advantageously at least 14,000 µg, even better at least 16,000 µg, and most preferred at least 18,000 µg cocoa polyphenols per gram chocolate liquor.

Another embodiment of the invention relates to a chocolate comprising chocolate liquor and at least one fat, and further containing at least 500 µg cocoa polyphenol pentamer per gram chocolate liquor, preferably at least 525 µg, advantageously at least 550 µg, even better at least 575 µg, and most preferred at least 600 µg cocoa polyphenol pentamer per gram chocolate liquor.

8. Additional Chocolates

A still further embodiment of the invention relates to a chocolate comprising at least one milk component and at least one fat, and further containing at least 8,400 µg cocoa polyphenols per gram milk component, advantageously at least 9,000 µg, even better at least 10,000 µg, and most preferred at least 12,000 µg cocoa polyphenols per gram milk component.

Another embodiment of the invention relates to a chocolate comprising at least one milk component and at least one fat, and further containing at least 465 µg cocoa polyphenol pentamer per gram milk component, preferably at least 1,000 µg, advantageously at least 2,000 µg, even better at least 3,000 µg, and most preferred at least 3,500 µg cocoa polyphenol pentamer per gram milk component.

A still further embodiment of the invention relates to a chocolate comprising at least one sugar and at least one fat, and further containing at least 7,100 µg cocoa polyphenols per gram sugar, preferably at least 10,000 µg, advantageously at least 13,000 µg, even better at least 16,000 µg, and most preferred at least 18,000 µg cocoa polyphenols per gram sugar.

Another embodiment of the invention relates to a chocolate comprising at least one sugar and at least one fat, and further containing at least 350 µg cocoa polyphenol pentamer per gram sugar, preferably at least 550 µg, advantageously at least 850 µg, even better at least 1,100 µg, and most preferred at least 1,350 µg cocoa polyphenol pentamer per gram sugar.

9. Chocolate-Flavored Confections

A still further aspect of the invention relates to chocolate-flavored confections (e.g., a chocolate-flavored hard candy) comprising a cocoa component, wherein the chocolate-flavored confection contains an effective amount of cocoa polyphenols per gram chocolate-flavored confection to provide a health benefit. Preferably, the chocolate-flavored confection (excluding chocolate) comprises at least 1 µg cocoa polyphenols per gram chocolate-flavored confection, advantageously at least 2 µg, even better at least 5 µg, and most preferred at least 10 µg cocoa polyphenols per gram chocolate-flavored confection. According to one preferred embodiment, the chocolate-flavored confection comprises at least 25 µg cocoa polyphenols per gram chocolate-flavored confection, advantageously at least 50 µg, even better at least 100 µg, and most preferred at least 150 µg cocoa polyphenols per gram chocolate-flavored confection.

The cocoa component may be selected from the group consisting of: (a) chocolate liquor; (b) partially defatted or fully defatted cocoa solids; (c) cocoa nib or fractions thereof; (d) cocoa polyphenol extract; and (e) mixtures thereof.

Another embodiment of the invention relates to chocolate-flavored confections comprising a cocoa component, wherein the chocolate-flavored confection contains an effective amount of cocoa polyphenol pentamer per gram chocolate-flavored confection to provide a health benefit. Preferably, the chocolate-flavored confection (excluding chocolate) comprises at least 1 µg cocoa polyphenol pentamer per gram chocolate-flavored confection, advantageously at least 2 µg, even better at least 5 µg, and most preferred at least 10 µg cocoa polyphenol pentamer per gram chocolate-flavored confection. According to one preferred embodiment, the chocolate-flavored confection comprises at least 25 µg cocoa polyphenol pentamer per gram chocolate-flavored confection, advantageously at least 50 µg, even better at least 100 µg, and most preferred at least 150 µg cocoa polyphenol pentamer per gram chocolate-flavored confection.

A still further aspect of the invention relates to chocolate-flavored confections (excluding chocolate) comprising a cocoa component, wherein the chocolate-flavored confection contains an effective amount of cocoa polyphenols per gram cocoa component to provide a health benefit. Preferably, the chocolate-flavored confection comprises at least 1 µg cocoa polyphenols per gram cocoa component, advantageously at least 2 µg, even better at least 5 µg, and most preferred at least 10 µg cocoa polyphenols per gram chocolate-flavored confection. According to one preferred embodiment, the chocolate-flavored confection comprises at least 25 µg cocoa polyphenols per gram cocoa component, advantageously at least 50 µg, even better at least 100 µg, and most preferred at least 150 µg cocoa polyphenols per gram cocoa component.

Another embodiment of the invention relates to chocolate-flavored confections (excluding chocolate) comprising a cocoa component, wherein the chocolate-flavored confection contains an effective amount of cocoa polyphenol pentamer per gram cocoa component to provide a health benefit. Preferably, the chocolate-flavored confection comprises at least 1 µg cocoa polyphenol pentamer per gram chocolate-flavored confection, advantageously at least 2 µg, even better at least 5 µg, and most preferred at least 10 µg cocoa polyphenol pentamer per gram cocoa component. According to one preferred embodiment, the chocolate-flavored confection comprises at least 25 µg cocoa polyphenol pentamer per gram cocoa component, advantageously at least 50 µg, even better at least 100 µg, and most preferred at least 150 µg cocoa polyphenol pentamer per gram cocoa component.

10. Chocolate-Flavored Compositions

A still further aspect of the invention relates to a chocolate-flavored composition (excluding chocolate, e.g, a chocolate-flavored ice cream, etc.) comprising a cocoa component, wherein the chocolate-flavored composition contains an effective amount of cocoa polyphenols per gram chocolate-flavored composition to provide a health benefit. Preferably, the chocolate-flavored composition comprises at least 1 µg cocoa polyphenols per gram chocolate-flavored composition, advantageously at least 2 µg, even better at least 5 µg, and most preferred at least 10 µg cocoa polyphenols per gram chocolate-flavored composition. According to one preferred embodiment, the chocolate-flavored composition comprises at least 25 µg cocoa polyphenols per gram chocolate-flavored composition, advantageously at least 50 µg, even better at least 100 µg, and most preferred at least 150 µg cocoa polyphenols per gram chocolate-flavored composition.

Another embodiment of the invention relates to a chocolate-flavored composition comprising a cocoa component, wherein the chocolate-flavored composition contains an effective amount of cocoa polyphenol pentamer per gram chocolate-flavored composition to provide a health benefit. Preferably, the chocolate-flavored composition comprises at least 1 µg cocoa polyphenol pentamer per gram chocolate-flavored composition, advantageously at least 2 µg, even better at least 5 µg, and most preferred at least 10 µg cocoa polyphenol pentamer per gram chocolate-flavored composition. According to one preferred embodiment, the chocolate-flavored composition comprises at least 25 µg cocoa polyphenol pentamer per gram chocolate-flavored composition, advantageously at least 50 µg, even better at least 100 µg, and most preferred at least 150 µg cocoa polyphenol pentamer per gram chocolate-flavored composition.

A still further aspect of the invention relates to a chocolate-flavored composition comprising a cocoa component, wherein the chocolate-flavored composition contains an effective amount of cocoa polyphenols per gram cocoa component to provide a health benefit. Preferably, the chocolate-flavored composition comprises at least 1 µg cocoa polyphenols per gram cocoa component, advantageously at least 2 µg, even better at least 5 µg, and most preferred at least 10 µg cocoa polyphenols per gram chocolate-flavored composition. According to one preferred embodiment, the chocolate-flavored composition comprises at least 25 µg cocoa polyphenols per gram cocoa component, advantageously at least 50 µg, even better at least 100 µg, and most preferred at least 150 µg cocoa polyphenols per gram cocoa component.

Another embodiment of the invention relates to a chocolate-flavored composition comprising a cocoa component, wherein the chocolate-flavored composition contains an effective amount of cocoa polyphenol pentamer per gram cocoa component to provide a health benefit. Preferably, the chocolate-flavored composition comprises at least 1 µg cocoa polyphenol pentamer per gram chocolate-flavored composition, advantageously at least 2 µg, even better at least 5 µg, and most preferred at least 10 µg cocoa polyphenol pentamer per gram cocoa component. According to one preferred embodiment, the chocolate-flavored composition comprises at least 25 µg cocoa polyphenol pentamer per gram cocoa component, advantageously at least 50 µg, even better at least 100 µg, and most preferred at least 150 µg cocoa polyphenol pentamer per gram cocoa component.

11. Additional Products

Another aspect of the invention relates to an edible or ingestible or chewable product containing a cocoa polyphenols additive or a derivative thereof. According to one embodiment, the cocoa polyphenol additive is an extract from cocoa beans or a cocoa component thereof or the cocoa polyphenol additive is a synthetic compound structurally similar or identical to the cocoa polyphenols. Preferably, the product comprises at least 1 µg cocoa polyphenols per gram product, advantageously at least 2 µg, even better at least 5 µg, and most preferred at least 10 µg cocoa polyphenols per gram product. According to one preferred embodiment, the product comprises at least 25 µg cocoa polyphenols per gram product, advantageously at least 50 µg, even better at least 100 µg, and most preferred at least 150 µg cocoa polyphenols per gram product.

According to another embodiment, the product comprises at least 1 µg cocoa polyphenol pentamer per gram product, advantageously at least 2 µg, even better at least 5 µg, and most preferred at least 10 µg cocoa polyphenol pentamer per gram product. According to one preferred embodiment, the product comprises at least 25 µg cocoa polyphenol pentamer per gram cocoa component, advantageously at least 50 µg, even better at least 100 µg, and most preferred at least 150 µg cocoa polyphenol pentamer per gram product.

Accordingly, one embodiment of the invention relates to an ingestible product containing the cocoa polyphenols additive or a derivative thereof and a second ingestible component.

Another embodiment of the invention relates to a chewable composition (e.g., chewing gum) comprising a cocoa polyphenol additive or a derivative thereof.

Another embodiment of the invention relates to an edible composition comprising a cocoa component containing a cocoa polyphenols content from fair average quality cocoa beans, wherein the cocoa component contains at least 25% of the cocoa polyphenols content of the fair average quality cocoa beans, advantageously at least 35%, even better at least 50% and most preferred at least 65% by weight.

A still further object of the invention relates to an edible composition comprising a cocoa component containing a cocoa polyphenols content from raw freshly harvested cocoa beans, wherein the cocoa component contains at least 5% of the cocoa polyphenols content of the raw freshly harvested cocoa beans, preferably at least 10%, advantageously at least 15%, even better at least 20% and most preferred at least 25% by weight.

Yet another embodiment of the invention relates to an edible product comprising an edible composition and at least 1 µg cocoa polyphenols, wherein the edible product is substantially free of chocolate flavor and chocolate aroma (i.e., a rice cake coated with cocoa polyphenol extract). Preferably, the product comprises at least 2 µg cocoa polyphenols per gram product, advantageously at least 5 µg, even better at least 10 µg, and most preferred at least 20 µg cocoa polyphenols per gram product. According to one preferred embodiment, the product comprises at least 50 µg cocoa polyphenols per gram cocoa component, advantageously at least 100 µg, even better at least 150 µg, and most preferred at least 200 µg cocoa polyphenols per gram product.

According to another embodiment, the product free of chocolate aroma/flavor comprises at least 2 µg cocoa polyphenol pentamer per gram product, advantageously at least 5 µg, even better at least 10 µg, and most preferred at least 20 µg cocoa polyphenol pentamer per gram product. According to one preferred embodiment, the product comprises at least 50 μg cocoa polyphenol pentamer per gram cocoa component, advantageously at least 100 μg, even better at least 150 μg, and most preferred at least 200 μg cocoa polyphenol pentamer per gram product.

A still further object of the invention relates to an edible composition comprising a nonalkalized chocolate liquor substantially derived from cocoa beans having a fermentation factor less than 375, preferably, advantageously less than 350, even better less than 325, and most preferred less than 300. According to a preferred embodiment, the fermentation factor is less than 275, preferably less than 250, advantageously less than 225, even better less than 200, and most preferred less than 175. According to a particularly preferred embodiment, the fermentation factor is less than 150, advantageously less than 125, and most preferred about 100.

H. Methods of Using

Using the cocoa components and the products containing cocoa polyphenols described above, novel methods of improving the health of a mammal, particularly a human, may be practiced. The products of the invention can be used in any of the uses discussed in copending U.S. application Ser. No. 08/831,245, filed Apr. 2, 1997.

Another embodiment of the invention relates to a method of improving the health of a mammal by administering an effective amount of cocoa polyphenols to the mammal each day for an effective period of time. Advantageously, the effective period of time is greater than sixty days. In one aspect, the mammal's health is improved by ingesting an edible composition containing cocoa polyphenols each day for a period of time greater than sixty days. Preferably, the edible composition contains at least 1 μg of cocoa polyphenols, advantageously at least 5 μg, even better at least 10 μg, more preferred at least 25 μg, and most preferred at least 50 μg. In another aspect, the mammal's health is improved by ingesting a chocolate containing cocoa polyphenols each day for a period of time greater than sixty days. Preferably, the chocolate contains at least 1 μg of-cocoa polyphenols, advantageously at least 5 μg, even better at least 10 μg, more preferred at least 25 μg, and most preferred at least 50 μg.

One embodiment of the invention relates to a method of improving the health of a mammal by administering an effective amount of cocoa polyphenol pentamer to the mammal each day for an effective period of time. Advantageously, the effective period of time is greater than sixty days. In one aspect, the mammal's health is improved by ingesting a non-chocolate edible composition containing cocoa polyphenol pentamer each day for a period of time greater than sixty days. Preferably, the edible composition contains at least 1 μg of cocoa polyphenol pentamer, advantageously at least 5 Ag, even better at least 10 μg, more preferred at least 25 μg, and most preferred at least 50 μg. In another aspect, the mammal's health is improved by ingesting a chocolate containing cocoa polyphenol pentamer each day for a period of time greater than sixty days. Preferably, the chocolate contains at least 1 μg of cocoa polyphenol pentamer, advantageously at least 5 μg, even better at least 10 μg, more preferred at least 25 μg, and most preferred at least 50 μg.

The cocoa polyphenols or cocoa polyphenol pentamer has an activity selected from the group consisting of reducing periodontal disease, antigingivitis, antiperiodontis, reducing atherosclerosis, LDL oxidation inhibitor, reducing hypertension, antineoplastic, antioxidant, DNA topoisomerase II enzyme inhibitor, cyclo-oxygenase modulator, lipoxygenase modulator, NO or NO-synthase modulator, non-steroidal anti-inflammatory, apoptosis modulator, platelet aggregation modulator, blood or in vivo glucose modulator, antimicrobial and inhibitor of oxidative DNA damage activity.

In yet another embodiment of the invention, a physiological response is elicited in a mammal by administering an effective amount of cocoa polyphenols or cocoa polyphenol pentamer to the mammal.

The elicited response is sustained for a period of time, or the elicited response provides a benefit to the mammal in need thereof, advantageously to modulate the effects of an internal or external stress factor.

The elicited responses include lowering the oxidative stress index (such as increasing in vivo oxidative defense indices or decreasing in vivo oxidative stress), anti-viral response, anti-bacterial response, lowering cytokine level, increasing T-cell production level, lowering hypertension and dilating blood vessels, and the stress factors include oxidative stress, viral stress, bacterial stress, elevated level of cytokine, diminished level of T-cell production, hypertension and constricted blood vessels.

The compounds of the invention or compositions containing the compounds of the invention have utility for reducing periodontal disease, antigingivitis, antiperiodontis, reducing atherosclerosis, LDL oxidation inhibitor, reducing hypertension, anti-cancer, anti-tumor or antineoplastic, antioxidant, DNA topoisomerase II enzyme inhibitor, inhibit oxidative damage to DNA, antimicrobial, cyclooxygenase and/or lipoxygenase modulator, NO or NO-synthase modulator, apoptosis, platelet aggregation and blood or in vivo glucose modulating and nonsteroidal anti-inflammatory activities.

In addition to the physiological activities elicited by the compounds of the invention or compositions containing the compounds, other compounds present in cocoa or compositions containing other compounds from noncocoa, natural sources can be combined to produce a synergistic effect to the naturally occurring cocoa polyphenols, in particular cocoa procyanidins.

One embodiment of a synergistic effect on NO and/or NO synthase modulation, for example, follows. Many foods contain appreciable amounts of L-arginine, but not necessarily the compounds of the invention. Given that L-arginine is a substrate for NO synthase, and NO dependent vasodilation is significantly improved in hypercholesterolemic animals receiving L-arginine supplementation (Cooke et al., Circulation 83, 1057–1062, 1991), and the compounds of the invention can modulate NO levels, a synergistic improvement in endothelium dependent vasodilation is expected. L-arginine levels of 1.0 to 1.1 g/100 g have been reported in unsweetened cocoa powder. From this basis, other natural products rich in L-arginine, such as peanuts, would be incorporated into recipes for maximal benefit related to NO and NO synthase modulation.

Another embodiment relates to the use of a noncocoa source containing procyanidins. Cinnamon, for example, has been analytically examined for procyanidins and related compounds (Moritomo et al., Chem. Pharm. Bull. 33:10, 4338–4345, 1985; Moritomo et al., Chem. Pharm. Bull. 33:10, 2281–2286, 1985; Moritomo et al., Chem. Pharm. Bull. 34:2, 633–642, 1986; and Moritomo et al., Chem. Pharm. Bull. 34:2, 643–649, 1986), some of which are structurally related to the cocoa procyanidins. Moreover, cinnamon has been reported (Coe, S. D. and Coe, M. D., *The True History of Chocolate*, Thames and Hudson Ltd., London, 1996) to be a part of chocolate drink recipes since 1692. Thus, the inclusion of cinnamon (containing procyanidins) to cocoa (containing procyanidins) to prepare any cocoa snack, SOI or non SOI chocolate, beverage or edible food stuff would be expected to elicit a synergistic physiological effect. Similarly, the addition of various citrus essential oils, would be expected to produce a synergistic effect with the indigenous cocoa procyanidins. Naturally expressed citrus essential oils contain numerous bioflavonoids and complex terpenoids, some of which have physiological properties such as geraniol (Burke et al., Lipids 32:2, 151–156, 1997). It is noteworthy that distilled citrus oils lack the bioflavonoids and that folded oils would contain different proportions of the terpene hydrocarbons, including the sesquiterpenes and their oxygenated forms, all of which can be manipulated to synergize with the numerous physiological utilities of the cocoa procyanidins.

The skilled artisan will recognize many variations from these examples to cover a wide range of formulas, ingredients (e.g. wine or tea solids), processing and mixtures to rationally take advantage of the synergistic effects of naturally occurring levels and distribution of cocoa procyanidins used in combination with other natural products containing identical or different phytochemicals. Further, the skilled artisan will recognize the inclusion of noncocoa phytochemicals in various combinations can be added as recipe ingredients to prepare SOI or non SOI chocolate, any cocoa based snack, beverage, syrup, cocoa, flavoring or supplement.

changes and modification can be made with respect to the invention.

That is, the skilled artisan will recognize many variations in these examples to cover a wide range of formulas, ingredients, processing, and mixtures to rationally adjust the naturally occurring levels of the compounds of the invention for a variety of chocolate applications.

TABLE 1A

COCOA Polyphenols CONTENT OF FINISHED PRODUCTS IN EXAMPLES (micrograms/gram)

| SAMPLE | THEORETICAL PENTAMER | ACTUAL PENTAMER | THEORETICAL POLYPHENOL | ACTUAL POLYPHENOL |
|---|---|---|---|---|
| Chocolate Cookie Control | 181 | 37 | 2,482 | 1,978 |
| Cookie 50:50 | 278 | 39 | 3,973 | 2,698 |
| Cookie 100% Cocoa Polyphenols | 376 | 46 | 5,464 | 3,841 |
| Choco Power Bar | NA | trace | NA | 100 |
| VO2 control | NA | trace | NA | 209 |
| VO2 cocoa polyphenol | 175 | 22 | 2,548 | 1,710 |
| Cacao Puffs | NA | trace | NA | 27 |
| Cereal | 286 | 23 | 4,157 | 3,453 |
| Fruit Bar | 408 | 105 | 5,153 | 5,851 |
| Fruit Bar Fitting | 1,488 | 349 | 18,758 | 12,771 |
| Jello-choco pudding | NA | trace | NA | trace |
| Pudding (stove) | 352 | 70 | 18,758 | 1,559 |
| Pudding (microwave) | 352 | 67 | 18,758 | 1,406 |
| Pudding (skim) | 352 | 42 | 18,758 | 1,215 |
| Mole control | 1.5 | trace | 44 | 79 |
| Mole 50:50 | 14.4 | trace | 188 | 155 |
| Mole 100% cocoa polyphenol | 27.4 | trace | 332 | 213 |
| Quaker Choc puff rice | NA | trace | NA | trace |
| Sprayed rice cake | 251.5 | 38 | 3,655 | 4,842 |
| Brownie (control) | 9.9 | 12 | 295 | 645 |
| Brownie (50:50) | 96.9 | 70 | 1,252 | 2,099 |
| Brownie (100% cocoa polyphenol) | 183.9 | 97 | 2,225 | 2,981 |
| Chocolate-Flavored Nougat | 2.4 | 18 | 34.2 | 776 |
| Cinnamon Caramel | 43 | 27 | 621 | 1,037 |

NA: Not Available

TABLE 1B

COCOA POLYPHENOL INGREDIENTS USED IN EXAMPLES

| Cocoa Polyphenols MEDIUM | PENTAMER | TOTAL POLYPHENOL |
|---|---|---|
| Extract | 29,767 µg | 375,170 µg |
| Cocoa Powder | 2,138 µg | 31,072 µg |
| Liquor | 1,957 µg | 23,673 µg |

EXAMPLES

The following examples are illustrative of some of the products and methods of making the same falling within the scope of the present invention. They are, of course, not to be considered in any way limitative of the invention. Numerous

EXAMPLE 1

Cocoa Source and Method of Preparation

Several *Theobroma cacao* genotypes which represent the three recognized horticultural races of cocoa (Enriquez et al., Cocoa Cultivars Register IICA, Turrialba, Costa Rica 1967; Engels, Genetic Resources of Cacao: A Catalogue of the CATIE Collection, Tech. Bull. 7, Turrialba, Costa Rica 1981) were obtained from the three major cocoa producing origins of the world. A list of those genotypes used in this study are shown in Table 2. Harvested cocoa pods were opened and the beans with pulp were removed for freeze drying. The pulp was manually removed from the freeze dried mass and the beans were subjected to analysis as follows. The unfermented, freeze dried cocoa beans were first manually dehulled, and ground to a fine powdery mass with a TEKMAR Mill. The resultant mass was then defatted overnight by Soxhlet extraction using redistilled hexane as the solvent. Residual solvent was removed from the defatted mass by vacuum at ambient temperature.

TABLE 2

Description of *Theobroma cacao* Source Material

| GENOTYPE | ORIGIN | HORTICULTURAL RACE |
|---|---|---|
| UIT-1 | Malaysia | Trinitario |
| Unknown | West Africa | Forastero |
| ICS-100 | Brazil | Trinitario (Nicaraguan Criollo ancestor) |
| ICS-39 | Brazil | Trinitario (Nicaraguan Criollo ancestor) |
| UF-613 | Brazil | Trinitario |
| EEG-48 | Brazil | Forastero |
| UF-12 | Brazil | Trinitario |
| NA-33 | Brazil | Forastero |

EXAMPLE 2

Cocoa Polyphenol Extraction Procedures

A. Method 1

Cocoa polyphenols were extracted from the defatted, unfermented, freeze dried cocoa beans of Example 1 using a modification of the method described by Jalal and Collin, Phytochemistry 6 1377–1380 (1978). Cocoa polyphenols were extracted from 50 gram batches of the defatted cocoa mass with 2×400 mL 70% acetone/deionized water followed by 400 mL 70% methanol/deionized water. The extracts were pooled and the solvents removed by evaporation at 45° C. with a rotary evaporator held under partial vacuum. The resultant aqueous phase was diluted to 1 L with deionized water and extracted 2× with 400 mL $CHCl_3$. The solvent phase was discarded. The aqueous phase was then extracted 4× with 500 mL ethyl acetate. Any resultant emulsions were broken by centrifugation on a Sorvall RC 28S centrifuge operated at 2,000×g for 30 min. at 10° C. To the combined ethyl acetate extracts, 100–200 mL deionized water was added. The solvent was removed by evaporation at 45° C. with a rotary evaporator held under partial vacuum. The resultant aqueous phase was frozen in liquid $N_2$ followed by freeze drying on a LABCONCO Freeze Dry System. The yields of crude procyanidins that were obtained from the different cocoa genotypes are listed in Table 3.

TABLE 3

Crude Procyanidin Yields

| GENOTYPE | ORIGIN | YIELDS (g) |
|---|---|---|
| UIT-1 | Malaysia | 3.81 |
| Unknown | West Africa | 2.55 |
| ICS-100 | Brazil | 3.42 |
| ICS-39 | Brazil | 3.45 |
| UF-613 | Brazil | 2.98 |
| EEG-48 | Brazil | 3.15 |
| UF-12 | Brazil | 1.21 |
| NA-33 | Brazil | 2.23 |

B. Method 2

Alternatively, cocoa polyphenols may also be extracted from the defatted, unfermented, freeze dried cocoa beans of Example 1 with 70% aqueous acetone. Ten grams of defatted material is slurried with 100 mL solvent for 5–10 min. The slurry is centrifuged for 15 min. at 4° C. at 3000×g and the supernatant passed through glass wool. The filtrate is subjected to distillation under partial vacuum and the resultant aqueous phase frozen in liquid $N_2$, followed by freeze drying on a LABCONCO Freeze Dry System. The yields of crude procyanidins range from 15–20% of the starting material.

Without wishing to be bound by any particular theory, it is believed that the differences in crude yields reflected variations encountered with different genotypes, geographical origin, horticultural race, and method of preparation.

EXAMPLE 3

Varying the Levels of cocoa Polyphenols Via Manipulating the Degree of Fermentation Cocoa beans (*T. cocoa*, SIAL 659) were subjected to varying degrees of fermentation by removing and analyzing samples of beans taken from a mass of fermenting beans at varying periods of time of fermentation ranging from t0 (time=zero hours) to t120 (time=120 hours). The results are shown in Table 4.

TABLE 4

Procyanidin Levels ppm ($\mu$g/g) in defatted powder with varying degrees of fermentation

| | Oligomer | | | | | | | | | | | |
|---|---|---|---|---|---|---|---|---|---|---|---|---|
| SAMPLE | Monomer | Dimer | Trimer | Tetramer | Pentamer | Hexamer | Heptamer | Octamer | Nonamer | Decamer | Uedecamer | Total |
| A - t0 | 21,929 | 10,072 | 10,106 | 7788 | 5311 | 3242 | 1311 | 626 | 422 | 146 | tr | 60,753 |
| B - t24 | 21,088 | 9762 | 9119 | 7094 | 4774 | 2906 | 1364 | 608 | 361 | 176 | tr | 57,252 |
| C - t48 | 20,887 | 9892 | 9474 | 7337 | 4906 | 2929 | 1334 | 692 | 412 | 302 | tr | 58,165 |
| D - t96 | 9552 | 5780 | 5062 | 3360 | 2140 | 1160 | 464 | 254 | 138 | tr | ND | 27,910 |
| E - t120 | 8581 | 4665 | 4070 | 2527 | 1628 | 888 | 326 | 166 | 123 | tr | ND | 22,974 |

ND = none detected
tr = trace (<50 $\mu$g/g)

EXAMPLE 4

Method of obtaining Cocoa Polyphenol Defatted Cocoa Solids from Cocoa Beans Utilizing the Inventive Process Commercially available cocoa beans having an initial moisture content of from about 7 to 8 percent by weight were pre-cleaned using an 11"×56" Scalperator (manufactured by Carter Day International, Minneapolis, Minn., USA). Approximately 600 bags of cocoa beans (39,000 kg) were pre-cleaned over a 6.5 hour time period.

The beans were fed into the inlet hopper where the flow rate was regulated by a positive feed roll. The beans were fed onto the outside of a rotating wire mesh scalping reel. The beans passed through the wire mesh reel and subsequently through an air aspiration chamber where light dirt, dust and strings were aspirated out of the product stream. The beans that did not pass through the scalping reel were conveyed to the reject stream. This reject stream consisted of large clumps of beans, sticks, stones, etc. The amount of resultant reject was approximately 150 kg, or 0.38% of the starting material. The resulting pre-cleaned product weighed about 38,850 kg and was passed to the bean cleaning step.

The pre-cleaned bean products from the Scalperator were then further cleaned using a Camas International SV4-5 Air Fluidized Bed Density Separator (AFBDS, manufactured by Camas International, Pocotello, Ind., USA). About 38,850 kg of cocoa bean products were fed into the AFBDS over a time period of about 6.5 hours. The apparatus removed substantially all heavy impurities such as stones, metal, glass, etc. from the beans, as well as lighter unusable materials such as moldy and infested cocoa beans, resulting in a cleaned bean product which contained substantially only usable cocoa beans. The resulting heavy impurities removed weighed about 50 kg and the light unusable materials weighed about 151 kg. A total of about 38,649 kg of cleaned beans was obtained after both the pre-cleaning and cleaning steps described hereinabove (99.1% yield after cleaning).

The cleaned cocoa beans were then passed through a infra-red heating apparatus. The apparatus used was the Micro Red 20 electric infra-red vibratory Micronizer (manufactured by Micronizing Company (U.K.) Limited, U.K.). The Micronizer was run at a rate of about 1,701 kilograms per hour. The depth of beans in the vibrating bed of the Micronizer was about 2 inches or about 2–3 beans deep. The surface temperature of the Micronizer was set at about 165° C., resulting in an IBT of about 135° C., for a time ranging from 1 to 1.5 minutes. This treatment caused the shells to dry rapidly and separate from the cocoa nib. Since substantially all of the cocoa beans fed into the Micronizer were whole beans and were substantially free of small broken pieces of bean or shell, no sparks or fires were observed during the infra-red heating step. The broken pieces separated by the vibrating screen prior to the Micronizer were re-introduced into the product stream prior to the winnowing step.

The beans after the Micronizer had a moisture content of about 3.9% by weight. The beans emerged from the Micronizer at an IBT of about 135° C. and were immediately cooled to a temperature of about 90° C. in about three minutes to minimize additional moisture loss. The total beans available after the heating step was about 36,137 kg.

The beans were then subjected to winnowing using a Jupiter Mitra Seita winnower (manufactured by Jupiter Mitra Seita, Jakarta, Indonesia). The winnowing step cracked the beans to loosen the shells and separated the lighter shells from the nibs while at the same time minimizing the amount of nib lost with the shell reject stream. The feed rate into the winnower was about 1,591 kg per hour. The resultant products included about 31,861 kg of usable nibs and 4,276 kg of reject shells. The overall yield of usable nibs from starting material was about 81.7%.

The resulting cocoa nibs were pressed using a Dupps 10-6 Pressor (manufactured by The Dupps Company, Germantown, Ohio, USA). A steady, consistent feed of about 1,402 kg per hour of nibs was fed into two screw presses to extract butter. The press produced about 16,198 kg of cocoa butter which contained about 10% cocoa solids, and about 15,663 kg of cocoa solids which contained about 10% butter.

The cocoa butter was further processed using a Sharples P3000 decanting centrifuge (manufactured by Jenkins Centrifuge Rebuilders, N. Kansas City, Mo., USA). The centrifugation resulted in the removal of the solids from the butter by centrifugal forces. The centrifuging reduced the 10% solids in the butter to about 1–2% solids, and resulted in about 13,606 kg of butter and 2,592 kg of cocoa solids containing about 40 to 45% butter.

The butter containing 1–2% solids was further processed using a plate and frame filter (manufactured by Jupiter Mitra Seita) which removed the remaining solids from the butter and resulted in about 13,271 kg of clear cocoa butter and about 335 kg of cocoa solids containing 40–45% butter.

The cocoa solids removed from the centrifuge and the filter press contained about 40–45% fat and were pressed in a batch hydraulic press to produce 10% fat cocoa cake. This material produced about 1,186 kg of clear butter and 1,742 kg of cocoa solids.

The total clear butter yield from the incoming beans was 14,456 kg, or 37.1%. The total cocoa solids produced from the incoming beans was 17,405 kg, or 44.6%. The butter was subsequently tempered and packaged.

EXAMPLE 5

Method for Quantifying Cocoa Polyphenol Levels in Various Samples Processed by Conventional and Inventive Methods Cocoa polyphenol extracts were prepared from a variety of cocoa sources (shown in Table 5) by grinding 6–7 g of sample using a Tekmar A-10 Analytical Mill for 5 min, or, in the case of liquors, from 6–7 g of chocolate liquor sample without additional grinding. The sample was then transferred to a 50 mL polypropylene centrifuge tube, approximately 35 mL of hexane was added, and sample was shaken vigorously for 1 min. Sample was spun at 3000 RPM for 10 min using an International Equipment Company IECPR-7000 Centrifuge. After decanting the hexane layer, the fat extraction process was repeated two more times. Approximately 1 g of the defatted material was weighed into a 15 mL polypropylene centrifuge tube and 5 mL of a 70% acetone: 29.5% water: 0.5% acetic acid solution was added. The sample was vortexed for about 30 sec using a Scientific Industries Vortex Genie 2 and spun at 3000 RPM for 10 min in the IECPR-7000 Centrifuge. The liquor was then filtered into a 1 ml hypovial through a Millex-HV 0.45$\mu$ filter.

Cocoa polyphenol extracts were analyzed by a Hewlett Packard 1090 Series II HPLC system equipped with a HP Model 1046A Programmable Fluorescence detector and Diode Array detector. Separations were effected at 37° C. on a 5$\mu$ Supelco Supelcosil LC-Si column (250×4.6 mm) connected to a Supelco Supelguard LC-Si 5 $\mu$m guard column (20×2.1 mm). Procyanidins were eluted by linear gradient under the following conditions: (time % A, % B, % C); (0, 82, 14, 4), (30, 67.6, 28.4, 4), (60, 46, 50, 4), (65, 10, 86, 4), followed by a 5 minute re-equilibration. Mobile phase composition was A=dichloromethane, B=methanol, and C=acetic acid:water at a volume ratio of 1:1. A flow rate of 1 mL/min was used. Components were detected by fluorescence, where $\lambda_{ex}$=276 nm and $\lambda_{em}$=316 nm, or by UV at 280 nm. Epicatechin in the concentration of approximately 1 mg/ml was used as an external standard.

HPLC conditions:

250×4.6 mm Supelco Supelcosil LC-Si column (5 $\mu$m)

20×2.1 mm Supelco Supelguard LC-Si (5 $\mu$m) guard column

Detectors: Photodiode Array at 280 nm

Fluorescence $\lambda_{ex}$=276 nm; $\lambda_{em}$=316 nm

Flow rate: 1 mL/min
Column temperature: 37° C.

| Gradient | $CH_2Cl_2$ | methanol | acetic acid/ water (1:1) |
|---|---|---|---|
| 0 | 76 | 20 | 4 |
| 25 | 46 | 50 | 4 |
| 30 | 10 | 86 | 4 |

A sample set containing 9 pressed cocoa cakes, 3 cocoa meals, 3 pressed cocoa powder samples, 3 liquor samples, 3 bean samples and 2 nib samples were analyzed for procyanidin levels by the aforementioned procedure. The results are shown in Table 5. Procyanidin levels were compared to those previously reported for Sulawesi samples defatted by the inventive process. The screw pressed cocoa cake from Sanchez beans (comparative Sample No. E2) contained procyanidin levels closest to that found in the inventive processed samples, but 30% less total procyanidins.

Moreover, the inventive process retained the highest level of higher oligomers, i.e., the level of pentamers from the E2 sample was 1983 ug/g as compared to 3,168 ug/g (sample #937-59) from the inventive process.

Additionally, a sample set of the following cocoa sources (a) through (d) were analyzed for cocoa polyphenols levels by the aforementioned procedure:

(a) Sulawesi raw beans prior to processing by the inventive process (RB-1), (b) cocoa bean nibs obtained from the inventive process, according to Example 4, except as modified at the infra-red heating stage by adjusting the temperature to that which polyphenols would be conserved, i.e., approximately 100–110° C. (MN-1), (c) two samples of cocoa solids nonfat obtained from the inventive process (MS-120 and MS-150), (d) conventionally processed, Sulawesi raw nibs prior to processing (RN-1 and RN-2), and (e) Sulawesi, conventionally processed partially defatted cocoa solids (CS-1 and CS-2).

The results are shown in Table 6.

TABLE 5

Polyphenols Content Defatted Dry Weight Basis

| | | Oligomer Amount (µg/g) | | | | | | | | | |
|---|---|---|---|---|---|---|---|---|---|---|---|
| Sample | Description | Monomer | Dimer | Trimer | Tetramer | Pentamer | Hexamer | Heptamer | Octamer | Nonamer | Total Polyphenol |
| 937–59 | Inventive (Sulawesi unfermented screw pressed cocoa) | 9433 | 5929 | 5356 | 4027 | 3168 | 2131 | 1304 | 739 | 439 | 32743 |
| E1 | Comparative (screw pressed cocoa cake-Sulawesi) | 8713 | 5538 | 3880 | 2289 | 1553 | 762 | 372 | 210 | 60 | 23376 |
| E2 | Comparative (screw pressed cocoa cake-Sanchez) | 8733 | 5564 | 4836 | 3031 | 1983 | 1099 | 3489 | 361 | 221 | 29318 |
| E3 | Comparative (screw pressed cocoa powder-Sulawesi) | 7104 | 4915 | 3642 | 2020 | 1121 | 576 | 273 | 153 | 66 | 19871 |
| E4 | Comparative (hydraulically pressed cocoa cake-blend of origins) | 7157 | 3981 | 2479 | 1226 | 583 | 260 | 87 | — | — | 15773 |
| E5 | Comparative (hydraulically pressed cocoa powder-blend of origins) | 5811 | 3169 | 1503 | 537 | 171 | 55 | — | — | — | 11245 |
| E6 | DeZaan defatted cocoa powder - DIS - supercritical fluid extracted - alkalized unknown bean origin) | 581 | 421 | 123 | 35 | — | — | — | — | — | 1161 |
| E7 | Comparative (roasted cocoa nibs - blend of origins) | 2526 | 1551 | 824 | 206 | 77 | 64 | 43 | — | — | 5291 |
| E8 | Comparative (propane extracted cocoa nibs - blend of origins) | 2904 | 1855 | 927 | 239 | 116 | 63 | 37 | — | — | 6140 |
| E9 | Comparative (Javabeans) | 2677 | 2092 | 1645 | 984 | 632 | 378 | 240 | 127 | 93 | 8868 |
| E10 | Comparative (Papua New Guinea beans) | 2856 | 1960 | 1672 | 748 | 318 | 145 | 74 | 36 | — | 7807 |
| E11 | Comparative (Papua New Guinea beans) | 5255 | 3652 | 2402 | 959 | 485 | 261 | 159 | 54 | — | 13228 |
| 937–59 | South Region, Sulawesi Liquor | 1801 | 1205 | 555 | 114 | — | — | — | — | — | 3675 |
| 937–59 | Southeast Region, Sulawesi Liquor | 3891 | 2131 | 1213 | 457 | 150 | 31 | — | — | — | 7873 |
| 937–59 | Central Region, Sulawesi Liquor | 3668 | 1718 | 847 | 265 | 68 | — | — | — | — | 6566 |
| CC 1 | Comparative Screw Press Cake #1 | 2267 | 2034 | 1360 | 579 | 297 | 132 | 50 | 27 | 14 | 6759 |
| CC 2 | Comparative Screw Press Cake #2 | 2894 | 2313 | 1546 | 681 | 323 | 138 | 49 | 35 | 21 | 8001 |
| CC 3 | Comparative Screw Press Cake #3 | 2437 | 1878 | 1231 | 561 | 339 | 88 | 44 | 12 | trace | 6589 |

TABLE 6

Defatted Dry Weight Basis

| | | Oligomer Amount (µg/g) | | | | | | | | | | |
|---|---|---|---|---|---|---|---|---|---|---|---|---|
| Sample | Description | Monomer | Dimer | Trimer | Tetramer | Pentamer | Hexamer | Heptamer | Octamer | Nonamer | Total Polyphenol | % Fat |
| RB-1 | Raw Beans, Sulawesi | 11354 | 5924 | 4643 | 3180 | 2181 | 1143 | 529 | 305 | 165 | 31425 | 48.0 |
| MN-1 | Inventive nibs (RB-1 = starting material) | 13129 | 5909 | 4034 | 2120 | 1334 | 792 | 441 | 160 | 94 | 28014 | 47.1 |
| MS-120 | Inventive solids @ 120 psi (RB-1 = starting material) | 15301 | 6592 | 4447 | 2526 | 1507 | 721 | 360 | 219 | 139 | 31811 | 11.9 |

TABLE 6-continued

Defatted Dry Weight Basis

| | | Oligomer Amount (μg/g) | | | | | | | | | | |
|---|---|---|---|---|---|---|---|---|---|---|---|---|
| Sample | Description | Monomer | Dimer | Trimer | Tetramer | Pentamer | Hexamer | Heptamer | Octamer | Nonamer | Total Polyphenol | % Fat |
| MS-150 | Inventive solids @ 150 psi (RB-1 = starting material) | 10025 | 5560 | 4839 | 3245 | 2106 | 1139 | 542 | 284 | 214 | 27955 | 11.1 |
| RN-1 | Raw nibs, Sulawesi | 7976 | 5643 | 5426 | 4185 | 3021 | 1806 | 1150 | 624 | 360 | 30192 | 48.5 |
| CS-1 | Conventional solids, Sulawesi | 10527 | 4887 | 2969 | 1585 | 691 | 267 | 35 | 26 | trace | 20986 | 25.8 |
| RN-2 | Raw nibs, Sulawesi | 12219 | 7635 | 7202 | 5619 | 4014 | 2384 | 1471 | 751 | 406 | 41701 | 47.3 |
| CS-2 | Conventional solids, Sulawesi | 10170 | 4863 | 2802 | 1333 | 254 | 182 | 128 | 37 | 40 | 19811 | 26.3 |

Oligomer amount have been rounded to the nearest whole number; total polyphenols may include additional polyphenols above nonamer.
The total polyphenol amounts for MS-120 represent nearly 100% recovery by inventive process.
The total polyphenol amounts for MS-150 represent nearly 89% recovery by inventive process.

Polyphenols extracted from inventive solids such as RB-1 and MS-120 can be purified by preparative normal phase chromatography by modifying the method of Rigaud et al., (1993) J. Chrom. 654: 255–260. Separations are affected at ambient temperature on a 5 u Supelcosil LC-Si 100A column (50×2 cm), with an appropriate guard column. Procyanidins are eluted by a linear gradient under the following conditions: (time, % A, % B, flow rate); (0, 92.5, 7.5, 10); (10, 92.5, 7.5, 40); (30, 91.5, 18.5, 40); (145, 88, 22, 40); (150, 24, 86, 40); (155, 24, 86, 50); (180, 0, 100, 50). Prior to use, the mobile phase components can be mixed by the following protocol:

Solvent A preparation (82% methylene chloride, 14% methanol, 2% acetic acid, 2% water):

1. Measure 80 ml of water and dispense into a 4 L bottle.
2. Measure 80 ml of acetic acid and dispense into the same 4 L bottle.
3. Measure 560 ml of methanol and dispense into the same 4 L bottle.
4. Measure 3280 ml of methylene chloride and dispense into the same 4 L bottle.
5. Cap the bottle and mix well.
6. Purge the mixture with high purity Helium for 5 to 10 minutes to degas.

Repeat 1 to 6 two times to yield 8 volumes of solvent A.

Solvent B preparation (96% methanol, 2% acetic acid, 2% water):

1. Measure 80 ml of water and dispense into a 4 L bottle.
2. Measure 80 ml of acetic acid and dispense into the same 4 L bottle.
3. Measure 3840 ml of methanol and dispense into the same 4 L bottle.
4. Cap the bottle and mix well.
5. Purge the mixture with high purity helium for 5 to 10 minutes to degas.

Steps 1 to 5 can be repeated to yield four (4) volumes of solvent B. Mobile phase composition can be A=methylene chloride with 2% acetic acid and 2% water; B=methanol with 2% acetic acid and 2% water. The column load can be 0.7 g in 7 ml. Components can be detected by UV at 254 nm.

By this method, procyanidins can be obtained from the inventive solids.

As evidenced by the total polyphenol compositions obtained from RB-1, MN-1, MS-120 and MS-150, the inventive process affords at least 70% conservation, even at least 85% conservation (e.g., 85–89% see MS-150) and as much as at least 95% conservation (e.g., 95–100%; see MS-120) of the polyphenols concentration; whereas, the conventional processes result in approximately (less than 50%) to less than 70% conservation of the polyphenols concentration (see CS-1, CS-2).

Further, RN-1 and RN-2 represent varying concentrations of brown beans (or well fermented beans) in the composition starting material, such that, RN-1 was derived from a bean stock containing approximately 25% brown beans, and RN-2 was derived from a bean stock containing approximately 10% brown beans. As evidenced by the total polyphenol concentrations obtained from each of these sources, it is evident that the concentration of brown beans present in the starting bean stock is inversely proportional to the total polyphenols concentration that may be obtained from such a source, such that those samples derived from bean stocks containing a high percentage of brown beans will yield a relatively low amount of polyphenols (and conversely, slaty and/or purple beans which are less fermented will yield a relatively high amount of polyphenols).

The percentage fat of each composition in Table 6 was also determined. The inventive process obtained levels of fat which are comparable to that derived from conventional methods.

EXAMPLE 6

Cocoa Bean Winnowing Using An Air Fluidized-Bed Density Separator

An air fluidized bed density separator (AFBDS) manufactured by Camas International was tested to determine its effectiveness as a cocoa bean winnower. A blend of beans from West Africa and Central America were heated at about 150° C. for about 4 minutes to loosen the shell and were cracked with a centrifugal bean breaker. The cracked beans were separated by the AFBDS which resulted in a shell in nib level of between 0.29 to 0.99% and a nib in shell level of between 6.7 to 8.7%. Although the shell in nib level was acceptable, it was observed that a significant portion of the nibs in the shell was a result of pieces of nib which remained in the large pieces of shell. The large pieces of shell, resembling cracked eggshells, were conveyed on the top of the separation chamber. These shells typically had large pieces of nib entrapped within them which conveyed the nibs into the shell stream. To reduce this nib loss, a system for decreasing the size of the shell pieces was required which did not also decrease the size of the nibs.

A follow-up trial consisted of screening the flow of material between the second and third chamber of the AFBDS. This material was separated with a vibrating screen with a 0.375 inch screen opening. The screen successfully removed the large pieces of shell from the material with virtually no loss of nibs. The material which passed through the screen was introduced back into the third separation chamber and the shells and nibs were subsequently separated in the chamber. The amount of shell in nib was found to be very low, however there remained a loss of small nib in the shell stream.

To reclaim the nib in shell from the third chamber, another vibrating screen was utilized with a 0.11 inch screen opening size. This screen successfully separated the remaining nib from the shell.

The fourth chamber is typically used to remove heavy impurities such as rocks, stones, etc. As a winnower, this chamber would not be required as the winnower will typically receive material which is free of these materials. In practice, the 5% flow into the fourth chamber would be passed through chamber one and onto chamber two and three.

Table 7 is a summary of the performance of the AFBDS as a winnower:

TABLE 7

Air Fluidized Bed/Vibratory Screen Winnowing Results

|  | % of Flow | % Shell in Nib | % Nib in Shell |
|---|---|---|---|
| Chamber 1 | 65 | 0.020 | 0 |
| Chamber 2 | 20.0 | 0.002 | 0 |
| 0.375 in. screen |  |  | <0.1 |
| Chamber 3 | 9.5 | 0.020 | 0.0 |
| 0.11 inch screen | 0.5 | 0.075 | 0.99 |
| Chamber 4 | 5.0 | 0 | 0 |
| TOTAL | 100 | 0.117 | <1.09 |
| CONVENTIONAL WINNOWING |  | 1.75 max, 1.00 typical | range of 4–8% |

% of Nib refers to the amount of the clean nib that was taken out in each chamber As can be seen from the results above, the AFBDS can be used as a winnower and provide separations much finer than conventional winnowing processes. The use of an AFBDS surprisingly meets the FDA requirements for the amount of shell in the nib product, and has a very high yield of nib.

EXAMPLE 7

Method of Obtaining Chocolate Liquor from Underfermented Cocoa Beans According to One Embodiment of the Invention Commercially available Sanchez cocoa beans having an initial moisture content of 7.9% by weight were used for processing. A cut test was performed on 300 of the beans and categorized the beans as 43.7% slaty, 13.0% purple, 22.0% purple-brown, and 17.7% brown. The beans had a fermentation factor of about 210.

The beans were heat treated using an FMC Link Belt Roaster. Three batches of approximately 50 kg of the beans were separately fed at a rate of 1.5 kg/min through the roaster with a residence time of 22 minutes. The degree of roast was varied in the three 50 kg batches by controlling the air temperature in the Link Belt at 127° C., 159° C., and 181° C. The resulting internal bean temperatures (IBTs) as well as the final bean moistures for each batch are listed in Table 8. The roasted beans were cracked and winnowed in a Bauermeister Cracker/Fanner (Machine #37100) to separate the cocoa nibs from the shells. A sample of the nibs collected was analyzed for oligomer content, as also shown in Table 8.

The roasted Sanchez cocoa nibs were then fed through a Carle & Montanari Mill at a rate of 2.9 kg/min to grind the nibs into chocolate liquor. In the mill, nibs dropped from a feed hopper into a narrow space between stationary and rotating grinding plates, reducing the particle size to a few hundred microns and releasing the fat contained within the nib. The pre-milled liquor was collected for analysis and subjected to further processing. The process temperature, moisture, and oligomer content of the pre-milled liquor were measured and are reported in Table 8.

The pre-milled liquor was then processed in 10 kg batches in a Szegvari Q1 Circulation Attritor Ball Mill for 20 minutes per batch to further reduce the particle size and effect fat release. The pre-milled liquor was pumped through the milling chamber. The milling chamber overflowed into an agitated recirculation tank, from which liquor was continuously pumped back into the milling chamber. The finished liquor was collected for analysis. The process temperature, moisture, and oligomer contents of the finished liquor were measured and are shown in Table 8.

TABLE 8

Unfermented Bean Process Results

|  | Product Temperature | Percent Moisture | Pentamer Content Defatted | Total Procyanidin Defatted | Pentamer Content Total Weight | Total Procyanidin Total Weight |
|---|---|---|---|---|---|---|
| 127° C. Roast Nibs | 119° C., IBT | 4.5% | 3487 µg/g | 43800 µg/g | 1953 µg/g | 24618 µg/g |
| Pre-milled Liquor | 95° C. | 2.4% | 3110 µg/g | 43579 µg/g | 1555 µg/g | 21790 µg/g |
| Finished Liquor | 82° C. | 2.3% | 3886 µg/g | 47421 µg/g | 1943 µg/g | 23710 µg/g |
| 159° C. Roast Nibs | 142° C., IBT | 2.4% | 1157 µg/g | 30334 µg/g | 810 µg/g | 21234 µg/g |
| Pre-milled Liquor | 92° C. | 1.4% | 1311 µg/g | 32589 µg/g | 655 µg/g | 16294 µg/g |
| Finished Liquor | 59° C. | 1.4% | 1453 µg/g | 33653 µg/g | 727 µg/g | 16826 µg/g |

TABLE 8-continued

Unfermented Bean Process Results

|  | Product Temperature | Percent Moisture | Pentamer Content Defatted | Total Procyanidin Defatted | Pentamer Content Total Weight | Total Procyanidin Total Weight |
|---|---|---|---|---|---|---|
| 181° C. Roast Nibs | 162° C., IBT | 1.3% | 607 µg/g | 18266 µg/g | 425 µg/g | 12786 µg/g |
| Pre-milled Liquor | 83° C. | 0.83% | 604 µg/g | 20656 µg/g | 302 µg/g | 10328 µg/g |
| Finished Liquor | 59° C. | 0.89% | 815 µg/g | 23312 µg/g | 408 µg/g | 11656 µg/g | to 162° C.), the level of total procyanidin decreases from 24,618 µg/g to 12,786 µg/g. The decrease is particularly pronounced with the higher oligomers, e.g. the pentamer level decreases from 1,953 µg/g to 425 µg/g. Accordingly, the roasting temperature is an important factor in the retention of cocoa polyphenols, especially the higher oligomers.

EXAMPLE 8

Method of obtaining Chocolate Liquor from Fermented Cocoa Beans Utilizing Another Embodiment of the Invention Process Commercially available West African cocoa beans having an initial moisture content of 6.7% by weight were heat treated using an FMC Link Belt Roaster. A cut test performed on 300 of the beans categorized them as 2.7% slaty, 1.6% purple, 25.7% purple-brown, and 70.0% brown. The beans had a fermentation factor of 363. Three batches of approximately 50 kg of the beans were fed at a rate of 1.5 kg/min through the roaster with a residence time of 22 minutes. The degree of roast was varied in three 50 kg batches by controlling the air temperature in the Link Belt at 131° C., 156° C., and 183° C. The resulting internal bean temperatures (IBTs) as well as the final bean moistures for each batch are listed in Table 9. The roasted beans were cracked and winnowed in a Bauermeister Cracker/Fanner (Machine #37100) to separate the cocoa nibs from the shells. A sample of the nibs collected was analyzed for oligomer content, as shown in Table 9.

The roasted West African cocoa nibs were then fed through a Carle & Montanari Mill at a rate of 2.9 kg/min to grind the nibs into liquor. In the mill, the nibs dropped from a feed hopper into a narrow space between stationary and rotating grinding plates, reducing the particle size to few hundred microns and releasing the fat contained within the nib. The pre-milled liquor was collected for analysis and subjected to further processing. The process temperature, moisture, and oligomer content of the pre-milled liquor were measured and are reported in Table 9.

The West African pre-milled liquor was then processed in 10 kg batches in a Szegvari Q1 Circulation Attritor Ball Mill for 20 minutes per batch to further reduce the particle size and effect fat release. The pre-milled liquor was fed through the milling chamber. The milling chamber overflowed into an agitated recirculation tank, from which liquor was continuously pumped back into the milling chamber until a conventional particle size was reached. The finished liquor was collected for analysis. The process temperature, moisture, and oligomer content of the finished liquor were measured and are shown in Table 9.

TABLE 9

Fermented Bean Process Results

|  | Product Temperature | Percent Moisture | Pentamer Content Defatted | Total Procyanidin Defatted | Pentamer content Total Weight | Total Procyanidin Total Weight |
|---|---|---|---|---|---|---|
| 131° C. Roast Nibs | 121° C., IBT | 2.2% | 804 µg/g | 10227 µg/g | 402 µg/g | 8181 µg/g |
| Pre-milled Liquor | 94° C. | 1.9% | 904 µg/g | 11506 µg/g | 452 µg/g | 5753 µg/g |
| Finished Liquor | 61° C. | 1.8% | 865 µg/g | 11298 µg/g | 432 µg/g | 5649 µg/g |
| 156° C. Nibs | 141° C., IBT | 1.6% | 313 µg/g | 7631 µg/g | 156 µg/g | 5889 µg/g |
| Pre-milled Liquor | 85° C. | 1.2% | 275 µg/g | 7414 µg/g | 138 µg/g | 3707 µg/g |
| Finished Liquor | 62° C. | 1.2% | 324 µg/g | 7844 µg/g | 162 µg/g | 3922 µg/g |
| 183° C. Roast Nibs | 163° C., IBT | 0.85% | 124 µg/g | 5631 µg/g | 62 µg/g | 2815 µg/g |
| Pre-milled Liquor | 73° C. | 0.51% | 222 µg/g | 6529 µg/g | 111 µg/g | 3265 µg/g |
| Finished Liquor | 69° C. | 0.73% | 246 µg/g | 6610 µg/g | 123 µg/g | 3305 µg/g |

As shown in Table 9, as the temperature of the roast is increased from 131° C. to 183° C. (or the IBT from 121° C. to 163° C.), the level of total procyanidin decreases from 8,181 µg/g to 2,815 µg/g. The decrease is particularly pronounced at with the higher oligomers, e.g. the pentamer level decreases from 402 µg/g to 62 µg/g. Accordingly, the roasting temperature is an important factor in the retention of cocoa polyphenols, especially the higher oligomers, when roasting both underfermented (Example 7) and fermented (Example 8) cocoa beans.

The liquor produced in Example 8 could be further-processed into cocoa butter and cocoa powder. The cocoa solids would contain a high level of the procyanidins. Processing the liquor to butter and powder could be accomplished using a hydraulic press such as manufactured by Carle and Montanari. The liquor from Example 8 could be heated to 200 to 215° C. The liquor is then pumped into the press pots. When the pots are filled with liquor, the hydraulic ram is activated. Cocoa butter is squeezed through very fine mesh screens. The resultant products are cocoa cake and cocoa butter. The nonfat cocoa solids contained in the cocoa cake would have the same amount of procyanidins as were present in the initial liquor. The cocoa cake produced via this process could be used in edible products.

EXAMPLE 9

A Method of Infra-red Heating Cocoa Beans to Produce a Chocolate Liquor Containing Increased Levels of Cocoa Polyphenols Fair average quality (FAQ) Sulawesi cocoa beans having an initial moisture content 7.4% by weight and a fermentation factor level of 233 (31% slaty, 29% purple, 22% purple brown and 17% brown) were selected as the starting material. The cocoa beans were then passed through an infra-red heating apparatus. The apparatus used was an infra-red gas vibrating micronizer (manufactured by Micronizer Company (U.K.) Limited, U.K.). The feed rate of beans through the infra-red heater and the infra-red heater bed angle were varied to control the amount of heat treatment the beans received. The amount of time the beans spent in the infra-red heater (residence time) was determined by the bed angle and the feed rate. The times used to prepare the example material are listed in the Table 10 below. At the outlet of the micronizer the IBT of the beans was measured, these values are also shown in Table 10. The surface temperature of the beans exiting the infra-red heater are higher than the IBT. Rapid surface cooling brings the surface temperature close to the IBT in less than 1 minute. The traditional purpose of infra-red heating is to heat the whole beans and loosen the shell from the nib. In the example, the micronizer was used to roast the Sulawesi beans in a novel fashion by increasing the thermal load on the beans, i.e., high temperature short time (HTST). No fires were observed in the Micronizer during the infra-red heating. A total of 25 kg of raw beans were infra-red heated at each set point.

The infra-red heated beans were further processed into chocolate liquor. This liquor was produced using lab scale liquor processing equipment. The same processing could be done using the plant size equipment referenced in Example 7. A 1 kg sample of infra-red heated beans collected off the infra-red heater at different IBTs were cracked into smaller pieces. This is done to facilitate the separation of the nib from the shell. The laboratory piece of equipment used to remove the shell was the Limiprimita Cocoa Breaker made by the John Gordon Co. LTD. of England. The cracked beans were next passed through a laboratory scale winnowing system. The piece of equipment used was the Catador CC-1 made by the John Gordon Co. LTD of England. The result of this processing was that the shells and nibs were separated.

The cocoa nibs were next milled into a coarse liquor. This was accomplished using a Melange made by Pascall Engineering Co. LTD England. This device crushes and grinds the nibs into a chocolate liquor. The normal operating temperature for the liquor in the Melange in approximately 50° C. This same process of taking nibs to a coarse liquor could be done on a larger production scale using the Carle & Montanari Mill mentioned in Example 7. The cocoa nibs were ground in the Melange for one hour in each experiment. This cycle time was sufficient to convert the nibs to a liquor. The content of cocoa polyphenols was measured for the samples relating to the infra-red heated temperatures. These values are contained in the Table 10 below.

TABLE 10

| IBT° C. | Residence Time in Micronizer, Seconds | % Moisture in Finished Liquor | µg/g Pentamer in Defatted Liquor | µg/g of Total Polyphenols in Defatted Liquor |
|---|---|---|---|---|
| 107 | 42 | 3.9 | 3,098 | 39,690 |
| 126 | 82 | 1.87 | 1,487 | 28,815 |
| 148 | 156 | 1.15 | 695 | 23,937 |

As shown in Table 10, as the internal bean temperature of the cocoa bean is increased from 107° C. to 148° C., the level of total procyanidin decreases from 39,690 µg/g to 23,937 µg/g. The decrease is particularly pronounced at with the higher oligomers, e.g. the pentamer level decreases from 3,098 µg/g to 695 µg/g. Accordingly, the internal bean temperature of the cocoa bean resulting from any heating is an important factor in the retention of cocoa polyphenols, especially the higher oligomers.

EXAMPLE 10

Standard of Identity (SOI) and Non-Standard of Identity (non-SOI) Dark and Milk Chocolate Formulations Formulations of the compounds of the invention or combination of compounds derived by methods embodied in the invention can be prepared into SOI and non-SOI dark and milk chocolates as a delivery vehicle for human and veterinary applications. The cocoa polyphenol solids of Example 4 are used as a powder or liquor to prepare SOI and non-SOI chocolates, beverages, snacks, baked goods, and as an ingredient for culinary applications.

The following describes the processing steps used in preparing these chocolate formulations.

Process for non-SOI Dark Chocolate
1. Batch all the ingredients excluding 40% of the free fat (cocoa butter and anhy. milk fat) maintaining temperature between 30–35° C.
2. Refine to 20 microns.
3. Dry conche for 1 hour at 35° C.
4. Add full lecithin and 10% cocoa butter at the beginning of the wet conche cycle; wet conche for 1 hour.
5. Add all remaining fat, standardize if necessary and mix for 1 hour at 35° C.
6. Temper, mould and package chocolate.

Process for SOI Dark Chocolate
1. Batch all ingredients excluding milk fat at a temperature of 60° C.

2. Refine to 20 microns.
3. Dry conche for 3.5 hours at 60° C.
4. Add lecithin and milk fat and wet conche for 1 hour at 60° C.
5. Standardize if necessary and mix for 1 hour at 35° C. Temper, mould and package chocolate.

Process for non-SOI Milk Chocolate
1. Batch sugar, whole milk powder and 66% of the cocoa butter, conche for 2 hours at 75° C.
2. Cool batch to 35° C. and add cocoa powder, vanillin, chocolate liquor and 21% of cocoa butter, mix 20 minutes at 35° C.
3. Refine to 20 microns.
4. Add remainder of cocoa butter, dry conche for 1.5 hour at 35° C.
5. Add anhydrous milk fat and lecithin, wet conche for 1 hour at 35° C.
6. Standardize, temper, mould and package the chocolate.

Process for SOI Milk Chocolate
1. Batch all ingredients excluding 65% of cocoa butter and milk fat at a temperature of 60° C.
2. Refine to 20 microns.
3. Dry conche for 3.5 hours at 60° C.
4. Add lecithin, 10% of cocoa butter and anhydrous milk fat; wet conche for 1 hour at 60° C.
5. Add remaining cocoa butter, standardize if necessary and mix for 1 hour at 35° C.
6. Temper, mould and package the chocolate.

The cocoa polyphenols cocoa solids and commercial chocolate liquors used in the formulations were analyzed for the content of total cocoa polyphenols and cocoa polyphenol pentamer according to the method of Example 5 prior to incorporation in the formulations. These values were then used to calculate the expected levels in each chocolate formula. In the cases for the non-SOI dark chocolate and non-SOI milk chocolate, the products were similarly analyzed for the content of total cocoa polyphenols and cocoa polyphenol pentamer. The results are shown in Tables 11 and 12.

TABLE 11

Dark Chocolate Formulas Prepared with non-Alkalized Cocoa Ingredients

| Non-SOI Dark Chocolate Using Cocoa Polyphenols Part. Defat Cocoa Solids Formulation: | SOI Dark Chocolate Using Cocoa Polyphenol Cocoa Solids Nonfat Formulation: | SOI Dark Chocolate Using Commercial Cocoa Solids Nonfat Formulation: |
|---|---|---|
| 41.49% Sugar | 41.4% sugar | 41.4% sugar |
| 3% whole milk powder | 3% whole milk powder | 3% whole milk powder |
| 26% cocoa polyphenol cocoa powder | 52.65% cocoa polyphenol liquor | 52.65% chocolate liquor |
| 4.5% chocolate liquor | 2.35% anhy. milk fat | 2.35% anhy. milk fat |
| 21.75% cocoa butter | 0.01% vanillin | 0.01% vanillin |
| 2.75% anhy. milk fat | 0.5% lecithin | 0.5% lecithin |
| 0.01% vanillin | | |
| 0.5% Lecithin | | |
| Total fat: 31% | Total fat: 31% | Total fat: 31X |
| Particle size: 20 microns | Particle size: 20 microns | Particle size: 20 microns |

Expected Levels of pentamer and total oligomer procyanidins (monomers and n = 2–12; units of ug/g)

| Pentamer: 1205 | Pentamer: 1300 | Pentamer: 185 |
|---|---|---|
| Total: 13748 | Total: 14646 | Total: 3948 |

Actual Levels of pentamer and total oligomer procyanidins (monomers and n = 2–12; units of ug/g)

| Pentamer: 561 | Not performed | Not performed |
|---|---|---|
| Total: 14097 | | |

TABLE 12

Milk Chocolate Formulas Prepared with non-Alkalized Cocoa Ingredients

| Non-SOI Milk Chocolate Using Cocoa Polyphenol Cocoa Solids Formulation: | SOI Milk Chocolate Using Cocoa Polyphenol Cocoa Solids Formulation: | SOI Milk Chocolate Using Commercial Cocoa Solids Formulation: |
|---|---|---|
| 46.9965% Sugar | 46.9965% sugar | 46.9965% sugar |
| 19.5% whole milk powder | 19.5% whole milk powder | 19.5% whole milk powder |
| 4.5% cocoa polyphenol cocoa powder | 13.0% cocoa polyphenol liquor | 13.9% chocolate liquor |
| 5.5% chocolate liquor | 1.6% anhy. milk fat | 1.60% anhy. milk fat |
| 21.4% cocoa butter | 0.0035% vanillin | 0.0035% vanillin |
| 1.6% anhy. milk fat | 0.5% lecithin | 0.5% lecithin |
| | 7.5% cocoa butter | 17.5% cocoa butter |

TABLE 12-continued

Milk Chocolate Formulas Prepared with non-Alkalized Cocoa Ingredients

| 0.035% vanillin | | |
|---|---|---|
| 0.5% lecithin | | |
| Total fat: 31.75% | Total fat: 31.75% | Total fat: 31.75% |
| Particle size: 20 microns | Particle size: 20 microns | Particle size: 20 microns |

Expected Levels of pentamer and total oligomer procyanidins (monomers and n = 2–12; units of ug/g)

| Pentamer: 225 | Pentamer: 343 | Pentamer: 49 |
|---|---|---|
| Total: 2734 | Total: 3867 | Total: 1042 |

Actual levels of pentamer and total oligomer procyanidins (monomers and n = 2–12; units of ug/g)

| Pentamer: 163 | Not performed | Not performed |
|---|---|---|
| Total: 2399 | | |

EXAMPLE 11

Dry Drink Mix with Cocoa Powder Containing Enhanced Levels of Cocoa Polyphenol A dry drink mix containing the cocoa powder of Example 4 having enhanced levels of cocoa polyphenols was made according to the following formulation:

| Ingredient | % |
|---|---|
| Sucrose | 65.0667 |
| Malt Powder | 11.9122 |
| Cocoa Polyphenol Rich Cocoa Powder | 18.0185 |
| Alkalized Cocoa Powder | 4.0041 |
| Vanillin | 0.0025 |
| Lecithin | 0.9960 |
| | 100.00 |

The dry ingredients were batched according to the above formulation and mixed for one hour in a Kitchen Aid Professional Mixer (Model KSM50P) using a wire whip at #2 speed. The lecithin was agglomerated prior to use in the recipe in a Niro-Aeromatic Agglometer (Model STREA/1).

The dry drink mix was evaluated according to the method of Example 5 and found to have the following cocoa polyphenol content:

Pentamer Content: 221 µg/g
Total Polyphenolic Content: 4325 µg/g

Two tablespoons of the dry drink mix (30 g) were added to milk (8 ounces, 2% fat) to form a chocolate flavored drink.

EXAMPLE 12

Savory Sauce with Chocolate Liquor Containing Enhanced Levels of Cocoa Polyphenol A mole sauce containing the chocolate liquor of Example 7 containing enhanced levels of cocoa polyphenol was made according to the following formulation:

| Ingredient | % |
|---|---|
| Chili Powder | 2.4 |
| Olive Oil | 4.8 |
| Cumin | 0.39 |
| Cinnamon | 0.21 |
| Stewed Tomatoes | 90.8 |
| Chocolate Liquor (from Example 7) | 1.4 |
| | 100.00 |

The oil and spices were heated in a MAGNALite saucepan (41/4.5 qt.) on a HOTPOINT stove (Model RS744G0N1BG) over medium high heat (product temperature 102° C.) for about 20 seconds. The stewed tomatoes and liquor were added to the oil/spice mixture and cooked at a product temperature of 85° C. for 5 minutes.

The sauce was evaluated according to the method of Example 5 and found to have the following cocoa polyphenol content:

Pentamer Content: Trace Total Polyphenolic Content: 213 µg/g

One skilled in the art would readily appreciate how to modify the recipe, for example by adding more chocolate liquor, to obtain a product with higher cocoa polyphenol content, particularly a higher pentamer content.

EXAMPLE 13

Cereal Product with Cocoa Powder Containing Enhanced Levels of Cocoa Polyphenol A cereal was made according to the following formulation:

| Ingredient | % |
|---|---|
| Soft Wheat Flour | 37.09 |
| Hard Wheat Flour | 16.64 |
| Sugar, Granulated | 30.33 |
| Sodium bicarbonate | 0.19 |
| Monocalcium Phosphate | 0.19 |
| Glycerol Monostearate | 0.43 |

| Ingredient | % |
| --- | --- |
| Salt | 1.73 |
| Cocoa Powder (from EX. 4) | 13.40 |
| | 100.00 |

All of the ingredients except the cocoa powder were combined in a small ribbon blender and blended 3 minutes. At the end of the mixing cycle, all of the blended materials were pneumatically conveyed to an AccuRate Feeder. The dry blend was fed through the AccuRate Feeder at 40 kg/hr, along with the cocoa polyphenol cocoa powder, which was fed through the K-tron Feeder at 6.18 kg/hr, into a Werner-Pfleiderer Twin Screw Extruder (Model ZSK57 with Bullet Tips). Water was added at a rate of 1.2 1/hr. The extruder was started up using standard operating procedures. Feed rates for dry blend and water were adjusted to targets. The screw RPM was set to 200. The cocoa feeder was adjusted to target and cereal tubes were collected. Empty cereal tubes were fed through the crimper and collected in 2 foot lengths. Separate pillows were made by snapping at crimped edges.

Results:
Pentamer Content: 23 µg/g
Total Polyphenolic Content: 3453 µg/g

EXAMPLE 14

Cooked Vanilla Pudding made with Cocoa Polyphenol Extract

A standard cooked vanilla pudding was made according to the following formulation:

| Ingredient | % |
| --- | --- |
| JELL-O Vanilla Pudding Mix | 95.00 |
| Cocoa Polyphenol Extract | 5.00 |
| | 100.00 |

The pudding was cooked according to the following procedure:

The cocoa polyphenol extract was made according to the extraction process of Example 2 (method 1) and finely ground using a Hamilton Beach Blendmaster blender (Model #50100, type B12). Five percent of the extract was added to the dry-pudding mix and blended using a wire whip. Two cups of whole milk were added to the pudding mixture in a MAGNA Lite saucepan. The dry mixture and milk were cooked and stirred constantly using a wire whip over medium heat on a HOTPOINT stove (Model RS744G0N1BG) until the mixture came to a full boil. The pudding was removed from the heat, poured into a storage container, and stored in the refrigerator.

Results:
Pentamer Content: 70 µg/g
Total Polyphenolic Content: 1559 µg/g

EXAMPLE 15

Brownies with Chocolate Liquor Containing Enhanced Levels of Cocoa Polyphenol

Brownies were made using the chocolate liquor of Example 7 to replace the unsweetened chocolate of a conventional recipe, according to the following formulation:

| Ingredient | % |
| --- | --- |
| Shortening | 12.50 |
| Chocolate Liquor | 9.41 |
| Sugar | 37.60 |
| All Purpose Flour | 23.48 |
| Baking Powder | .14 |
| Salt | .14 |
| Eggs | 16.60 |
| Vanilla | .13 |
| | 100.00 |

The following procedure was used to make the brownies:

Cocoa polyphenol chocolate liquor and shortening were placed into a Kitchen Aid K45 bowl. The bowl was then placed on top of a MAGNA Lite Saucepan (4 1/4.5 qt.), which had 345 grams of boiling (100° C.) water in it. This double boiler was then heated on a HOTPOINT stove (Model #RS744G0N1BG) over low heat until melted, and was removed from heat. The sugar, eggs and vanilla were mixed into the melted mixture. The remaining dry ingredients were mixed in and the dough spread into a greased 13"×9"×2" baking pan. The brownies were baked at 350OF in a HOTPOINT oven (Model #RS744G0N1BG) for about 30 minutes until the brownies pulled away from the sides of the pan.

Results:
Pentamer Content: 97 µg/g
Total Polyphenolic Content: 2981 µg/g

EXAMPLE 16

Chocolate Cookies with Cocoa Powder Containing Enhanced Levels of Cocoa Polyphenol Chocolate cookies were made using the cocoa powder of Example 4 according to the following formulation:

| Ingredient | % |
| --- | --- |
| Soft Butter | 30.50 |
| Confectioner's Sugar | 7.60 |
| Unsifted Flour | 45.80 |
| Cocoa Polyphenol Cocoa Powder | 15.30 |
| Water | .35 |
| Vanilla Extract | .45 |
| | 100.00 |

The process outlined below was used to make the cookies:

The oven was pre-heated to 325° F. The butter and one-fourth of the sugar were creamed in a Kitchen Aid Model KSM90 for about 2 minutes. The remaining ingredients were added and mixed well (approx. 3 minutes). The dough was shaped into small balls and put on an ungreased cookie sheet. Cookies were baked at 325° F. for 15–17 minutes.

Results (After Baking):
Pentamer Content: 46 µg/g
Total Polyphenolic Content: 3841 µg/g

EXAMPLE 17

Rice and Sauce Mix with Cocoa Polyphenol Extract

A rice and sauce mix is prepared using the formulation below:

| Ingredient | % |
| --- | --- |
| Seasoning Mix w/Cheese | 11.00 |
| Dried Vegetables | 2.00 |
| Dry Rice | 83.00 |
| Cocoa Polyphenol Extract | 4.00 |
| | 100.00 |

All of the ingredients are combined in a saucepan on the stove, and are brought to a boil. Once the mixture is boiling, the heat is reduced and the mixture is simmered for about 10 minutes.

Theoretical results assuming no loss during processing:
Pentamer Content: 1190 µg/g
Total Polyphenolic Content: 15,000 µg/g A rice and cheese sauce mix is prepared using the formulation below:

| Ingredient | % |
| --- | --- |
| Seasoning Mix w/Cheese | 22.00 |
| Dried Vegetables | 3.00 |
| Dry Rice | 71.00 |
| Cocoa Polyphenol Extract | 4.00 |
| | 100.00 |

All of the ingredients are combined in a saucepan with 2¼ cups water and 1 to 2 tablespoons of butter. The mixture is brought to a boil and then is allowed to simmer for about 10 minutes, until most of the water is absorbed. The rice mix is then allowed to sit for about 5 minutes to allow the cheese sauce to thicken.

Theoretical results assuming no loss during processing:
Pentamer Content: 1190 µg/g
Total Polyphenolic Content: 15000 µg/g

EXAMPLE 18

Extruded Energy Bar Process with Cocoa Powder Having Enhanced Levels of Cocoa Polyphenol Energy Bars were made using the cocoa powder of Example 4 having enhanced levels of cocoa polyphenol in place of natural cocoa powder, according to the following recipe:

| Ingredient | % |
| --- | --- |
| Carbohydrate Syrup | 20–30 |
| Fruit/Fruit Preparation | 10–15 |
| Protein Powder (milk or soy origin) | 5–20 |
| Micronutrients | 4–5 |
| Simple Sugars | 10–20 |
| Maltodextrin | 10–15 |
| Crisp Rice/Rice | 10–13 |
| Cocoa Polyphenol Cocoa Powder | 8–12 |
| Fat | 2–5 |
| Flavor | 0.1–1.5 |

The ingredients were mixed in a JH Day 50 gallon jacketed stainless steel double arm sigma blade mixture. The mixer jacket was set to 50° C. The carbohydrate syrup, fat, and fruit/fruit preparation was combined in the mixer and mixed at 50 rpm until homogenous, about 5 minutes. With the mixer running, the remaining ingredients were gradually added in the following order and blended until homogenous; micronutrients, flavor, cocoa powder, simple sugars, maltodextrin, protein powder, and crisp rice/rice. The blended energy bar mass was transferred to the hopper of the Werner Lehara Continuous Rope Extruder. The extruder was jacketed at 40° C. to keep the mass soft and pliable for forming. The mass was extruded through the nozzle block onto a conveyor belt that transferred the strips through a cooling tunnel. A guillotine was used to cut the bars to length upon exiting the cooling tunnel at 15–20° C.

Results:
Pentamer Content: 22 µg/g
Total Polyphenolic Content: 1710 µg/g

EXAMPLE 19

Baby Food containing Cocoa Polyphenol Extract

A vegetable baby food containing cocoa polyphenol extract is prepared using the following formulation:

| Ingredient | Example 19A (%) | Example 19B (%) |
| --- | --- | --- |
| Vegetable<sup>A</sup> | 73 | 60 |
| Liquid<sup>B</sup> | 22 | 35 |
| Cocoa Polyphenol Extract | 5 | 5 |

Ingredient (A): Potatoes, green beans, peas, carrots, and yellow squash.
Ingredient (B): Cooking liquid, formula, or water.

Vegetables are cooked by steaming, microwave oven, or boiling (using small amounts of water which are retained for thinning the pureed food). After cooking, all ingredients are mixed together, placed in a blender and pureed until a smooth consistency is reached.

Theoretical results assuming no loss during processing:
Total Pentamer Content: 1488 µg/g
Total Polyphenolic Content: 18758 µg/g

EXAMPLE 20

Pat Food with Cocoa Powder Having Enhanced Levels of Cocoa Polyphenol

A canned dog/cat food is prepared with cocoa powder having enhanced levels of cocoa polyphenol using the following formulation:

| Ingredients | Example 20A (%) | Example 20B (%) |
| --- | --- | --- |
| Meat/meat by-products | 68 | 52 |
| Water | 24 | 35 |
| Cereals and grains | 0 | 5 |
| Colors, vitamins, minerals, gums, emulsifiers, flavorings, and preservatives | 3 | 3 |
| Cocoa Polyphenol Cocoa Powder | 5 | 5 |

The mixture of meats, animal by-products, cereal components and cocoa polyphenol cocoa powder are hermetically sealed in metal or plastic containers and processed at temperatures and pressures sufficient to render them commercially sterile. The product is heat treated in hermetically sealed containers with an Fo value of 3.0 or more, for canned pet food.

Theoretical results assuming no loss during processing:
Pentamer Content: 107 µg/g
Total Polyphenolic Content: 1554 µg/g

EXAMPLE 21

Dry Pet Food With Cocoa Powder Having Enhanced Levels of Cocoa Polyphenol

A dry extruded dog/cat food is prepared with cocoa powder having enhanced levels of cocoa polyphenols using the following formulation:

| Ingredient | % |
| --- | --- |
| Grains, meat/meat by-products, meat meals | 57–66 |
| Dairy by-products | 24–33 |
| Colors, vitamins, minerals, gums, emulsifiers, flavorings, and preservatives | 3 |
| Cocoa Polyphenol Cocoa Powder | 5 |

The meal is processed in a continuous cooking extruder for approximately 20 seconds reaching 145° C. for approximately 10 seconds. The wet-formed pieces of pet food are dried by means of a conventional belt dryer subjected to air temperatures of 125° C. for approximately 10 minutes. The product is then coated with animal fat and/or emulsified, hydrolyzed animal tissue.

Theoretical results assuming no loss during processing:
Pentamer Content: 107 µg/g
Total Polyphenolic Content: 1554 µg/g

EXAMPLE 22

Chocolate syrup With Cocoa Polyphenol Cocoa Powder

A chocolate variegating and sundae topping syrup containing the cocoa polyphenol cocoa powder are prepared using the following formula:

| Ingredients | Economy Formula (%) | Premium Formula (%) |
| --- | --- | --- |
| Water | 30.74 | 31.56 |
| Corn syrup solids | 35.07 | 30.91 |
| Sucrose | 22.20 | 20.94 |
| Cocoa Polyphenol Cocoa Powder | 8.88 | 7.98 |
| Hydrogenated vegetable fat | 0 | 5.98 |
| Milk solids non-fat | 2.22 | 1.99 |
| CC-801* | 0.72 | 0.49 |
| CC-280 (emulsifier) | 0.17 | 0.15 |
| | 100.00 | 100.00 |

*CC-801 (Pectin, Dextrose, Sodium citrate) is added at 0.20% in the above formulas for chocolate sundae topping syrup; remainder replaced with water to 100%.

For each pound of CC-801, one gallon of water from the formula is heated to 180° F. in a small vat. The CC-801 is stirred in and is set aside until ready to homogenize the complete batch. The balance of the water is added to a steam-jacketed vat. In the following order, the sucrose, milk solids non-fat, and corn-syrup solids are incorporated. The balance of the ingredients are then added in any order. The mixture is heated to 185° F. and held for 5 minutes. The CC-801 solution is added and mixed thoroughly. The batch is at 1000 psi (if not homogenizing, increase the stabilizer 35%). The product is pumped into sanitized containers and stored in a cooler at 40° F. to allow the product to set up.

Theoretical results assuming no loss during processing:
Pentamer Content: 171 µg/g
Total Polyphenolic Content: 2486 µg/g

EXAMPLE 23

Hard Candy

Formed and deposited types of hard candy are prepared using the formulation below by the methods described in Lees & Jackson, 1st Edition, *Sugar Confectionery and Chocolate Manufacture*, pages 176–186 (1995).

| Hard candy Formula | % |
| --- | --- |
| Sugar | 42.85% |
| High Maltose Corn Syrup | 38.09% |
| Water | 12.19% |
| Buffered Lactic Acid | 1.90% |
| Flavoring | 0.19% |
| Coloring | 0.0057% |
| Cocoa Polyphenol Cocoa Powder | 4.77% |

Theoretical results assuming no loss during processing:
Pentamer Content: 102 µg/g
Total Polyphenolic Content: 1482 µg/g

EXAMPLE 24

Rice Cake with Cocoa Polyphenol Cocoa Powder

A cocoa polyphenol cocoa powder covered rice cake was prepared using the following ingredients:

Puffed Rice Cake (made by a method similar to that set forth in U.S. Pat. No. 4,888,180)

N-Tack (corn syrup solids in 30% solution)

Cocoa Polyphenol Cocoa Powder Mix

A prepared rice cake was coated with a thin layer of N-Tack solution. The coated rice cake was immediately placed in a bag containing the cocoa polyphenol mix and coated. The cake was then shaken to remove excess cocoa polyphenol mix. The cake was given a second application of N-Tack and mix resulting in approximately 4 grams of cocoa polyphenol mix being applied to the puffed rice cake.

|  | Theoretical | Actual |
|---|---|---|
| Pentamer Content (µg/g) | 252 | 38 |
| Total Polyphenolic Content (µg/g) | 3655 | 4842 |

EXAMPLE 25

Fruit and Grain Pastry Bar with Cocoa Polyphenol Extract

A strawberry fruit filling was made according to the following formulation:

| Ingredient | wet wt % | amount (g) |
|---|---|---|
| Xanthan gum, extra fine | 1.0 | 5.0 |
| Hydrogenated soybean oil | 1.25 | 6.25 |
| Water | 10.0 | 50.0 |
| Glycerin USP or food grade | 7.0 | 35.0 |
| Corn syrup solids Maltrin M250 (78% solids with 61.9 g water) | 56.23 | 281.2 |
| Low moisture apple flake powder | 5.0 | 25.0 |
| Natural strawberry flavor | 2.0 | 10.0 |
| Strawberry puree concentrate | 12.0 | 60.0 |
| Malic acid, fine granular | 0.5 | 2.5 |
| Red #40 strawberry color | 0.02 | 0.1 |
| Cocoa Polyphenol Extract | 5.0 | 25.0 |
|  | 100.00 | 500.00 |

For making the fruit filling, the gum was hydrated in cold water using a blender. The corn syrup solids, water, fruit puree, cocoa polyphenol extract and glycerin were cooked on a stove top using medium to high heat to a temperature of 230° F. measured with a Wahl thermocouple thermometer. The mixture was removed from the heat and allowed to cool. Hydrated gum was added to the mixture and the mixture was heated to 216° F. The mixture was again removed from the heat and allowed to cool for at least 5 minutes. Acid, color, apple powder and melted fat were added to the mixture, and the mixture was allowed to cool for 2 additional minutes. Flavor was added to the mixture with thorough mixing.

Results:
Pentamer Content: 349 µg/g
Total Polyphenolic Content: 12,771 µg/g

The pastry wrapper was made according to the following formulation:

| Ingredient | wet wt % | amount (g) |
|---|---|---|
| Blended flour 30% hard flour (54.75 g) 70% soft flour (127.75 g) | 36.5 | 182.5 |
| Brown sugar roasted oats | 14.6 | 73.0 |
| Wheat bran | 7.3 | 36.5 |
| Gum arabic (Acacia FCC) | 0.6 | 3.0 |
| Kelco gum (Kelite CM) | 0.6 | 3.0 |
| Soy lecithin | 0.8 | 4.0 |
| Sodium bicarbonate | 0.6 | 3.0 |
| Sodium acid pyrophosphate | 0.4 | 2.0 |
| Brown sugar, granulated | 6.3 | 31.5 |
| Hydrogenated soybean oil | 5.2 | 26.0 |
| Water | 21.22 | 106.1 |
| Flour salt | 1.0 | 5.0 |
| Glycerin USP or food grade | 4.1 | 20.5 |
| Kelco GFS, prehydrated | 0.78 | 3.9 |
|  | 100.00 | 500.00 |

For making the pastry wrapper, the gum arabic, Kelite CM, sodium bicarbonate, sodium acid pyrophosphate, salt, Kelco GFS and glycerin were hydrated in water using a blender. Lecithin was stirred into melted fat. The remaining dry ingredients were added to a mixing bowl. The fat blend was added to the dry ingredients using a Kitchen Aid mixer on speed 2. The gum blend was slowly added into the mixing bowl. After mixing, the dough was worked by hand into a ball. The dough was proofed for 15 minutes covered with a wet paper towel to decrease stickiness. A Rondo Sheeter (Sewer Rondo, Inc. STE533) was used to achieve a dough thickness of 2.5 mm. The dough was cut into 4"×4" squares weighing 33 g.

Using a pastry bag, 19.5 g of the fruit filling was applied on top of each dough square. The dough was folded over to make a bar and the ends of the bar were sealed shut with crimping. Using a knife, holes were poked in the top of the bar to help heat escape and to prevent bar explosion.

The bars were baked for 6½ minutes at 375° F. The weight of the final, baked bar was 45.5 g.

Results:
Pentamer Content: 105 µg/g
Total Polyphenolic Content: 5,851 µg/g

EXAMPLE 26

Caramel Chew with Cocoa Powder Containing Enhanced Levels of Cocoa Polyphenol

Sample A: Cocoa Polyphenol Caramel Chew 15

| Ingredients | Caramel portion (67.00%) | Cocoa/Sugar Premix (33.00%) | Final Chocolate Chew After Cooking (Dry wt. basis) |
|---|---|---|---|
| 63 DE Corn Syrup | 56.70 | | 35.00 |
| Salt | 0.60 | | 0.44 |
| Sweetened Condensed Skim Milk | 34.20 | | 17.70 |
| Partially Hydrogenated Soy Bean Oil 6016 | 8.50 | | 6.30 |
| Cocoa Polyphenol Cocoa 011797B | | 45.5 | 14.66 |
| Fondant Sugar (Redi-Fond from Domino Sugar) | | 54.5 | 18.00 |
| Water | | | 7.90 |
| | 100.00 | 100.00 | 100.00 |

The caramel portion was batched according to the above formulation and combined with agitating and steam in a Groen kettle. The mixture was heated slowly with agitation to 235° F. and cooled to 200° F. or lower.

For making the finished chocolate chew, the cocoa polyphenol cocoa powder and fondant sugar were blended. The caramel portion (67.0% of the final formula) was placed in a Hobart Mixer. While mixing, the cocoa/sugar premix (33.0% of the final formula) was slowly added. The formulation was slabbed to the desired thickness (10 mm). After cooling and setting up (about 2 hours), the formulation was cut to the desired size (20 mm squares).

Results:
Pentamer Content (cocoa added at 140° F.): 95 μg/g
Total Polyphenolic Content (cocoa added at 140° F.): 2195 μg/g Sample B: Cocoa Polyphenol Caramel Chew 22

| Ingredients | Caramel portion (67.00%) | Cocoa/Sugar Premix (33.00%) | Final Chocolate Chew After Cooking (Dry wt. basis) |
|---|---|---|---|
| 63 DE Corn Syrup | 56.70 | | 35.20 |
| Salt | 0.60 | | 0.44 |
| Sweetened Condensed Skim Milk | 34.20 | | 17.70 |
| Partially Hydrogenated Soy Bean Oil 6016 | 8.50 | | 6.29 |
| Cocoa Polyphenol Cocoa 011797B | | 66.7 | 21.34 |
| Fondant Sugar (Redi-Fond from Domino Sugar) | | 33.3 | 10.95 |
| Water | | | 8.08 |
| | 100.00 | 100.00 | 100.00 |

The caramel portion was batched according to the above formulation and combined with agitating and steam in a Groen kettle. The mixture was heated slowly with agitation to 235° F. and cooled to 200° F. or lower.

For making the finished chocolate chew, the cocoa polyphenol cocoa powder and fondant sugar were blended. The caramel portion (67.0% of the final formula) was placed in a Hobart Mixer. While mixing, the cocoa/sugar premix (33.0% of the final formula) was slowly added. The formulation was slabbed to the desired thickness (10 mm). After cooling and setting up (about 2 hours), the formulation was cut to the desired size (20 mm squares).

Results:
Pentamer Content (cocoa added at 140° F.): 178 μg/g
Pentamer Content (cocoa added at 200° F.): 178 μg/g
Total Polyphenolic Content (cocoa added at 140° F.): 4036 μg/g
Total Polyphenolic Content (cocoa added at 200° F.): 3941 μg/g

EXAMPLE 27

Sugar Tablets with Cocoa Powder Containing Enhanced Levels of Cocoa Polylhenol

Wet process tablets were made according to the following formulation:

| | Wet Cocoa Tablet | Final Cocoa Tablet After Drying (Dry wt. basis) |
|---|---|---|
| Sucrose - 6X | 41.30 | 51.19 |
| Cocoa Polyphenol Cocoa Powder | 35.00 | 42.08 |
| Water | 21.66 | 4.50 |
| Gum Arabic | 1.26 | 1.41 |
| Gelatin 200 Bloom | 0.62 | 0.73 |
| Vanilla 4X | 0.76 | 0.09 |
| | 100.00 | 100.00 |

The gelatin was soaked in water and the sucrose was premixed with the cocoa polyphenol cocoa powder. After the gelatin is hydrated, it was heated to 90° C. and gum arabic was added with high shear. This solution, with flavor, was mixed into ¼ of the sucrose/cocoa mixture, and the remaining sucrose/cocoa was slowly added while mixing (in a Hobart or Kitchen Aid Ultra Power mixer). The formulation was mixed for 10–15 minutes and slabbed to the desired thickness (~5 mm). After drying and punching out in the desired shape (discs), the pieces were dried further to a final moisture of approximately 3–6%.

Analytical results:

| Sample | Total Procyanidin microgram/ gram | Pentamers microgram /gram | moisture percent | notes |
|---|---|---|---|---|
| Tablet #5 with Cocoa Polyphenol 112696M | 13618 | 689 | 4.4 | ambient dried |
| Tablet #5 with Cocoa Polyphenol 011797B | 7602 | 215 | 6.2 | ambient dried |
| Tablet #5 Cocoa Polyphenol 011797B | 8186 | 209 | 4.5 | dried at 120° F. for 60 hours |

EXAMPLE 28

Granola Bar

A granola bar was made according to the following formulation:

| BINDER | % |
|---|---|
| 63 D.E. Corn Syrup | 64.11 |
| Partially Hydrogenated Soybean Oil (6034) | 7.9 |
| Cocoa Polyphenol Cocoa Powder | 10 |
| Calcium Carbonate | 7.4 |
| Glycerin | 7 |
| Brown Sugar (Granulated) | 1 |
| Flour Salt | 1.5 |
| Soy Lecithin | 0.3 |
| Propylgallate Solution | 0.04 |
| Vanilla Extract | 0.75 |
| | 100% |

For making the binder, the hydrogenated soybean oil and chocolate liquor were melted in a microwave oven at 55–64° C. The soy lecithin was dispersed into the melted oil, and the mixture was poured into a Cuisinart Mixer. The corn syrup and glycerin were preheated in a microwave to 70° C. to reduce the viscosity and added to the Cuisinart mixture along with oil, lecithin, and liquor. The ingredients were mixed in the Cuisinart for approximately 30 seconds. The dry blended ingredients were slowly added to the Cuisinart and mixed for approximately 1–2 minutes or until well blended.

A fudge formulation using cocoa polyphenol cocoa powder was made according to the following recipe:

| FUDGE TOPPING | % |
|---|---|
| Powdered Sugar (6X) | 27.4 |
| High Fructose Corn Syrup (55%) | 20.0 |
| Partially Hydrogenated Soybean Oil (6034) | 10.75 |
| Lactose (Alpha Mono) | 9.25 |
| Powdered Lactose (Alpha Mono) | 11.0 |
| Cocoa Polyphenol Cocoa Powder | 10.0 |
| Glycerin | 2.0 |
| Non-Fat Dry Milk (Low-Heat) | 5.0 |
| Water | 2.0 |

| FUDGE TOPPING | % |
|---|---|
| Calcium Carbonate | 1.35 |
| Soy Lecithin | 0.5 |
| Salt | 0.25 |
| Vanilla | 0.5 |
| | 100% |

For making the fudge topping, the dry ingredients according to the above recipe were blended in a Kitchen Aid mixer on low speed for approximately 3–4 minutes or until well blended. The hydrogenated soybean oil was melted in a microwave oven at 55–64° C. The soy lecithin was dispersed in the melted oil. The oil/lecithin mixture was poured into the blended dry ingredients in a Hobart Mixer running on slow speed. The speed of the mixture was gradually increased and the water, glycerin, and high fructose corn syrup was added into the mix. The resulting fudge topping was mixed for 2–3 minutes or until thoroughly blended.

The finished bars were made according to the following formulations:
Granola Recipe:

| | |
|---|---|
| Crisp Rice | 30.2 |
| Mini Wheat Flakes | 33.7 |
| Brown Sugar Oats | 36.1 |
| | 100% |

Finished Product Profile:

| | % |
|---|---|
| Chocolate (5% Cocoa Polyphenol Cocoa Powder) | 37 |
| Granola/Rice | 21 |
| Binder | 21 |
| Fudge | 21 |
| | 100% |

The finished product was made according to the following:

The granola was blended with the binder and slabbed onto wax paper with a rolling pin to about 15 mm high. The fudge topping was slabbed onto the granola base and allowed to set for about an hour. The bars were cut to the following dimensions:

| | |
|---|---|
| Height | 15 mm |
| Width | 25 mm |
| Length | 84 mm |

Cut bars were then enrobed in Cocoa Polyphenol chocolate.
Results:
Pentamer: 104 μg/g
Total Polyohenolics: 2215 μg/g

EXAMPLE 29

Cocoa Polyphenol Milk Chocolate with Cinnamon Caramel

Cocoa polyphenol milk chocolate was hand tempered at 86° F.–88° F. The tempered chocolate was then used to make shells in various shaped molds. 965 grams of standard Caramel was warmed to 55° C. 20 grams of cocoa polyphenol cocoa powder and 15 grams of cinnamon were added to the warmed caramel and mixed well. The caramel was allowed to cool and was then pastry bagged into chocolate shells. The shells were then bottomed with tempered chocolate and removed from the molds. The molded piece consisted of 6 grams of cocoa polyphenol milk chocolate and 4 grams of caramel containing 2.0% cocoa polyphenol cocoa powder.

Finished Product:

| Ingredient | Usage Level % |
|---|---|
| Cocoa Polyphenol Milk Chocolate | 60 |
| Cocoa Polyphenol Caramel | 40 |
| | 100% |

Results:
Pentamer: 79.8 µg/g

EXAMPLE 30

Cocoa Polyphenol Milk Chocolate with Chocolate-Flavored Nougat

Cocoa polyphenol milk chocolate was hand tempered at 86° F.–88° F. The tempered chocolate was then used to make shells in various shaped molds. The formula for chocolate-flavored nougat was used to make frappe. 5 grams of cocoa polyphenol cocoa powder was added to 104 grams of slurry which was folded into the frappe at a ratio of 92.40% frappe to 7.60% slurry. The finished chocolate-flavored nougat was then slabbed onto the cooling table and cut to fit the molded shells. The shells were then bottomed with tempered cocoa polyphenol chocolate and removed from the molds. The molded piece consisted of 22.5 grams of cocoa polyphenol milk chocolate and 12.5 grams of chocolate-flavored nougat.

| Cocoa Polyphenol Nougat Ingredient | Piece Wt. = 35 g Usage Level | Choc/Center = 22.5 g/12.5 g |
|---|---|---|
| Chocolate-Flavored Nougat | 35.71% | 17 |
| Cocoa Polyphenol Milk Chocolate | 64.29% | |

Results:
Pentamer: 80.3 µg/g

EXAMPLE 31

Cocoa Polyphenol Dark Chocolate with Chocolate-Flavored Nougat

Cocoa polyphenol milk chocolate was hand tempered at 86° F.–88° F. The tempered chocolate was then used to make shells in various shaped molds. The formula for chocolate-flavored nougat was used to make frappe. 5 grams of cocoa polyphenol cocoa powder and 75 grams of cocoa polyphenol dark chocolate was added to 104 grams slurry which was folded into the frappe at a racial of 92.40% frappe to 7.60% slurry. The finished chocolate-flavored nougat was then slabbed onto the cooling table and cut to fit the molded shells. The shells were then bottomed with tempered cocoa polyphenol chocolate and removed from the molds. The molded piece consisted of 22.5 grams of cocoa polyphenol dark chocolate and 12.5 grams of chocolate-flavored nougat.

Cocoa Polyphenol Chocolate-Flavored Nougat

| Ingredient | Usage Level | # of Samples |
|---|---|---|
| Chocolate-Flavored Nougat | 84.89% | 20 |
| Cocoa Polyphenol Dark Chocolate | 15.0% | |
| Cocoa Polyphenol Cocoa Powder | 0.11% | |

Results:
Pentamer: 43.2 µg/g

What is claimed is:

1. An improved method for preparing chocolate liquor and partially defatted cocoa solids from the roasted cocoa beans or roasted cocoa nibs, the improvement comprising the selection of cocoa beans or blends thereof having a fermentation factor of 275 or less.

2. The method of claim 1, which comprises the steps of:
   (a) roasting the selected cocoa beans or blends thereof to an internal bean temperature of about 95° C. to about 160° C.;
   (b) winnowing the cocoa nibs from the roasted cocoa beans; and
   (c) milling the cocoa nibs into the chocolate liquor.

3. The method of claim 1, which comprises the steps of:
   (a) heating the selected cocoa beans at a temperature to about 95° to about 135° C. to loosen the cocoa shell from the cocoa nibs;
   (b) winnowing the cocoa nibs from the cocoa shells;
   (c) roasting the cocoa nibs to an internal nib temperature of about 95° C. to about 160° C.; and
   (d) milling the roasted nibs into the chocolate liquor.

4. The method of claim 1, which comprises the steps of:
   (a) roasting the selected cocoa beans or blends thereof to an internal bean temperature of about 95° C. to about 160° C.;
   (b) winnowing the roasted cocoa nibs from the roasted cocoa beans;
   (c) milling the roasted cocoa nibs into the chocolate liquor; and
   (d) recovering cocoa butter and the partially defatted cocoa solids from the cocoa liquor.

5. The method of claim 1, which comprises the steps of:
   (a) heating the selected cocoa beans or blends thereof to a temperature just sufficient to loosen the cocoa shell from the cocoa nibs;
   (b) winnowing the cocoa nibs from the cocoa shells;
   (c) roasting the cocoa nibs to an internal nib temperature of about 95° C. to about 150° C.;
   (d) milling the roasted nibs into the chocolate liquor; and
   (e) recovering cocoa butter and the partially defatted cocoa solids from the cocoa liquor.

6. The method of claims 2, 3, 4, or 5, wherein the roasting temperature is about 95° C. to about 120° C.

7. The method of claim 6 wherein the roasting time is 1 minute to 1 hour.

8. Roasted cocoa nibs, or fractions thereof, prepared from cocoa beans having a fermentation factor of 275 or less.

9. Chocolate liquor prepared from roasted cocoa beans having a fermentation factor of 275 or less.

10. Chocolate liquor containing at least about 50,000 µg of total cocoa procyanidins per gram of nonfat cocoa solids.

11. Chocolate liquor containing at least about 5,000 μg of cocoa procyanidin pentamer per gram of nonfat cocoa solids.

12. A food containing the chocolate liquor of claims 9, 10, or 11.

13. The food product of claim 12 wherein the food product is a pet food, a dry cocoa mix, a pudding, a syrup, a cookie, a savory sauce, a rice mix, a rice cake, or chocolate confectionary.

14. Partially defatted cocoa solids prepared from roasted cocoa beans or blends thereof having a fermentation factor of 275 or less.

15. Partially defatted cocoa solids containing at least about 50,000 μg of cocoa procyanidin pentamer per gram of nonfat cocoa solids.

16. Partially defatted cocoa solids containing at least about 5,000 μg of cocoa procyanidin pentamer per gram of nonfat cocoa solids.

17. A food containing the partially defatted cocoa solids of claim 14, 15, or 16.

18. The food product of claim 17, wherein the food product is a pet food, a dry cocoa mix, a pudding, a syrup, a cookie, a savory sauce, a rice mix, a rice cake, or chocolate confectionary.

19. An extract containing cocoa polyphenols including cocoa procyanidins, which is prepared by solvent extracting partially defatted cocoa solids prepared from cocoa beans or cocoa nibs having a fermentation factor of 275 or less which have been roasted to an internal bean or nib temperature of about 95° C. to about 160° C.

20. A food containing the extract of claim 11.

21. The food product of claim 20, wherein the food product is a pet food, a dry cocoa mix, a pudding, a syrup, a cookie, a savory sauce, a rice mix, a rice cake, or chocolate confectionary.

22. A food product containing at least about 15,100 μg of total cocoa procyanidins per gram of nonfat cocoa solids, when the nonfat cocoa solids content of the food product is less than or equal to 7% by weight based on the total weight of the food product.

23. A food product containing at least about 700 μg of cocoa procyanidin pemtamer per gram of cocoa solids, when the nonfat cocoa solids content of the food product is less than or equal to 7% by weight based on the total weight of the food product.

24. The food product of claim 22 wherein the food product is a milk chocolate.

25. A food product containing at least 17,000 μg of total cocoa procyanidins per gram of nonfat cocoa solids, when the nonfat cocoa solids content of the food product is less than or equal to about 13% based on the total weight of the food product.

26. A food product containing at least 1400 μg of cocoa procyanidin pentamer per gram of nonfat cocoa solids, when the nonfat cocoa solids content of the food product is less than or equal to about 16% based on the total weight of the food product.

27. A food product containing at least about 22,065 μg of total cocoa procyanidins per gram of cocoa nonfat solids, when the nonfat cocoa solids content of the food product is at least about 35% nonfat cocoa solids based on the total weight of the food product.

28. A food product containing at least about 20,500 μg of total cocoa procyanidins per gram of nonfat cocoa solids, when the nonfat cocoa solids content of the food product is at least about 37% nonfat cocoa solids based on the total weight of the food product.

29. A food product containing at least about 1,860 μg of cocoa procyanidin pentamer per gram of nonfat cocoa solids, when the nonfat cocoa solids content of the food product is at least about 37% nonfat cocoa solids based on the total weight of the food product.

30. The food product of claim 22, wherein the food product is a dark chocolate.

31. A food product containing at least about 15,000 μg of total cocoa procyanidins per gram of nonfat cocoa solids, when the nonfat cocoa solids content of the food product is less than about 30% based on the total weight of the food product.

32. A cocoa powder dry mix containing about 4325 μg of total cocoa procyanidins per gram of nonfat cocoa solids, when the nonfat cocoa solids content of the dry mix is about 16% based on the total weight of the dry mix.

33. A method of improving the health of a mammal, which method comprises administering to the mammal a composition containing at least one cocoa polyphenol ingredient, which ingredient is selected from the group consisting of chocolate liquor, partially defatted cocoa solids, synthetic procyanidin monomers and oligomers, derivatives of the synthetic procyanidin monomers and oligomers, which ingredients are prepared from underfermented cocoa beans having a fermentation factor of 275 or less.

\* \* \* \* \*

UNITED STATES PATENT AND TRADEMARK OFFICE
CERTIFICATE OF CORRECTION

PATENT NO. : 6,312,753 B1
DATED : November 6, 2001
INVENTOR(S) : Kirk S. Kealey et al.

It is certified that error appears in the above-identified patent and that said Letters Patent is hereby corrected as shown below:

Column 66,
Line 46, "cocoa liquor" has been deleted, and -- chocolate liquor -- has been inserted therefor.
Line 64, after "roasted cocoa beans", -- or blends thereof -- has been inserted.

Column 67,
Line 31, "11" has been changed to -- 19 --.

Columns 67-68,
Claims 23, 26, 27, 28, 29 and 33 have been deleted.

Signed and Sealed this

Fourth Day of June, 2002

*Attest:*

JAMES E. ROGAN
*Attesting Officer*     *Director of the United States Patent and Trademark Office*

UNITED STATES PATENT AND TRADEMARK OFFICE
CERTIFICATE OF CORRECTION

PATENT NO.   : 6,312,753 B1
DATED        : November 6, 2001
INVENTOR(S)  : Kirk S. Kealsey et al.

It is certified that error appears in the above-identified patent and that said Letters Patent is hereby corrected as shown below:

<u>Column 67,</u>
Line 14, "cocoa procyanidin pentamer" has been deleted and -- total cocoa procyanidins -- has been inserted therefor.

Signed and Sealed this

Eighteenth Day of May, 2004

JON W. DUDAS
*Acting Director of the United States Patent and Trademark Office*

UNITED STATES PATENT AND TRADEMARK OFFICE
CERTIFICATE OF CORRECTION

| | |
|---|---|
| PATENT NO. | : 6,312,753 B1 |
| APPLICATION NO. | : 09/254353 |
| DATED | : November 6, 2001 |
| INVENTOR(S) | : Kirk S. Kealey et al. |

It is certified that error appears in the above-identified patent and that said Letters Patent is hereby corrected as shown below:

On the title page, item:
At (63)

Delete "Continuation of Application No. 09/041,326 filed on Mar. 12, 1998, now Pat. No. 6,194,020, and a continuation"

Insert -- Continuation --

Signed and Sealed this

Third Day of October, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,312,753 B1 | Page 1 of 1 |
| APPLICATION NO. | : 09/254353 | |
| DATED | : November 6, 2001 | |
| INVENTOR(S) | : Kirk S. Kealey et al. | |

It is certified that error appears in the above-identified patent and that said Letters Patent is hereby corrected as shown below:

On the title page,

At (63)

Delete "Continuation"

Insert -- Continuation-in-part --

Signed and Sealed this

Tenth Day of July, 2007

JON W. DUDAS
*Director of the United States Patent and Trademark Office*